United States Patent
Varasi et al.

(10) Patent No.: US 10,980,777 B2
(45) Date of Patent: Apr. 20, 2021

(54) INDOLE DERIVATIVES AS HISTONE DEMETHYLASE INHIBITORS

(71) Applicant: Istituto Europeo di Oncologia S.r.l., Milan (IT)

(72) Inventors: Mario Varasi, Milan (IT); Anna Cappa, Visso (IT); Paola Vianello, Milan (IT); Loris Moretti, Copenhagen (DK); Luca Sartori, Brunate (IT); Ciro Mercurio, Legnano (IT)

(73) Assignee: Istituto Europeo di Oncologia S.r.l., Milan (IT)

( * ) Notice: Subject to any disclaimer, the term of this patent is extended or adjusted under 35 U.S.C. 154(b) by 0 days.

(21) Appl. No.: 16/640,030

(22) PCT Filed: Aug. 17, 2018

(86) PCT No.: PCT/EP2018/072319
§ 371 (c)(1),
(2) Date: Feb. 18, 2020

(87) PCT Pub. No.: WO2019/034774
PCT Pub. Date: Feb. 21, 2019

(65) Prior Publication Data
US 2020/0289463 A1    Sep. 17, 2020

Related U.S. Application Data

(60) Provisional application No. 62/547,433, filed on Aug. 18, 2017.

(51) Int. Cl.
*A61K 31/407* (2006.01)
*A61K 45/06* (2006.01)
*C07D 495/04* (2006.01)

(52) U.S. Cl.
CPC ............ *A61K 31/407* (2013.01); *A61K 45/06* (2013.01); *C07D 495/04* (2013.01)

(58) Field of Classification Search
CPC ..... A61K 31/407; A61K 45/06; C07D 495/04
USPC ...................................................... 514/269
See application file for complete search history.

(56) References Cited

U.S. PATENT DOCUMENTS

2010/0324147 A1    12/2010   McCafferty et al.

FOREIGN PATENT DOCUMENTS

| EP | 2 993 175 A1 | 3/2016 |
|---|---|---|
| WO | WO 2011/100359 A1 | 8/2011 |
| WO | WO 2011/131576 A1 | 10/2011 |
| WO | WO 2012/045883 A1 | 4/2012 |
| WO | WO 2013/022047 A1 | 2/2013 |
| WO | WO 2013/025805 A1 | 2/2013 |
| WO | WO 2016/034946 A2 | 3/2016 |

OTHER PUBLICATIONS

Anand, R. et al. "Structure and Mechanism of Lysine-specific Demethylase Enzymes", Journal of Biologocal Chemistry, 2007, vol. 282, No. 49, p. 35425-35429.

Benelkebir et al. "Enantioselective synthesis of tranylcypromine analogues as lysine demethylase (LSD1) inhibitors", Bioorg. Med. Chem., 2011, vol. 19, p. 3709-3716.

Bennani-Baiti, I. M. et al. "Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma", Human Pathology, 2012, vol. 43, p. 1300-1307.

Berge, S. M. et al. "Pharmaceutical Salts", Journal of Pharmaceutical Sciences, 1977, vol. 66, No. 1, p. 1-19.

Bighley et al. "Salt Forms of Drugs and Absorption", in Encyclopedia of Pharmaceutical Technology, Marcel Dekker Inc, New York 1996, vol. 13, p. 453-497.

Binda et al. "Biochemical, Structural, and Biological Evaluation of Tranylcypromine Derivatives as Inhibitors of Histone Demethylases LSD1 and LSD2", J. Am. Chem. Soc., 2011, vol. 132, p. 6827-6833, and Supporting Information.

Binda, C. et al. "Insights into the mode of inhibition of human mitochondrial monoamine oxidase B from high-resolution crystal structures", Proc. Natl. Acad. Sci. USA, 2003, p. 9750-9755.

Cho, H. S. et al. "Demethylation of RB Regulator MYPT1 by Histone Demethylase LSD1 Promotes Cell Cycle Progression in Cancer Cells", Cancer Res., 2011, vol. 71, p. 655-660.

Choi, J. et al. "Histone demethylase LSD1 is required to induce skeletal muscle differentiation by regulating myogenic factors", Biochem. Biophys. Res. Commun. 2010, vol. 401, p. 327-332.

Ciccone, D. N. et al. "KDM1B is a histone H3K4 demethylase required to establish maternal genomic imprints", Nature, 2009, vol. 461, p. 415-418.

Culhane, J. C. et al. "LSD1 and the chemistry of histone demethylation", Curr. Opin. Chem. Biol. 2007, vol. 11, p. 561-568.

Duteil et al. "LSD1 promotes oxidative metabolism of white adipose tissue", Nature Communications, 2014, 14 pages.

(Continued)

*Primary Examiner* — Kristin A Vajda

(74) *Attorney, Agent, or Firm* — Cooley LLP

(57) ABSTRACT

The present application relates to compounds of formula (I), wherein A, R, $R^1$, and $R^2$ are as defined in the specification, pharmaceutical compositions containing such compounds and to their use in therapy.

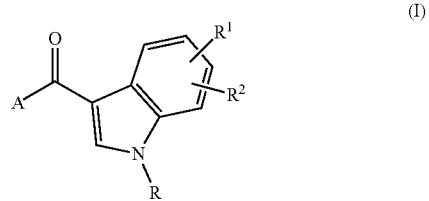

(I)

26 Claims, No Drawings

(56) References Cited

OTHER PUBLICATIONS

Fang, R. et al. "Human LSD2/KDM1b/AOF1 Regulates Gene Transcription by Modulating Intragenic H3K4me2 Methylation", Molecular Cell, 2010, vol. 39, p. 222-233.
Forneris, F. et al. "Structural Basis of LSD1-CoREST Selectivity in Histone H3 Recognition", Journal of Biological Chemistry, 2007, vol. 282, p. 20070-20074.
Gooden et al. "Facile synthesis of substituted trans-2-arylcyclopropylamine inhibitors of the human histone demethylase LSD1 and monoamine oxidases a", Science Direct, Bioorganic & Medicinal Chemistry Letters, 2008, vol. 18, p. 3047-3051.
Gould, P. L. "Salt Selection for basic drugs", International Journal of Pharmaceutics, 1986, vol. 33, p. 201-217.
Gu, H. et al. "Engagement of the Lysine-Specific Demethylase/ HDAC1/CoREST/REST Complex by Herpes Simplex Virus 1", J. Virol. 2009, vol. 83, p. 4376-4385.
Harris et al. "The Histone Demethylase KDM1A Sustains the Oncogenic Potential of MLL-AF9 Leukemia Stem Cells", Cancer Cell, 2012, vol. 21, p. 473-487.
Hayami, S. et al. "Overexpression of LSD1 contributes to human carcinogenesis through chromatin regulation in various cancers", International Journal of Cancer, 2011, vol. 128, p. 574-586.
Hino, S. et al. "FAD-dependent lysine-specific demethylase-1 regulates cellular energy expenditure", Nature Communications, 2012, 12 pages.
Hitchin, J. et al. "Development and evaluation of selective, reversible LSD1 inhibitors derived from fragments", Med. Chem. Commun. 2013, vol. 4, p. 1513-1522.
Hu, X. et al. "LSD1-mediated epigenetic modification is required for TAL1 function and hematopoiesis", Proc. Natl. Acad. Sci. USA 2009, vol. 106, No. 25, p. 10141-10146.
Huang, Y. et al. "Inhibition of lysine-specific demethylase 1 by polyamine analogues results in reexpression of aberrantly silenced genes", Proc. Natl. Acad. Sci. USA 2007, vol. 104, p. 8023-8028.
Huang, Y. et al. "Novel Oligoamine Analogues Inhibit Lysine-Specific Demethylase 1 and Induce Reexpression of Epigenetically Silenced Genes", Clin. Cancer Res. 2009, vol. 15, p. 7217-7228.
Kahl, P. et al. "Androgen Receptor Coactivators Lysine-Specific Histone Demethylase 1 and Four and a Half LIM Domain Protein 2 Predict Risk of Prostate Cancer Recurrence", Cancer Research, 2006, vol. 66, p. 11341-11347.
Karytinos, A. et al. "A Novel Mammalian Flavin-dependent Histone Demethylase", Journal of Biological Chemistry, 2009, vol. 284, p. 17775-17782.
Lee, M. G. et al. "Histone H3 Lysine 4 Demethylation Is a Target of Nonselective Antidepressive Medications", Chemistry & Biology, 2006, vol. 13, p. 563-567.
Li, Y. et al. "Dynamic interaction between TAL1 oncoprotein and LSD1 regulates TAL1 function in hematopoiesis and leukemogenesis", Oncogene, 2012, vol. 31, p. 5007-5018.
Lim, S. et al. "Lysine-specific demethylase 1 (LSD1) is highly expressed in ER-negative breast cancers and a biomarker predicting aggressive biology", Carcinogenesis 2010, vol. 31, p. 512-520.
Lin, T. et al. "Requirement of the histone demethylase LSD1 in Snail-mediated transcriptional repression during epithelial-mesenchymal transition", Oncogene, 2010, vol. 29, p. 4896-4904.
LV, S. et al. "LSD1 is required for chromosome segregation during mitosis", European Journal of Cell Biology, 2010, vol. 89, p. 557-563.
Metzger, E. et al. "The expanding world of histone lysine demethylases", Natural Structural & Molecular Biology, 2007, vol. 14, p. 252-254.
Musri, M. et al. "Histone Demethylase LSD1 Regulates Adipogenesis", Journal of Biological Chemistry, 2010, vol. 285, p. 30034-30041.
Portela, A. et al. "Epigenetic modifications and human disease", Nature Biotechnology, 2010, vol. 28, p. 1057-1068.
Roizman, B. "The Checkpoints of Viral Gene Expression in Productive and Latent Infection: the Role of the HDAC/CoREST/ LSD1/REST Repressor Complex", Journal of Virology, 2011, vol. 85, No. 15, p. 7474-7482.
Sakane, N. et al. "Activation of HIV Transcription by the Viral Tat Protein Requires a Demethylation Step Mediated by Lysinespecific Demethylase 1 (LSD1/KDM1)", PloS Pathogens, 2011, vol. 7, Issue 8, e1002184, 12 pages.
Schenk, T. et al. "Inhibition of the LSD1 (KDM1A) demethylase reactivates the all-trans-retinoic acid differentiation pathway in acute myeloid leukemia", Nature Medicine, 2012, vol. 18, p. 605-611.
Schildhaus, H.-U. et al. "Lysine-specific demethylase 1 is highly expressed in solitary fibrous tumors, synovial sarcomas, rhabdomyosarcomas, desmoplastic small round cell tumors, and malignant peripheral nerve sheath tumors", Human Pathology, 2011, vol. 42, p. 1667-1675.
Schmidt, D. et al."trans-2-Phenylcyclopropylamine Is a Mechanism-Based Inactivator of the Histone Demethylase LSD1", Biochemistry 2007, vol. 46, p. 4408-4416.
Schulte et al. "Lysine-Specific Demethylase 1 Is Strongly Expressed in Poorly Differentiated Neuroblastoma: Implications for Therapy", Cancer Res. 2009, vol. 69, p. 2065-2071.
Scoumanne, A. et al. "The Lysine-specific Demethylase 1 Is Required for Cell Proliferation in Both p53-dependent and -independent Manners" Journal of Biological Chemistry, 2007, vol. 282, No. 21, p. 15471-15475.
Sorna et al. "High-Throughput Virtual Screening Identifies Novel N'-(1-Phenylethylidene)-benzohydrazides as Potent, Specific, and Reversible LSD1 Inhibitors", Journal of Medicinal Chemistry, 2013, vol. 56, p. 9496-9508.
Sun, G. et al. "Histone Demethylase LSD1 Regulates Neural Stem Cell Proliferation", Molecular and Cellular Biology, 2010, vol. 30, p. 1997-2005.
Suva et al. "Reconstructing and Reprogramming the Tumor-Propagating Potential of Glioblastoma Stem-like Cells", Cell, 2014, vol. 157, p. 580-594.
Varier R. et al. "Histone lysine methylation and demethylation pathways in cancer", Biochimica et Biophysica Acta, vol. 1815, No. 1, 2011, pp. 75-89.
Wang, J. et al. "The lysine demethylase LSD1 (KDM1) is required for maintenance of global DNA methylation", Nature Genetics, 2009, vol. 41, No. 1, p. 125-129.
Wang, J. et al. "Novel Histone Demethylase LSD1 Inhibitors Selectively Target Cancer Cells with Pluripotent Stem Cell Properties", Cancer Research, 2011, vol. 71, p. 7238-7249.
Zibetti, C. et al. "Alternative Splicing of the Histone Demethylase LSD1/KDM1 Contributes to the Modulation of Neurite Morphogenesis in the Mammalian Nervous System", Journal of Neuroscience, 2010, vol. 30, p. 2521-2532.

INDOLE DERIVATIVES AS HISTONE DEMETHYLASE INHIBITORS

CROSS-REFERENCE TO RELATED APPLICATIONS

This application is a U.S. National Phase Application, filed under 35 U.S.C. § 371(c), of International Application No. PCT/EP2018/072319, filed Aug. 17, 2018, which claims priority to, and the benefit of, U.S. Application No. 62/547,433, filed Aug. 18, 2017, the contents of each of which are incorporated herein by reference in their entireties.

TECHNICAL FIELD

The present application relates to indole derivatives, pharmaceutical compositions containing such compounds and to their use in therapy.

BACKGROUND

Alterations in the structural and functional states of chromatin, mainly determined by post-translational modifications of histone components, are involved in the pathogenesis of a variety of diseases. The enzymatic processes, which govern these post-translational modifications on the nucleosomes, have become potential targets for the so-called epigenetic therapies (Portela, A. et al. Nat. Biotechnol. 2010, 28, 1057-1068).

The discovery of an increasing number of histone lysine demethylases has highlighted the dynamic nature of the regulation of histone methylation, a key chromatin modification that is involved in eukaryotic genome and gene regulation. Histone lysine demethylases represent attractive targets for epigenetic drugs, since their expression and/or activities are often misregulated in cancer (Varier, R. A. et al. Biochim. Biophys. Acta. 2011, 1815, 75-89). A lysine can be mono-, di-, and tri-methylated and each modification, even on the same amino acid, can have different biological effects.

Histone lysine demethylases exert their activity through two different type of mechanism (Anand, R. et al. J. Biol. Chem. 2007, 282, 35425-35429; Metzger, E. et al. Nat. Struct. Mol. Biol. 2007, 14, 252-254). While the Jumonji domain-containing histone demethylases, which are iron and 2-oxoglutarate dependent oxygenases, act on mono-, di- and trimethylated lysines, the flavin-dependent (FAD) histone demethylases catalyse the cleavage of mono and dimethylated lysine residues. Currently, two FAD dependent demethylases have been identified: LSD1, also known as KDM1A, and LSD2, also known as KDM1B. (Culhane, J. C. et al. Curr. Opin. Chem. Biol. 2007, 11, 561-568, Ciccone, D. N. et al. Nature 2009, 461, 415-418).

KDM1A is a constituent in several chromatin-remodeling complexes and is often associated with the co-repressor protein CoREST. KDM1A specifically removes the methyl groups from mono- and di-methyl Lys4 of histone H3, which is a well-characterized gene activation mark. KDM1A represents an interesting target for epigenetic drugs due to its over-expression in solid and hematological tumors (Schulte, J. H. et al. Cancer Res. 2009, 69, 2065-2071; Lim, S. et al. Carcinogenesis 2010, 31, 512-520; Hayami, S. et al. Int. J. Cancer 2011, 128, 574-586; Schildhaus, H. U. et al. Hum. Pathol. 2011, 42, 1667-1675; Bennani-Baiti, I. M. et al. Hum. Pathol. 2012, 43, 1300-1307). Its over-expression correlates to tumor recurrence in prostate cancer (Kahl, P. et al. Cancer Res. 2006, 66, 11341-11347), and KDM1A has a role in various differentiation processes, such as adipogenesis (Musri, M. M. et al. J. Biol. Chem. 2010, 285, 30034-30041), muscle skeletal differentiation (Choi, J. et al. Biochem. Biophys. Res. Commun. 2010, 401, 327-332), and hematopoiesis (Hu, X. et al. Proc. Natl. Acad. Sci. USA 2009, 106, 10141-10146; Li, Y. et al. Oncogene. 2012, 31, 5007-5018). KDM1A is further involved in the regulation of cellular energy expenditure (Hino S. Et al. Nat Commun. 2012, doi: 10.1038/ncomms1755), in the regulation of thermogenesis and oxidative metabolism in adipose tissue (Duteil et al. Nat Commun. 2014 Jun. 10; 5:4093. doi: 10.1038/ncomms5093.), in the control of checkpoints of viral gene expression in productive and latent infections (Roizman, B. J. Virol. 2011, 85, 7474-7482), and more specifically in the control of herpes virus infection (Gu, H. J. Virol. 2009, 83, 4376-4385) and HIV transcription (Sakane, N. et al. PLoS Pathog. 2011, 7(8):e1002184). The role of KDM1A in the regulation of neural stem cell proliferation (Sun, G. et al. Mol. Cell Biol. 2010, 30, 1997-2005) and in the control of neuritis morphogenesis (Zibetti, C. et al. J. Neurosci. 2010, 30, 2521-2532) suggests its possible involvement in neurodegenerative diseases.

Furthermore, KDM1A has been found to be relevant in the control of other important cellular processes, such as DNA methylation (Wang, J. et al. Nat. Genet. 2009, 41(1): 125-129), cell proliferation (Scoumanne, A. et al. J. Biol. Chem. 2007, 282, 15471-15475; Cho, H. S. et al. Cancer Res. 2011, 71, 655-660), epithelial mesenchimal transition (Lin, T. et al. Oncogene. 2010, 29, 4896-4904) and chromosome segregation (Lv, S. et al. Eur. J. Cell Biol. 2010, 89, 557-563). Moreover, KDM1A inhibitors were able to reactivate silenced tumor suppressor genes (Huang, Y. et al. Proc. Natl. Acad. Sci. USA. 2007, 104, 8023-8028; Huang, Y. et al. Clin. Cancer Res. 2009, 15, 7217-7228), to target selectively cancer cells with pluripotent stem cell properties (Wang, J. et al. Cancer Res. 2011, 71, 7238-7249), as well as to reactivate the all-trans-retinoic acid differentiation pathway in acute myeloid leukemia (Schenk, T. et al. Nat Med. 2012, 18, 605-611). Moreover, KDM1A has a clear role in sustaining the oncogenic potential of MLL-AF9 translocation in leukaemia stem cells (Harris et al. Cancer Cell, 21 (2012), 473-487), as well as in the stem-like tumor propagating cells of human glioblastoma (Suvà et al. Cell 2014, 157, 580-594).

The more recently discovered demethylase KDM1B (LSD2) displays similarly to KDM1A specificity for mono- and di-methylated Lys4 of histone H3. KDM1B, differently from KDM1A, does not bind CoREST and it has not been found up to now in any of KDM1A-containing protein complexes (Karytinos, A. et al. J. Biol. Chem. 2009, 284, 17775-17782). On the contrary, KDM1B forms active complexes with euchromatic histone methyltransferases G9a and NSD3 as well as with cellular factors involved in transcription elongation. KDM1B has been reported to have a role as regulator of transcription elongation rather than that of a transcriptional repressor as proposed for KDM1A (Fang, R. et al. Mol. Cell 2010, 39, 222-233).

KDM1A and KDM1B are both flavo amino oxidase dependent proteins sharing a FAD coenzyme-binding motif, a SWIRM domain and an amine oxidase domain, all of which are integral to the enzymatic activity of KDM1 family members. Moreover, both KDM1A and KDM1B show a structural similarity with the monoamine oxidases MAO-A and MAO-B. Indeed, tranylcypromine, a MAO inhibitor used as antidepressant agent, was found to be also able to inhibit KDM1A. The compound acts as an irreversible inhibitor forming a covalent adduct with the FAD cofactor. (Lee, M. G. et al. Chem. Biol. 2006, 13, 563; Schmidt, D. M.

Z. et al. Biochemistry 2007, 46, 4408). Tranylcypromine analogs and their KDM1A inhibitory activity have been described in Bioorg. Med. Chem. Lett. 2008, 18, 3047-3051, in Bioorg. Med. Chem. 2011, 19, 3709-3716, and in J. Am. Chem. Soc. 2011, 132, 6827-6833. Further arylcyclopropylamine and heteroarylcyclopropylamine derivatives as KDM1A, MAO-A and/or MAO-B enzyme inhibitors are disclosed in US2010/324147, in WO2012/045883, in WO2013/022047 and in WO2011/131576.

Reversible KDM1A inhibitors are not so common and no clinical data for them are so far available. Examples of reversible inhibitors are aminothiazoles as described in Med. Chem. Commun. 2013, 4, 1513-1522, a N'-(1-phenylethylidene)-benzohydrazide series (J. Med. Chem. 2013, 56, 9496-9508, WO2013025805), or thienopyrrole derivatives (WO2016/034946). Thus, there is still a need for further reversible inhibitors having useful antitumor properties, adequate selectivity and stability of action, and showing a higher activity with respect to specific subclasses thereof.

SUMMARY

In one embodiment, the application pertains to a compound of formula (I)

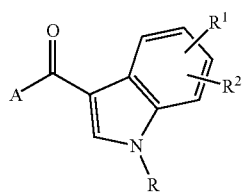

wherein
A is

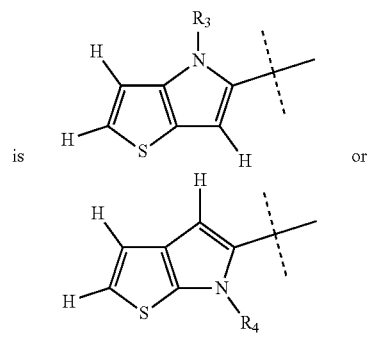

R is hydrogen or $L^1$-$R^5$;
$R^1$, $R^2$ are independently, hydrogen, OH, $C_1$-$C_4$-alkyl, $C_3$-$C_7$ cycloalkyl, aryl, or heteroaryl;
$R_3$, $R_4$ are hydrogen or $C_1$-$C_4$-alkyl;
$L^1$ is a bond, —$(CH_2)_j$—Y— or —$(CH_2)_k$—,
j is an integer from 2 to 6;
k is an integer from 1 to 6;
Y is oxygen;
$R^5$ is $C_1$-$C_4$-alkyl or aryl, wherein the aryl is optionally substituted by one or two substituents chosen from halogen, $C_1$-$C_6$-alkyl, or $L^2$-$R^6$;
$L^2$ is —$(CH_2)_m$—; or —$(CH_2)_n$—W—$(CH_2)_p$—;
$R^6$ is heterocyclyl, wherein the heterocyclyl is optionally substituted by $C_1$-$C_6$-alkyl;

m, n, p are, independently, zero or an integer from 1 to 6;
W is oxygen, NH, or $CH_2$;
or a stereoisomer or a pharmaceutically acceptable salt thereof.

In one embodiment, the application pertains to a compound of formula (I), wherein A is

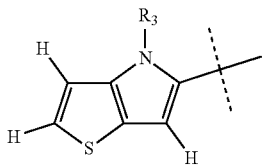

In one embodiment, the application pertains to a compound of formula (I), wherein A is

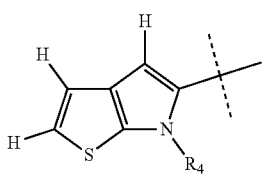

In one embodiment, the application pertains to a compound of formula (I), wherein $R_3$ or $R_4$ are methyl or ethyl.
In one embodiment, the application pertains to a compound of formula (I), wherein
R is hydrogen or $L^1$-$R^5$;
$R^1$, $R^2$ are independently, hydrogen, OH, or $C_1$-$C_4$-alkyl;
$R_3$, $R_4$ are methyl or ethyl;
$L^1$ is a bond, —$(CH_2)_2$—Y— or —$(CH_2)_k$—;
k is an integer from 1 to 4;
Y is oxygen;
$R^5$ is $C_1$-$C_4$-alkyl or phenyl substituted by one or two substituents chosen from $L^2$-$R^6$;
$L^2$ is —W—$(CH_2)_p$—;
$R^6$ is heterocyclyl, wherein the heterocyclyl is optionally substituted by $C_1$-$C_6$-alkyl;
p is zero or 1;
W is oxygen;
or a stereoisomer or a pharmaceutically acceptable salt thereof.

In one embodiment, the application pertains to a compound of formula (I), wherein
R is hydrogen or $L^1$-$R^5$;
$R^1$, $R^2$ are independently H or methyl;
$R_3$, $R_4$ are methyl or ethyl;
$L^1$ is —$(CH_2)_j$—Y— or —$(CH_2)_k$—;
j is 2;
k is 3;
$R^5$ is methyl, or phenyl substituted by one or two substituents chosen from $L^2$-$R^6$;
$L^2$ is —$(CH_2)_n$—W—$(CH_2)_p$—;
n is 0;
p is 0 or 1;
W is oxygen;
or a stereoisomer or a pharmaceutically acceptable salt thereof.

In one embodiment, the application pertains to a compound of formula (I), wherein
R is $L^1$-$R^5$;
$R^1$, $R^2$ are hydrogen;

$R_3$, $R_4$ are methyl or ethyl;
$L^1$ is —$(CH_2)_j$—Y— or —$(CH_2)_k$—;
j is 2;
k is 3;
$R^5$ is phenyl substituted by one or two substituents chosen from $L^2$-$R^6$;
$L^2$ is —$(CH_2)_n$—W—$(CH_2)_p$—;
n is 0;
p is 0 or 1;
W is oxygen;
or a stereoisomer or a pharmaceutically acceptable salt thereof.

In one embodiment, the application pertains to a compound of formula (I), wherein
A is

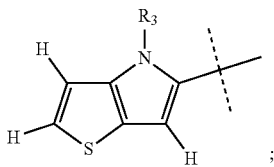

R is $L^1$-$R^5$;
$R^1$, $R^2$ are hydrogen;
$R_3$ is methyl;
$L^1$ is —$(CH_2)_j$—Y—
j is 2;
$R^5$ is phenyl substituted by one $L^2$-$R^6$ substituent;
$L^2$ is —$(CH_2)_n$—W—$(CH_2)_p$—;
n is 0;
p is 0 or 1;
W is oxygen;
or a stereoisomer or a pharmaceutically acceptable salt thereof.

In one embodiment, the application pertains to a compound of formula (I), wherein $R^6$ is piperidinyl or pyrrolidinyl.

In one embodiment, the application pertains to a compound of formula (I), wherein the compounds is selected from the group consisting of:
  1H-indol-3-yl-(4-methylthieno[3,2-b]pyrrol-5-yl)methanone;
  (5-methyl-1H-indol-3-yl)-(4-methylthieno[3,2-b]pyrrol-5-yl)methanone;
  (5-ethyl-1H-indol-3-yl)-(4-methylthieno[3,2-b]pyrrol-5-yl)methanone;
  (5-bromo-1H-indol-3-yl)-(4-methylthieno[3,2-b]pyrrol-5-yl)methanone;
  (4-ethylthieno[3,2-b]pyrrol-5-yl)-(1H-indol-3-yl)methanone;
  1H-indol-3-yl-(6-methylthieno[2,3-b]pyrrol-5-yl)methanone;
  (1-methylindol-3-yl)-(4-methylthieno[3,2-b]pyrrol-5-yl)methanone;
  [1-(2-methoxyethyl)indol-3-yl]-(4-methylthieno[3,2-b]pyrrol-5-yl)methanone;
  (4-methylthieno[3,2-b]pyrrol-5-yl)-[1-(2-phenoxyethyl)indol-3-yl]methanone;
  (4-methylthieno[3,2-b]pyrrol-5-yl)-[1-[2-[2-(pyrrolidin-3-ylmethoxy)phenoxy]ethyl]indol-3-yl]methanone;
  (4-methylthieno[3,2-b]pyrrol-5-yl)-[1-[2-[3-(pyrrolidin-3-ylmethoxy)phenoxy]ethyl]indol-3-yl]methanone;
  (4-methylthieno[3,2-b]pyrrol-5-yl)-[1-[2-[3-[[(3S)-pyrrolidin-3-yl]methoxy]phenoxy]ethyl]indol-3-yl]methanone;
  (4-methylthieno[3,2-b]pyrrol-5-yl)-[1-[2-[3-[[(3R)-pyrrolidin-3-yl]methoxy]phenoxy]ethyl]indol-3-yl]methanone;
  (4-methylthieno[3,2-b]pyrrol-5-yl)-[1-[2-[4-(pyrrolidin-3-ylmethoxy)phenoxy]ethyl]indol-3-yl]methanone;
  (4-methylthieno[3,2-b]pyrrol-5-yl)-[1-[2-[3-(4-piperidyloxy)phenoxy]ethyl]indol-3-yl]methanone;
  (4-methylthieno[3,2-b]pyrrol-5-yl)-[1-[2-[4-(4-piperidyloxy)phenoxy]ethyl]indol-3-yl]methanone;
  (4-methylthieno[3,2-b]pyrrol-5-yl)-[1-[2-[3-(4-piperidylmethoxy)phenoxy]ethyl]indol-3-yl]methanone;
  (4-methylthieno[3,2-b]pyrrol-5-yl)-[1-[2-[4-(4-piperidylmethoxy)phenoxy]ethyl]indol-3-yl]methanone;
  [1-[2-[3-(azepan-4-yloxy)phenoxy]ethyl]indol-3-yl]-(4-methylthieno[3,2-b]pyrrol-5-yl)methanone;
  [1-[2-[4-(azepan-4-yloxy)phenoxy]ethyl]indol-3-yl]-(4-methylthieno[3,2-b]pyrrol-5-yl)methanone;
  (4-methylthieno[3,2-b]pyrrol-5-yl)-[1-[3-[4-(pyrrolidin-3-ylmethoxy)phenyl]propyl]indol-3-yl]methanone;
  (4-methylthieno[3,2-b]pyrrol-5-yl)-[1-[3-[4-(4-piperidylmethoxy)phenyl]propyl]indol-3-yl]methanone;
  (4-methylthieno[3,2-b]pyrrol-5-yl)-[1-[3-[4-(4-piperidyloxy)phenyl]propyl]indol-3-yl]methanone;
  [1-[3-[4-(azepan-4-yloxy)phenyl]propyl]indol-3-yl]-(4-methylthieno[3,2-b]pyrrol-5-yl)methanone;
  [1-[3-[3,4-bis(4-piperidylmethoxy)phenyl]propyl]indol-3-yl]-(4-methylthieno[3,2-b]pyrrol-5-yl)methanone;
  (4-ethylthieno[3,2-b]pyrrol-5-yl)-[1-[3-[4-(4-piperidyloxy)phenyl]propyl]indol-3-yl]methanone;
  (4-ethylthieno[3,2-b]pyrrol-5-yl)-[1-[3-[4-(pyrrolidin-3-ylmethoxy)phenyl]propyl]indol-3-yl]methanone;
  (6-methylthieno[2,3-b]pyrrol-5-yl)-[1-[3-[4-(pyrrolidin-3-ylmethoxy)phenyl]propyl]indol-3-yl]methanone;
  (6-methylthieno[2,3-b]pyrrol-5-yl)-[1-[3-[4-(4-piperidyloxy)phenyl]propyl]indol-3-yl]methanone;
  [5-ethyl-1-[3-[4-(4-piperidyloxy)phenyl]propyl]indol-3-yl]-(4-methylthieno[3,2-b]pyrrol-5-yl)methanone; and
  [5-methyl-1-[3-[4-(4-piperidyloxy)phenyl]propyl]indol-3-yl]-(4-methylthieno[3,2-b]pyrrol-5-yl)methanone;
or a stereoisomer or a pharmaceutically acceptable salt thereof.

In one embodiment, the application pertains to a pharmaceutical composition comprising a compound of formula (I) together with a pharmaceutically acceptable excipient and/or diluent.

In one embodiment, the application pertains to a pharmaceutical composition comprising a compound of formula (I) together with a pharmaceutically acceptable excipient and/or diluent, further comprising at least one therapeutic agent, preferably selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent.

In one embodiment, the application pertains to a pharmaceutical composition comprising a compound of formula (I) together with a pharmaceutically acceptable excipient and/or diluent in the form of tablets, capsules, oral preparations, powders, granules, pills, injectable or infusible liquid, solutions, suspensions, emulsions, suppositories, ointments, creams, lotions, gels, pastes, or transdermal delivery devices.

In one embodiment, the application pertains to a pharmaceutical composition comprising a compound of formula (I) together with a pharmaceutically acceptable excipient and/or diluent, further comprising at least one therapeutic agent, preferably selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent, in the form of tablets, capsules, oral preparations, powders, granules, pills, injectable or infusible liquid, solutions, suspensions, emulsions, suppositories, ointments, creams, lotions, gels, pastes, or transdermal delivery devices.

In one embodiment, the application pertains to a compound of formula (I) for use as a medicament.

In one embodiment, the application pertains to a compound of formula (I) for use in the treatment and/or prevention of cancer, infectious diseases or a disease characterized by aberration of cellular energy metabolism, such as obesity.

In one embodiment, the application pertains to a compound of formula (I) for use in the treatment and/or prevention of leukemia, non-small cell lung cancer, hepatocellular carcinoma, or glioblastomas.

In one embodiment, the application pertains to a compound of formula (I) for use in the treatment of leukemia, non-small cell lung cancer, hepatocellular carcinoma, or glioblastomas.

In one embodiment, the application pertains to a compound of formula (I) for use in the prevention of leukemia, non-small cell lung cancer, hepatocellular carcinoma, or glioblastomas.

In one embodiment, the application pertains to a method of treating and/or preventing cancer, infectious diseases or a disease characterized by aberration of cellular energy metabolism, such as obesity, comprising administering a therapeutically effective amount of a compound of formula (I), or a stereoisomer or pharmaceutically acceptable salt thereof, to a subject in need thereof.

In one embodiment, the application pertains to a method of treating cancer, infectious diseases or a disease characterized by aberration of cellular energy metabolism, such as obesity, comprising administering a therapeutically effective amount of a compound of formula (I), or a stereoisomer or pharmaceutically acceptable salt thereof, to a subject in need thereof.

In one embodiment, the application pertains to a method of preventing cancer, infectious diseases or a disease characterized by aberration of cellular energy metabolism, such as obesity, comprising administering a therapeutically effective amount of a compound of formula (I), or a stereoisomer or pharmaceutically acceptable salt thereof, to a subject in need thereof.

In one embodiment, the application pertains to a method of treating and/or preventing leukemia, non-small cell lung cancer, hepatocellular carcinoma, or glioblastomas comprising administering a therapeutically effective amount of a compound of formula (I), or a stereoisomer or pharmaceutically acceptable salt thereof, to a subject in need thereof.

In one embodiment, the application pertains to a method of treating leukemia, non-small cell lung cancer, hepatocellular carcinoma, or glioblastomas comprising administering a therapeutically effective amount of a compound of formula (I), or a stereoisomer or pharmaceutically acceptable salt thereof, to a subject in need thereof.

In one embodiment, the application pertains to a method of preventing leukemia, non-small cell lung cancer, hepatocellular carcinoma, or glioblastomas comprising administering a therapeutically effective amount of a compound of formula (I), or a stereoisomer or pharmaceutically acceptable salt thereof, to a subject in need thereof.

In one embodiment, the application pertains to a method of treating and/or preventing acute myeloid leukemia comprising administering a therapeutically effective amount of a compound of formula (I), or a stereoisomer or pharmaceutically acceptable salt thereof, to a subject in need thereof.

In one embodiment, the application pertains to a method of treating acute myeloid leukemia comprising administering a therapeutically effective amount of a compound of formula (I), or a stereoisomer or pharmaceutically acceptable salt thereof, to a subject in need thereof.

In one embodiment, the application pertains to a method of preventing acute myeloid leukemia comprising administering a therapeutically effective amount of a compound of formula (I), or a stereoisomer or pharmaceutically acceptable salt thereof, to a subject in need thereof.

In one embodiment, the application pertains to a method of treating cancer, infectious diseases or a disease characterized by aberration of cellular energy metabolism, such as obesity, comprising administering a therapeutically effective amount of a compound of formula (I), or a stereoisomer or pharmaceutically acceptable salt thereof, to a subject in need thereof, further comprising administering a therapeutically effective amount of at least one therapeutic agent, preferably selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent.

In one embodiment, the application pertains to a method of preventing cancer, infectious diseases or a disease characterized by aberration of cellular energy metabolism, such as obesity, comprising administering a therapeutically effective amount of a compound of formula (I), or a stereoisomer or pharmaceutically acceptable salt thereof, to a subject in need thereof, further comprising administering a therapeutically effective amount of at least one therapeutic agent, preferably selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent.

In one embodiment, the application pertains to a method of treating leukemia (e.g., acute myeloid leukemia), non-small cell lung cancer, hepatocellular carcinoma, or glioblastomas comprising administering a therapeutically effective amount of a compound of formula (I), or a stereoisomer or pharmaceutically acceptable salt thereof, to a subject in need thereof, further comprising administering a therapeutically effective amount of at least one therapeutic agent, preferably selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent.

In one embodiment, the application pertains to a method of preventing leukemia (e.g., acute myeloid leukemia), non-small cell lung cancer, hepatocellular carcinoma, or glioblastomas comprising administering a therapeutically effective amount of a compound of formula (I), or a stereoisomer or pharmaceutically acceptable salt thereof, to a subject in need thereof, further comprising administering a therapeutically effective amount of at least one therapeutic agent, preferably selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent.

In one embodiment, the application pertains to a process for obtaining a compound of formula (I), wherein R is hydrogen, the process comprising the preparation of the acyl chloride of formula A2 by reaction of the carboxylic acid of formula A1 with thionyl chloride, and the preparation of the indole anion A4 by reaction of indole A3 with methyl magnesium bromide, and the condensation of the acyl chloride of formula A2 with indole anion A4 to obtain a compound of formula (I), as represented below:

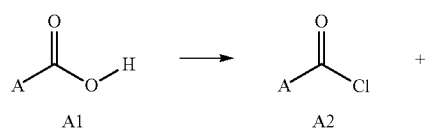

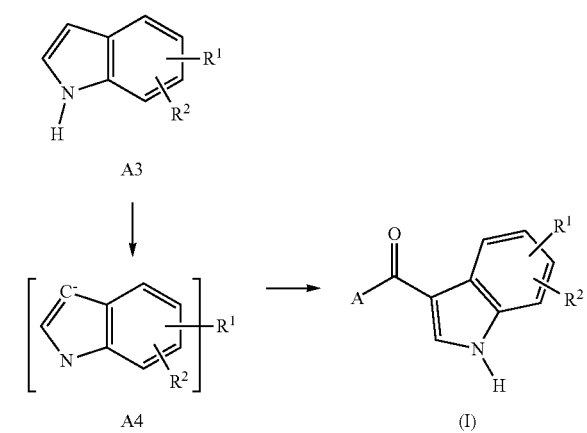

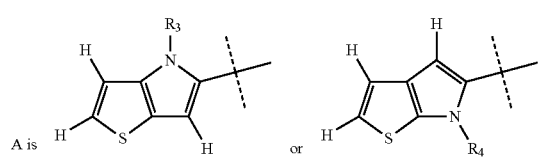

wherein A, $R^1$, $R^2$, $R_3$, and $R_4$ are as defined in the application.

In one embodiment, the application pertains to a process for obtaining a compound of formula (I) according to claim 1, wherein R is $L^1$-$R^5$, the process comprising the reaction of a compound of formula B1 with a compound of formula B2 in presence of a base, as represented below:

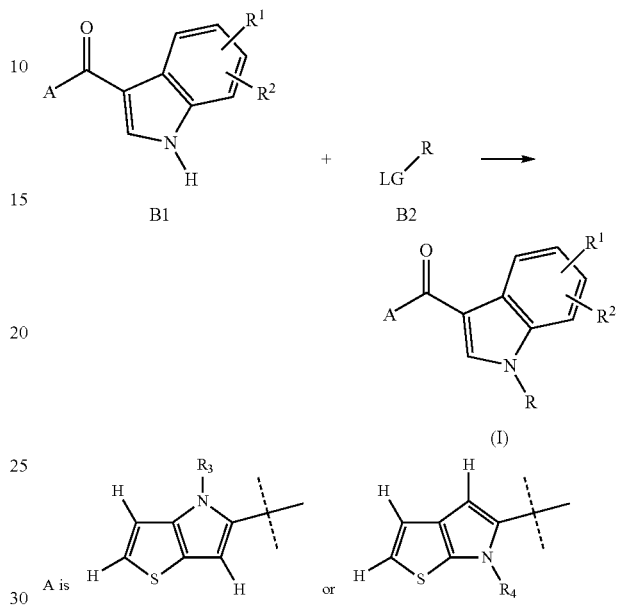

wherein R is $L^1$-$R^5$, and A, $R^1$, $R^2$, $R_3$, $R_4$, $L^1$, and $R^5$ are as defined in the application, and LG is a leaving group.

In one embodiment, the application pertains to a process for obtaining a compound of formula (I) according to claim 1, wherein R is $L^1$-$R^5$, the process comprising the reaction of a compound of formula B1 with a compound of formula B2 in presence of a base, as represented below:

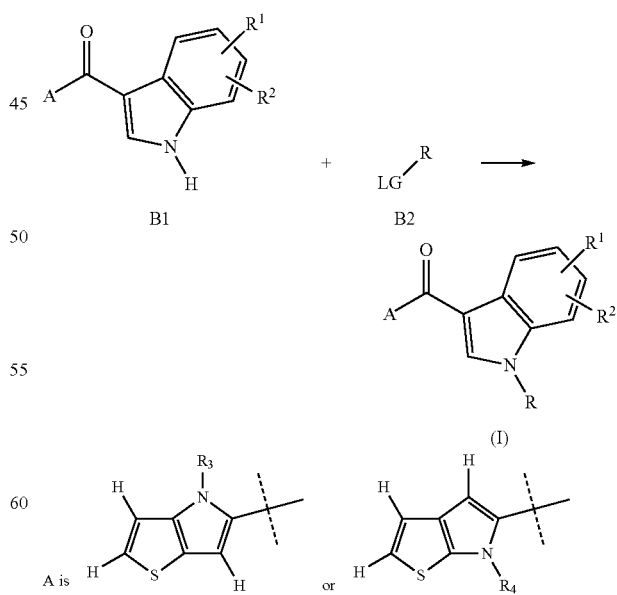

wherein R is $L^1$-$R^5$, and A, $R^1$, $R^2$, $R_3$, $R_4$, $L^1$, and $R^5$ are as defined in the application, and LG is bromine.

DETAILED DESCRIPTION

The present application relates to substituted indole derivatives having highly potent inhibitory activities of the KDM1A enzyme and selective over monoamine oxidases (MAOs), useful in the prevention or therapy of diseases and conditions associated with the activity of the histone demethylases.

According to the present application there are provided compounds of general formula (I):

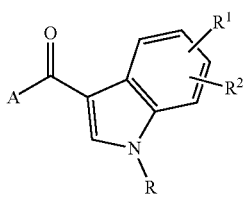
(I)

wherein
A is

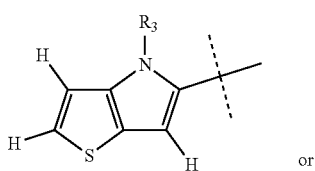
or
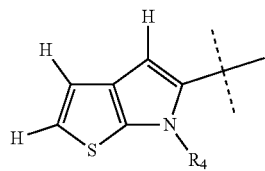

R is hydrogen or $L^1$-$R^5$;
$R^1$, $R^2$ are independently, hydrogen, OH, $C_1$-$C_4$-alkyl, $C_3$-$C_7$ cycloalkyl, aryl, or heteroaryl;
$R_3$, $R_4$ are hydrogen or $C_1$-$C_4$-alkyl;
$L^1$ is a bond, —$(CH_2)_j$—Y— or —$(CH_2)_k$—,
j is an integer from 2 to 6 (e.g. 2, 3, 4, 5 or 6);
k is an integer from 1 to 6 (e.g. 1, 2, 3, 4, 5 or 6);
Y is oxygen;
$R^5$ is $C_1$-$C_4$-alkyl or aryl, wherein the aryl is optionally substituted by one or two substituents chosen from halogen, $C_1$-$C_6$-alkyl, or $L^2$-$R^6$;
$L^2$ is —$(CH_2)_m$— or —$(CH_2)_n$—W—$(CH_2)_p$—;
$R^6$ is heterocyclyl, wherein the heterocyclyl is optionally substituted by $C_1$-$C_6$-alkyl;
m, n, p are, independently, zero or an integer from 1 to 6 (e.g. 1, 2, 3, 4, 5 or 6);
W is oxygen, NH, or $CH_2$;
or a stereoisomer or a pharmaceutically acceptable salt thereof.

In one embodiment, A is

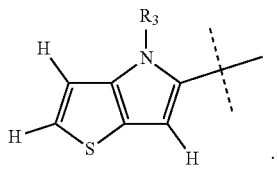

In one embodiment, A is

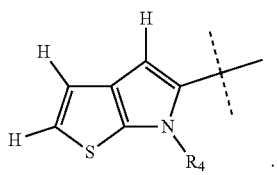

In one embodiment, $R_3$ or $R_4$ are methyl or ethyl.
In one embodiment:
R is hydrogen or $L^1$-$R^5$;
$R^1$, $R^2$ are independently, hydrogen, OH, or $C_1$-$C_4$-alkyl;
$R_3$, $R_4$ are methyl or ethyl;
$L^1$ is a bond, —$(CH_2)_2$—Y— or —$(CH_2)_k$—;
k is an integer from 1 to 4 (e.g. 1, 2, 3 or 4);
Y is oxygen;
$R^5$ is $C_1$-$C_4$-alkyl or phenyl substituted by one or two substituents chosen from $L^2$-$R^6$;
$L^2$ is —W—$(CH_2)_p$—;
$R^6$ is heterocyclyl, wherein the heterocyclyl is optionally substituted by $C_1$-$C_6$-alkyl;
p is zero or 1;
W is oxygen;
or a stereoisomer or a pharmaceutically acceptable salt thereof.

In one embodiment, R is hydrogen.
In one embodiment, R is $L^1$-$R^5$.
In one embodiment, $R^1$ and $R^2$ are both hydrogen.
In one embodiment, $R^1$ and $R^2$ are both methyl.
In one embodiment, $R^1$ and $R^2$ are independently hydrogen or C1-C4-alkyl.
In one embodiment, $R^1$ and $R^2$ are independently hydrogen or methyl.
In one embodiment, $L^1$ is —(CH2)j-Y— or —(CH2)k-.
In one embodiment, $L^1$ is —(CH2)j-Y—.
In one embodiment, $L^1$ is —(CH2)k-.
In one embodiment, j is 2, 3, 4, or 5.
In one embodiment, j is 2.
In one embodiment, j is 3.
In one embodiment, j is 4.
In one embodiment, j is 5.
In one embodiment, k is 1, 2, 3, 4, or 5.
In one embodiment, k is 1.
In one embodiment, k is 2.
In one embodiment, k is 3.
In one embodiment, k is 4.
In one embodiment, k is 5.
In one embodiment, $R^5$ is methyl, or phenyl substituted by one or two substituents chosen from $L^2$-$R^6$.
In one embodiment, $R^5$ is methyl.
In one embodiment, $R^5$ is phenyl substituted by one or two substituents chosen from $L^2$-$R^6$.

In one embodiment, $R^5$ is phenyl substituted by one substituent chosen from $L^2$-$R^6$.

In one embodiment, $R^5$ is phenyl substituted by two substituents each chosen from $L^2$-$R^6$.

In one embodiment, $L^2$ is —(CH2)m-.
In one embodiment, $L^2$ is —(CH2)n-W—(CH2)p-.
In one embodiment, W is oxygen.
In one embodiment, W is NH.
In one embodiment, W is $CH_2$.
In one embodiment, m is 0, 1, 2, 3, 4, or 5.
In one embodiment, m is 0.
In one embodiment, m is 1.
In one embodiment, m is 2.
In one embodiment, m is 3.
In one embodiment, m is 4.
In one embodiment, m is 5.
In one embodiment, n is 0, 1, 2, 3, 4, or 5.
In one embodiment, n is 0.
In one embodiment, n is 1.
In one embodiment, n is 2.
In one embodiment, n is 3.
In one embodiment, n is 4.
In one embodiment, n is 5.
In one embodiment, p is 0, 1, 2, 3, 4, or 5.
In one embodiment, p is 0.
In one embodiment, p is 1.
In one embodiment, p is 2.
In one embodiment, p is 3.
In one embodiment, p is 4.
In one embodiment, p is 5.

In one embodiment, $R^6$ is pyrrolidyl, pyrrolidinyl, piperidyl, piperidinyl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydro-benzodioxinyl, benzoxazolyl, azetidyl, azepinyl, and diazapinyl, optionally substituted by $C_1$-$C_6$-alkyl.

In one embodiment, $R^6$ is piperidinyl or pyrrolidinyl, optionally substituted by $C_1$-$C_6$-alkyl.

In one embodiment, $R^6$ is piperidinyl, optionally substituted by $C_1$-$C_6$-alkyl.

In one embodiment, $R^6$ is pyrrolidinyl, optionally substituted by $C_1$-$C_6$-alkyl.

In one embodiment, $R^6$ is unsubstituted piperidinyl.
In one embodiment, $R^6$ is unsubstituted pyrrolidinyl.

Compounds of general formula (I) include:
1H-indol-3-yl-(4-methylthieno[3,2-b]pyrrol-5-yl)methanone;
(5-methyl-1H-indol-3-yl)-(4-methylthieno[3,2-b]pyrrol-5-yl)methanone;
(5-ethyl-1H-indol-3-yl)-(4-methylthieno[3,2-b]pyrrol-5-yl)methanone;
(5-bromo-1H-indol-3-yl)-(4-methylthieno[3,2-b]pyrrol-5-yl)methanone;
(4-ethylthieno[3,2-b]pyrrol-5-yl)-(1H-indol-3-yl)methanone;
1H-indol-3-yl-(6-methylthieno[2,3-b]pyrrol-5-yl)methanone;
(1-methylindol-3-yl)-(4-methylthieno[3,2-b]pyrrol-5-yl)methanone;
[1-(2-methoxyethyl)indol-3-yl]-(4-methylthieno[3,2-b]pyrrol-5-yl)methanone;
(4-methylthieno[3,2-b]pyrrol-5-yl)-[1-(2-phenoxyethyl)indol-3-yl]methanone;
(4-methylthieno[3,2-b]pyrrol-5-yl)-[1-[2-[2-(pyrrolidin-3-ylmethoxy)phenoxy]ethyl]indol-3-yl]methanone;
(4-methylthieno[3,2-b]pyrrol-5-yl)-[1-[2-[3-(pyrrolidin-3-ylmethoxy)phenoxy]ethyl]indol-3-yl]methanone;
(4-methylthieno[3,2-b]pyrrol-5-yl)-[1-[2-[3-[[(3S)-pyrrolidin-3-yl]methoxy]phenoxy]ethyl]indol-3-yl]methanone;
(4-methylthieno[3,2-b]pyrrol-5-yl)-[1-[2-[3-[[(3R)-pyrrolidin-3-yl]methoxy]phenoxy]ethyl]indol-3-yl]methanone;
(4-methylthieno[3,2-b]pyrrol-5-yl)-[1-[2-[4-(pyrrolidin-3-ylmethoxy)phenoxy]ethyl]indol-3-yl]methanone;
(4-methylthieno[3,2-b]pyrrol-5-yl)-[1-[2-[3-(4-piperidyloxy)phenoxy]ethyl]indol-3-yl]methanone;
(4-methylthieno[3,2-b]pyrrol-5-yl)-[1-[2-[4-(4-pipendyloxy)phenoxy]ethyl]indol-3-yl]methanone;
(4-methylthieno[3,2-b]pyrrol-5-yl)-[1-[2-[3-(4-piperidylmethoxy)phenoxy]ethyl]indol-3-yl]methanone;
(4-methylthieno[3,2-b]pyrrol-5-yl)-[1-[2-[4-(4-piperidylmethoxy)phenoxy]ethyl]indol-3-yl]methanone;
[1-[2-[3-(azepan-4-yloxy)phenoxy]ethyl]indol-3-yl]-(4-methylthieno[3,2-b]pyrrol-5-yl)methanone;
[1-[2-[4-(azepan-4-yloxy)phenoxy]ethyl]indol-3-yl]-(4-methylthieno[3,2-b]pyrrol-5-yl)methanone;
(4-methylthieno[3,2-b]pyrrol-5-yl)-[1-[3-[4-(pyrrolidin-3-ylmethoxy)phenyl]propyl]indol-3-yl]methanone;
(4-methylthieno[3,2-b]pyrrol-5-yl)-[1-[3-[4-(4-piperidylmethoxy)phenyl]propyl]indol-3-yl]methanone;
(4-methylthieno[3,2-b]pyrrol-5-yl)-[1-[3-[4-(4-piperidyloxy)phenyl]propyl]indol-3-yl]methanone;
[1-[3-[4-(azepan-4-yloxy)phenyl]propyl]indol-3-yl]-(4-methylthieno[3,2-b]pyrrol-5-yl)methanone;
[1-[3-[3,4-bis(4-piperidylmethoxy)phenyl]propyl]indol-3-yl]-(4-methylthieno[3,2-b]pyrrol-5-yl)methanone;
(4-ethylthieno[3,2-b]pyrrol-5-yl)-[1-[3-[4-(4-piperidyloxy)phenyl]propyl]indol-3-yl]methanone;
(4-ethylthieno[3,2-b]pyrrol-5-yl)-[1-[3-[4-(pyrrolidin-3-ylmethoxy)phenyl]propyl]indol-3-yl]methanone;
(6-methylthieno[2,3-b]pyrrol-5-yl)-[1-[3-[4-(pyrrolidin-3-ylmethoxy)phenyl]propyl]indol-3-yl]methanone;
(6-methylthieno[2,3-b]pyrrol-5-yl)-[1-[3-[4-(4-piperidyloxy)phenyl]propyl]indol-3-yl]methanone;
[5-ethyl-1-[3-[4-(4-piperidyloxy)phenyl]propyl]indol-3-yl]-(4-methylthieno[3,2-b]pyrrol-5-yl)methanone;
[5-methyl-1-[3-[4-(4-piperidyloxy)phenyl]propyl]indol-3-yl]-(4-methylthieno[3,2-b]pyrrol-5-yl)methanone;
4-methylthieno[3,2-b]pyrrol-5-yl)-[1-[2-[4-(4-piperidylmethoxy)phenyl]ethyl]indol-3-yl]methanone hydrochloride;
(4-methylthieno[3,2-b]pyrrol-5-yl)-[1-[2-[4-(4-piperidyloxy)phenyl]ethyl]indol-3-yl]methanone hydrochloride;
(4-methylthieno[3,2-b]pyrrol-5-yl)-[1-[2-[4-[2-(4-piperidyl)ethoxy]phenyl]ethyl]indol-3-yl]methanone hydrochloride;

or stereoisomers or pharmaceutically acceptable salts thereof.

In another embodiment, the application provides the compounds of general formula (I) for use as medicament.

In another embodiment, the application provides the compounds of general formula (I) for the use in the treatment and/or prevention of cancer, infectious diseases or a disease characterized by aberration of cellular energy metabolism, such as obesity. Preferably, the compounds of general formula (I) are for the use in the treatment and/or prevention of leukemia (e.g., acute myeloid leukemia), non-small cell lung cancer, hepatocellular carcinoma, or glioblastomas. Still preferably the glioblastomas are giant cell glioblastoma or gliosarcoma.

In another embodiment, the application provides for the use of a therapeutically effective amount of a compound of general formula (I) and a therapeutically effective amount of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent for treating and/or preventing cancer (e.g., leukemia, non-small cell lung cancer, hepatocellular carcinoma, or glioblastomas such as giant cell glioblastoma or gliosarcoma), infectious diseases, or a disease characterized by aberration of cellular energy metabolism, such as obesity.

In another embodiment, the application provides for the use of a therapeutically effective amount of a compound of general formula (I) and a therapeutically effective amount of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent for treating cancer (e.g., leukemia, non-small cell lung cancer, hepatocellular carcinoma, or glioblastomas such as giant cell glioblastoma or gliosarcoma), infectious diseases, or a disease characterized by aberration of cellular energy metabolism, such as obesity.

In another embodiment, the application provides for the use of a therapeutically effective amount of a compound of general formula (I) and a therapeutically effective amount of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent for preventing cancer (e.g., leukemia, non-small cell lung cancer, hepatocellular carcinoma, or glioblastomas such as giant cell glioblastoma or gliosarcoma), infectious diseases, or a disease characterized by aberration of cellular energy metabolism, such as obesity.

A further embodiment of the application is a pharmaceutical composition comprising a compound of general formula (I), together with a pharmaceutically acceptable excipient and/or diluent A further embodiment of the application is a pharmaceutical composition comprising a compound of general formula (I), together with a pharmaceutically acceptable excipient and/or diluent, further comprising at least one further therapeutic agent, preferably selected from the group consisting of histone deacetylase inhibitors, retinoid receptor modulators, anti-proliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors or a chemotherapeutic agent.

A further embodiment of the application is a method of treating and/or preventing cancer, infectious diseases or a disease characterized by aberration of cellular energy metabolism, such as obesity, comprising administering a therapeutically effective amount of a compound of formula (I), or a stereoisomer or pharmaceutically acceptable salt thereof, to a subject in need thereof.

A further embodiment of the application is a method of treating and/or preventing leukemia (e.g., acute myeloid leukemia), non-small cell lung cancer, hepatocellular carcinoma, or glioblastomas comprising administering a therapeutically effective amount of a compound of formula (I), or a stereoisomer or pharmaceutically acceptable salt thereof, to a subject in need thereof.

In the present application, "aryl" includes groups with aromaticity, including "conjugated," or multicyclic systems with one or more aromatic rings and do not contain any heteroatom in the ring structure. Examples include phenyl, naphthalenyl, etc. The term "arylene" refers to the corresponding divalent groups, such as phenylene. In one embodiment, "aryl" represents a mono or bicyclic aromatic ring system of 6 atoms, or 9 or 10 atoms, respectively. Examples of such an aryl are phenyl, indenyl, indanyl and naphthyl and tetrahydronaphthalenyl. Substituted aryl means that the hydrogen atoms on independently each carbon atom may be independently replaced by a substituent as defined herein above.

In the present application, "heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable aromatic heterocyclic ring, such as a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g.,1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)p, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. The term "heteroarylene" refers to the corresponding divalent groups.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthyridine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, e.g., alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

"Heterocyclyl" represents a mono, bicyclic or a spirocyclic saturated or partially saturated non-aromatic ring system of 4 to 12 members (e.g. 4, 5, 6, 7, 8, 9, 10, 11 or 12 members), which contains one, two, or three heteroatoms selected from nitrogen, oxygen, and sulphur and three to eleven carbon atoms (e.g. 3, 4, 5, 6, 7, 8, 9, 10 or 11 carbon atoms). Examples of such heterocycles include, but are not limited to: pyrrolidyl, pyrrolidinyl, piperidyl, piperidinyl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydro-benzodioxinyl, benzoxazolyl, azetidyl, azepinyl, and diazapinyl.

The term "$C_1$-$C_6$ alkyl" refers to a straight or branched hydrocarbon chain radical, consisting solely of carbon and hydrogen atoms, having from one to six carbon atoms. This term encompasses straight or branched hydrocarbon chain radicals, consisting solely of carbon and hydrogen atoms, having 1, 2, 3, 4, 5 or 6 carbon atoms. The "$C_1$-$C_6$ alkyl" group is preferably a linear or branched $C_1$-$C_4$ alkyl group, more preferably a $C_1$-$C_2$ alkyl group. Suitable examples of $C_1$-$C_6$ alkyl include methyl, ethyl, n-propyl, isopropyl, butyl, tert-butyl, pentyl, and hexyl. The term "$C_1$-$C_4$ alkyl" refers to a straight or branched hydrocarbon chain radical, consisting solely of carbon and hydrogen atoms, having from one to four carbon atoms. This term encompasses straight or branched hydrocarbon chain radicals, consisting solely of carbon and hydrogen atoms, having 1, 2, 3 or 4 carbon atoms.

The term "$C_{3-7}$ cycloalkyl" refers to a saturated monocyclic hydrocarbon ring system having three to seven carbon atoms. This term encompasses saturated monocyclic hydrocarbon ring systems having 3, 4, 5, 6 or 7 carbon atoms. Suitable examples of $C_{3-6}$-cycloalkyl groups include cyclopropyl, cyclobutyl, cyclopentyl, and cyclohexyl.

The term "halogen" refers to fluoro, chloro, bromo, or iodo. "Halogens" are preferably fluorine, chlorine or bromine, being in particular fluorine or chlorine.

The term "Leaving group" refers to halogen, preferably to chloride, bromide or iodide.

The phrase "reversible inhibitor" refers to an inhibiting molecular entity that interacts with an enzyme by non-covalent interactions and is able to associate/dissociate to the enzyme.

Pharmaceutically acceptable salts comprise conventional non-toxic salts obtained by salification of a compound of formula (I) with inorganic acids (e.g. hydrochloric, hydrobromic, sulphuric, or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc, New York 1996, Volume 13, page 453-497. Other salts, which are not pharmaceutically acceptable, e.g., the trifluoroacetate salt, may be useful in the preparation of compounds of this application and these form a further aspect of the application. The application includes within its scope all possible stoichiometric and non-stoichiometric forms of the salts of the compounds of formula (I).

In addition, the compounds of formula (I) may exist in unsolvated as well as in solvated forms with pharmaceutically acceptable solvents such as water, EtOH and the like.

Certain compounds of formula (I) may exist in stereoisomeric forms (e.g. they may contain one or more asymmetric carbon atoms). The individual stereoisomers (enantiomers and diastereomers) and mixtures of these are included within the scope of the present application. The present application also covers the individual isomers of the compounds represented by formula (I) as mixtures with isomers thereof in which one or more chiral centres are inverted.

The application also includes all suitable isotopic variations of a compound of the application. Examples of isotopes that can be incorporated into compounds of the application include isotopes such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the application, e.g., those in which a radioactive isotope such as $^3H$ or $^{14}C$ is incorporated, are useful in drug and/or substrate tissue distribution studies. Further, substitution with isotopes such as deuterium $^2H$, may afford certain therapeutic advantages resulting from greater metabolic stability. Isotopic variations of the compounds of the application can generally be prepared by conventional procedures such as by the illustrative methods or by the preparations described in the examples hereafter using appropriate isotopic variations of suitable reagents.

It is a further embodiment of the application a process for obtaining a compound of formula (I) as defined above, wherein R is hydrogen, the process comprising the preparation of the acyl chloride of formula A2 by reaction of the carboxylic acid of formula A1 with thionyl chloride, and the preparation of the indole anion A4 by reaction of indole A3 with methyl magnesium bromide, and the condensation of the acyl chloride of formula A2 with indole anion A4 to obtain a compound of formula (I), as represented in Scheme A below:

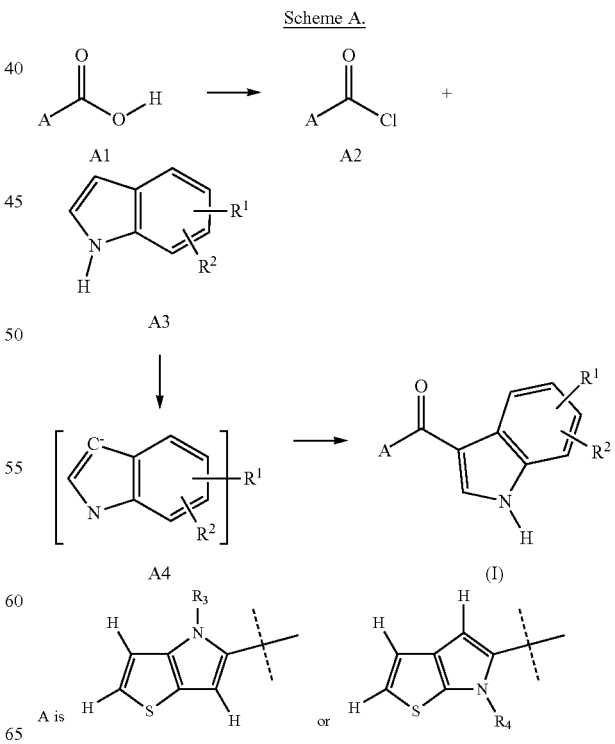

wherein A, $R^1$, $R^2$, $R_3$, and $R_4$ are as defined above.

Carboxylic acids of formula A1 are known compounds or can be prepared as described in PCT application WO2016/034946 starting from commercially available ethyl 4H-thieno[3,2-b]pyrrole-5-carboxylate (Fluorochem, Cat No. 067104) or ethyl 6H-thieno[2,3-b]pyrrole-5-carboxylate (Sigma Aldrich, cat. number PH011284). Indoles of formula A3 are known compounds.

The formation of the acyl chloride of formula A2 can be carried out in a suitable solvent such as polar aprotic solvents, for instance, tetrahydrofuran, 1,4-dioxane, dimethylformamide, dichloromethane, or mixtures thereof, at a temperature ranging from about 0° C. to reflux and for a time varying from about 30 minutes up to 96 hours. The formation of indole anion A4 can be carried out in a suitable solvent such as diethylether, preferably at a temperature ranging from about 0° C. to room temperature. Preferably, the reaction is carried out under nitrogen atmosphere. The coupling reaction of an acyl chloride of formula A2 with a compound of formula A4 is carried out in a suitable solvent such as diethylether at a temperature ranging from about 0° C. to reflux.

Alternatively, a compound of formula (I) can be obtained according to a Friedel-Crafts reaction by reaction of an acyl chloride of formula A2 with an indole of formula A3 in presence of a Lewis acid, for instance AlCl$_3$, ZrCl$_4$, or diethylaluminium chloride, in a suitable solvent, for instance hexane, dichloromethane, or mixtures thereof.

Compounds of formula (I), wherein R is L$^1$-R$^5$ and L$^1$ and R$^5$ are as defined above, can obtained by reaction of compounds of formula B1 with compounds of formula B2, wherein LG is a leaving group, for instance bromine, in a suitable solvent, for instance dimethylformamide or dimethylacetamide, and in presence of a base, for instance sodium hydride, at a temperature ranging from about 0° C. to reflux, as represented in Scheme B below:

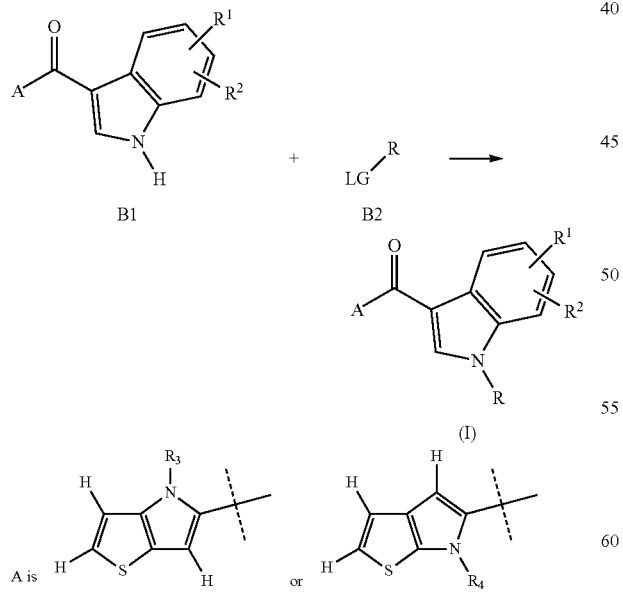

wherein R is L$^1$-R$^5$, and A, R$^1$, R$^2$, R$_3$, R$_4$, L$^1$, and R$^5$ are as defined above, and LG is a leaving group.

Compounds of formula B1 can be prepared as described in Scheme A. Compounds of formula B2 are known compounds or can be prepared by known methods. For instance a compound of formula C5, where LG and R$^6$ are as defined above, Y and L$^2$ are oxygen can be obtained by the reaction of a diol derivative of formula C1 with an alcohol of formula C2, that is carried out under the standard conditions of the Mitsunobu reaction, for instance by reaction with triphenylphosphine and diethylazodicarboxylate, at a temperature ranging from about 0° C. to 80° C., in a suitable solvent, such as tetrahydrofuran or toluene or dichloromethane, for a time varying from about 30 min up to 72 h, to give a compound of formula C3. Reaction of a compound of formula C3 with an alcohol of formula C4 under the standard condition of the Mitsunobu reaction provides the intermediate C5 as represented in Scheme C below:

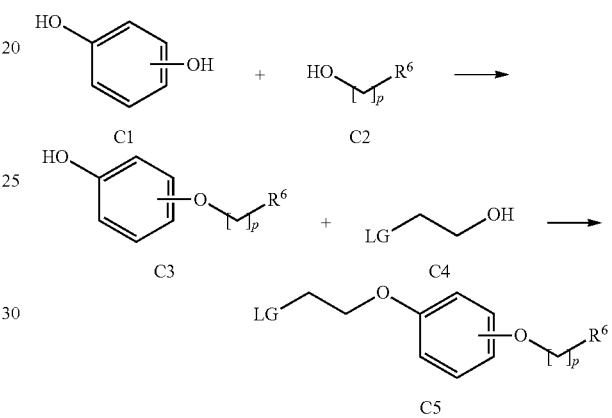

wherein p, R$^6$ and LG are as defined above.

Compounds of formula C1, C2, and C4 are known compounds or can be prepared by known methods.

Alternatively, reaction of a compound of formula D1 with an alcohol of formula D2 under the standard conditions of the Mitsunobu reaction provides the intermediate D3 as represented in Scheme D below:

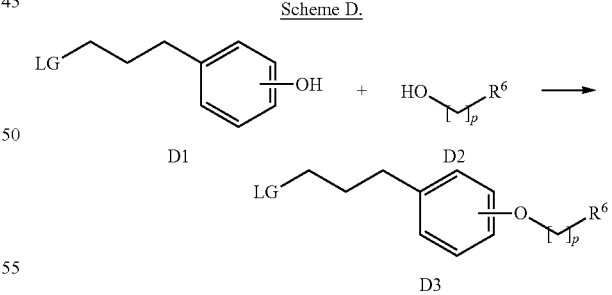

wherein p, R$^6$ and LG are as defined above.

Compounds of formula D1 and D2 are known compounds or can be prepared by known methods.

In the case it is necessary to protect a chemical group of a compound of the present application and/or an intermediate thereof, before carrying out one of the before described reactions, said chemical group can be protected and deprotected according to known methods. A thorough discussion for protection/deprotection steps is provided in Greene and Wuts (Greene, T. W.; Wuts, P. G. M. "Protective Groups in Organic Synthesis", John Wiley & Sons Inc., 2006) and in Kocienski (Kocienski, P. J. "Protecting Groups", George Thieme Verlag, 2005).

Salification of the compounds of formula (I), and preparation of compounds of formula (I), free of their salts, can be carried out by known conventional methods.

In view of the above described mechanisms of action, the compounds of the present application are useful in the prevention or treatment of tumor type diseases, including, but not limited to: acute myeloid leukaemia, chronic myeloid leukaemia, acute lymphoblastic leukaemia, chronic lymphoblastic leukaemia, myelodysplastic syndromes, multiple myeloma, Hodgkin's disease, non-Hodgkin's lymphomas, cutaneous and peripheral T-cell lymphoma, adult T-cell leukemia, large B-cell lymphoma; mammary tumors; pulmonary tumors and pleural mesotheliomas, adenocarcinoma, non-small lung cancer, small-cell lung cancer; skin tumors including basal cell carcinomas (basaliomas), melanomas, squamous cell carcinoma, Kaposi's sarcoma, keratocanthomas, osteosarcomas, fibrosarcomas, rhabdomyosarcomas, neuroblastomas, glioblastomas, cerebral tumors, head and neck cancer, testicular and ovarian tumors, cervical carcinoma, endometrial and prostate tumors (e.g., advanced prostate cancer), thyroid carcinomas (e.g., thyroid follicular cancer), colon cancers (e.g., colon adenocarcinoma, colon adenoma), gastric tumors and gastrointestinal adenocarcinomas, hepatocellular carcinomas, pancreatic carcinomas (e.g., exocrine pancreatic carcinoma), renal tumors, teratocarcinomas and embryonic carcinomas.

The compounds of the application are also useful in the prevention or treatment of infections, including, but not limited to: infections caused by protozoa, fungi, phytotoxic agents, viruses and parasites, e.g., HIV or herpes virus infections.

Furthermore, the compounds of the application are also useful in the prevention or treatment of obesity.

The term "therapeutically effective amount", as used herein, refers to an amount of formula (I), composition, or pharmaceutical composition thereof effective to treat or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

The compounds of formula (I), can also be used in combination with additional agents, in particular anti-tumor and differentiating agents, either by separate administrations, or by including the two active principles in the same pharmaceutical formulation. Non-exhaustive examples of suitable additional agents include:

a) histone deacetylase inhibitors (e.g., but not limited to: SAHA, PXD101, JNJ-26481585, SB939, ITF-2357, LBH589, PCI-24781, valproic acid, butyric acid, MS-275, MGCD0103 and FK-228);

b) retinoid receptor modulators such as 13-cis-retinoic acid, 9-cis-retinoic acid, bexarotene, alitretinoin, or tretinoin; vitamin D;

c) antiproliferative/antineoplastic drugs and combinations thereof, as used in medical oncology, such as alkylating agents (e.g., platin derivatives like cis-platin, carboplatin, oxaliplatin, lobaplatin, satraplatin, nedaplatin, heptaplatin; nitrogen mustard such as chlorambucil, melphalan, chlormethine, cyclophosphamide, ifosfamide, trofosfamide, uramustine, bendamustine, estramustine; busulphan, temozolomide or nitrosoureas); antimetabolites (e.g., antifolates such as aminopterin, methotrexate, pemetrexed, raltitrexed); purines such as cladribine, clofarabine, fludarabine, mercaptopurine, pentostatin, thioguanine; pyrimidines like capecitabine, cytarabine, fluorouracil, floxuridine, gemcitabine; azacitidine, decitabine; cytosine arabinoside or hydroxyurea; antitumour antibiotics (e.g., anthracyclines like aclarubicin, amrubicin, daunomycin, doxorubicin, epirubicin, idarabicin, valrubicin, zorubicine; mitoxantrone; or antibiotics from streptomyces like actinomycin, bleomycin, mitomycin, or plicamycin); antimitotic agents (e.g., vinca alkaloids like vincristine, vinblastine, vindesine or vinorelbine; taxoids like docetaxel, paclitaxel or tesetaxel; epothilones like ixabepilone) and topoisomerase inhibitors (e.g., epipodophyllotoxins like etoposide and teniposide; amsacrine, camptothecin, irinotecan, rubitecan, and topotecan);

d) cytostatic agents such as antioestrogens (e.g., but not limited to: tamoxifen, toremifene, raloxifene, droloxifene and idoxifene), oestrogen receptor down regulators (e.g., but not limited to: fulvestrant), antiandrogens (e.g., but not limited to: bicalutamide, flutamide, nilutamide, liarozole or cyproterone acetate), LHRH antagonists or LHRH agonists (e.g., but not limited to: goserelin, leuprorelin or buserelin), progestogens (e.g., but not limited to, megestrol acetate), aromatase inhibitors (e.g., but not limited to: anastrozole, letrozole, vorazole and exemestane) and inhibitors of 5-alpha-reductase such as finasteride;

e) agents which inhibit cancer cell invasion (e.g., metalloproteinase inhibitors and inhibitors of urokinase plasminogen activator receptor function);

f) inhibitors of growth factor function, e.g., growth factor antibodies, growth factor receptor antibodies (e.g., but not limited to: the anti-erbb2 antibody trastuzumab, the anti-erbb1 antibody cetuximab and panitumumab, the anti IGF1R antibody figitumumab), farnesyl transferase inhibitors, MEK inhibitors, tyrosine kinase inhibitors and serine/threonine kinase inhibitors, e.g., enzastaurin, dasatinib, erlotinib, gefitinib, imatinib, lapatinib, nilotinib, sorafenib, sunitinib, everolimus, sirolimus or temsirolimus;

g) antiangiogenic agents such as those which inhibit the effects of vascular endothelial growth factor, e.g., the anti-vascular endothelial cell growth factor antibody bevacizumab, lenalidomide or thalidomide;

h) cell cycle inhibitors including, e.g., CDK inhibitors (e.g., but not limited to: flavopiridol, roscovitine) and other inhibitors of cell cycle checkpoints; inhibitors of aurora kinase and other kinases involved in mitosis and cytokinesis regulation;

i) proteasome inhibitors (e.g., but not limited to: lactacystin, bortezomib, epoxomicin);

j) HSP90 inhibitors (e.g., but not limited to: AT-13387, KOS-953, KOS-1022, CNF-1010, CNF-2024, SNX 5422, STA-9090, NVP-HSP990, NVP-AUY922, PU-H17 and XL-888)

k) Selective COX-2 inhibitors (e.g., but not limited to, celecoxib), or non-selective NSAIDs (e.g., but not limited to: diclofenac, flurbiprofen, ibuprofen, ketoprofen, or naproxen).

In another aspect, a compound of general formula (I) can be used in combination with radiation therapy. In yet another aspect, a compound of general formula (I) may be administered in combination with standard chemotherapy combinations such as, but not restricted to, CMF (cyclophosphamide, methotrexate and 5-fluorouracil), CAF (cyclophosphamide, doxorubicin and 5-fluorouracil), AC (doxorubicin and cyclophosphamide), FEC (5-fluorouracil, epirubicin, and cyclophosphamide), ACT or ATC (doxorubicin, cyclophosphamide, and paclitaxel), or CMFP (cyclophosphamide, methotrexate, 5-fluorouracil and prednisone).

The application also provides pharmaceutical compositions comprising one or more compounds of formula (I), and one or more pharmaceutically acceptable excipient and/or diluent. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable or infusible liquid, solutions, suspensions, emulsions, suppositories, ointments, creams, lotions, gels, pastes, or transdermal delivery devices.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (e.g., sodium lauryl sulfate).

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, e.g., aqueous or oily suspensions, solutions, emulsions, syrups or elixirs, or can be presented as a dry product for reconstitution with water or with a suitable vehicle before use. Such liquid preparations can contain conventional additives such as suspending agents, e.g., sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the application.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the application regards topical treatment. Topical formulations can contain, e.g., ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the application regards transdermal delivery. Typical transdermal formulations comprise conventional aqueous and non-aqueous vectors, such as creams, oils, lotions or pastes or can be in the form of membranes or medicated patches.

A reference for the formulations is the book by Remington ("Remington: The Science and Practice of Pharmacy", Lippincott Williams & Wilkins, 2000).

The compounds of the present application may be employed alone as a sole therapy or in combination with other therapeutic agents for the treatment of the above-mentioned conditions. The combination can be administered as separate compositions (simultaneous, sequential) of the individual components of the treatment or as a single dosage form containing both agents. When the compounds of this application are in combination with others active ingredients, the active ingredients may be separately formulated into single-ingredient preparations of one of the above-described forms and then provided as combined preparations, which are given at the same time or different times, or may be formulated together into a two- or more-ingredient preparation.

Compounds of general formula (I) may be administered to a patient in a total daily dose of, e.g., from 0.001 to 1000 mg/kg body weight daily. Dosage unit compositions may contain such amounts of submultiples thereof to make up the daily dose. The determination of optimum dosages for a particular patient is well known to one skilled in the art.

As is common practice, the compositions are normally accompanied by written or printed instructions for use in the treatment in question.

The following Examples are presented in order to further illustrate the application.

EXAMPLE 1

Chemical Synthesis

Unless otherwise indicated, commercially available reagents and solvents (HPLC grade) were used without further purification. Specifically, the following abbreviations may have been used in the descriptions of the experimental methods:

| | |
|---|---|
| NMR (Nuclear Magnetic Resonance) | $^1$H (proton) |
| MHz (Megahertz) | Hz (Hertz) |
| HPLC (High Performance Liquid Chromatography) | LC-MS (Liquid Chromatography Mass Spectrum) |
| s (seconds) | min (minutes) |
| h (hours) | mg (milligrams) |
| g (grams) | μL (microlitres) |
| mL (millilitres) | mmol (millimoles) |
| nm (nanometers) | μM (micromolar) |
| M (molarity) | RT (room temperature) |
| AcOH (acetic acid) | BOC or boc (tert-butyloxycarbonyl) |
| CBr$_4$ (carbon tetrabromide) | CDCl$_3$ (deuterated chloroform) |
| CH$_2$Cl$_2$ (dichloromethane) | Cs$_2$CO$_3$ (cesium carbonate) |
| CH$_3$CN (acetonitrile) | DIAD (diisopropyl azodicarboxylate) |
| DMA (dimethylacetamide) | DMF (dimethylformamide) |
| DMSO (dimethyl sulfoxide) | DMSO-d$_6$ (deuterated dimethyl sulfoxide) |
| DTT (dithiothreitol) | Et$_2$O (diethyl ether) |
| EtOAc (ethyl acetate) | EtOH (ethanol) |
| HCl (hydrochloric acid) | MAO A (monoamine oxidase A) |
| MAO B (monoamine oxidase B) | MeOH (methanol) |
| NaH (sodium hydride) | NaCl (sodium chloride) |
| NaHCO$_3$ (sodium bicarbonate) | Na$_2$SO$_4$ (sodium sulphate) |
| NH$_4$Cl (ammonium chloride) | Pd (palladium) |
| PPh$_3$ (triphenylphosphine) | SOCl$_2$ (thionyl chloride) |
| TBAF (tetra-n-butylammonium fluoride) | TBDMSCl (tert-butyldimethylchlorosilane) |
| THF (tetrahydrofuran) | Tris (tris(hydroxymethyl)aminomethane) |

Except where indicated otherwise, all temperatures are expressed in ° C. (degrees centigrade) or K (Kelvin).

The $^1$H-NMR spectra were acquired with a Varian 500 MHz instrument. The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet).

The LC-MS analyses were carried out on a Waters Acquity UPLC or Waters Acquity UPLC H-Class linked to with a SQD Single quadrupole (Waters) using an Acquity UPLC BEH C18 (50×2.1 mm, 1.7 μm) or Acquity UPLC HSS T3 (50×2.1 mm, 1.8 μm) column. Phase A was composed by either Milli-Q water/CH$_3$CN 95/5 (vol/vol)+0.07% formic acid (by volume) or Milli-Q water+0.07% formic acid (by volume); Phase B by CH$_3$CN+0.05% formic acid (by volume); flow rate: 0.6 mL/min; UV detection (DIODE array) from 210 to 400 nm; ESI+ detection in the 100-2000 m/z range. The yields were calculated assuming that products were 100% pure if not stated otherwise.

Intermediate 1: 4-Methylthieno[3,2-b]pyrrole-5-carboxylic acid

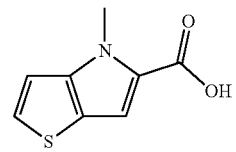

Ethyl 4-methylthieno[3,2-b]pyrrole-5-carboxylate 1.5 g (7.7 mmol) of ethyl 4H-thieno[3,2-b]pyrrole-5-carboxylate (Fluorochem, Cat No. 067104) was added at RT portion wise to a suspension of 0.46 g (12 mmol) of NaH in 35 mL of dry DMF. After stirring for 20 min at RT 3.3 g (23 mmol) of CH$_3$I was added in one portion and the mixture was stirred for additional 30 min. The reaction mixture was then poured into a saturated NH4Cl solution and extracted with Et$_2$O. The combined organic layers were dried over Na$_2$SO$_4$, filtered and the solvent evaporated to give 1.6 g of ethyl 4-methylthieno[3,2-b]pyrrole-5-carboxylate (99%) as a brown oil. $^1$H NMR (CDCl$_3$) δ (ppm): 7.34 (d, J=5.4 Hz, 1H), 7.20 (s, 1H), 6.95 (d, J=5.4 Hz, 1H), 4.34 (q, J=7.3 Hz, 2H), 4.07 (s, 3H), 1.39 (t, J=7.1 Hz, 3H); MS (ESI): m/z: 210 [M+H]$^+$

4-Methylthieno[3,2-b]pyrrole-5-carboxylate 0.92 g (38 mmol) of LiOH in 11 mL of H$_2$O was added at RT to a solution of 1.6 g (7.7 mmol) of ethyl 4-methyl-thieno[3,2-b]pyrrole-5-carboxylate in 11 mL of EtOH. The mixture was stirred for 30 min at reflux. The solvent was evaporated, then H$_2$O was added and the solution was brought to a pH value of about 2 with 2 M HCl. The mixture was extracted with EtOAc, the combined organic layers were dried over Na$_2$SO$_4$ and the solvent was evaporated to give 1.39 g of 4-methylthieno[3,2-b]pyrrole-5-carboxylate (99%) as a beige solid. $^1$H NMR (CDCl$_3$) δ (ppm): 12.45 (bs, 1H), 7.54 (d, J=5.4 Hz, 1H), 7.20 (d, J=5.4 Hz, 1H), 7.12 (s, 1H), 3.99 (s, 3H); MS (ESI): m/z: 182 [M+H]$^+$.

Intermediate 2: 4-Ethylthieno[3,2-b]pyrrole-5-carboxylic acid

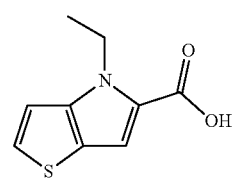

Ethyl 4-ethylthieno[3,2-b]pyrrole-5-carboxylate 1.00 g (5.12 mmol) of ethyl 4H-thieno[3,2-b]pyrrole-5-carboxylate was added at RT to a suspension of 0.31 g (7.7 mmol) of NaH in 50 mL of dry DMF. After stirring for 20 min at RT 2.39 g (15.4 mmol) of ethyl iodide was added and the mixture was stirred for further 30 min at RT. The reaction mixture was then poured into a saturated NH$_4$Cl solution and extracted with Et$_2$O. The combined organic layers were dried over Na$_2$SO$_4$ and the solvent evaporated to give 1.10 g (96%) of ethyl 4-ethylthieno[3,2-b]pyrrole-5-carboxylate as a brown oil. $^1$H NMR (CDCl$_3$) δ (ppm): 7.34 (d, J=5.4 Hz, 1H), 7.20 (s, 1H), 6.96 (d, J=5.4 Hz, 1H), 4.56 (q, J=7.3 Hz, 2H), 4.34 (q, J=7.3 Hz, 2H), 1.46-1.34 (m, 6H); MS (ESI): m/z: 224 [M+H]$^+$.

4-Ethylthieno[3,2-b]pyrrole-5-carboxylic acid 0.21 g (9.0 mmol) of LiOH in 4 mL of H$_2$O was added at RT to a solution of 0.40 g (1.8 mmol) of ethyl 4-ethylthieno[3,2-b]pyrrole-5-carboxylate in 4 mL of EtOH. The mixture was stirred for 30 min at reflux, then EtOH was evaporated, water was added and the pH was brought to about 2 with 2 M HCl. The mixture extracted with EtOAc, the combined organic layers dried over Na$_2$SO$_4$ and the solvent evaporated to give 0.35 g (quantitative) of 4-ethylthieno[3,2-b]pyrrole-5-carboxylic acid as a beige solid. $^1$H NMR (DMSO-d$_6$) δ (ppm): 12.47 (bs, 1H), 7.56 (d, J=5.4 Hz, 1H), 7.24 (d, J=5.4 Hz, 1H), 7.13 (s, 1H), 4.51 (q, J=7.3 Hz, 2H), 1.28 (t, J=7.3 Hz, 3H); MS (ESI): m/z: 196 [M+H]$^+$.

Intermediate 3: 6-methylthieno[2,3-b]pyrrole-5-carboxylic acid

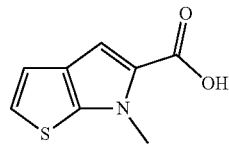

Ethyl 6-methylthieno[2,3-b]pyrrole-5-carboxylate

Ethyl 6-methylthieno[2,3-b]pyrrole-5-carboxylate was obtained as yellow solid starting from ethyl 6H-thieno[2,3-b]pyrrole-5-carboxylate (Eras J. et al. J. Het. Chemistry 1984, 21, 215-217) according to the procedure for Intermediate 1, Step 1. $^1$H NMR (CDCl$_3$) δ (ppm): 7.34 (d, J=5.4 Hz, 1H), 7.20 (s, 1H), 6.95 (d, J=5.4 Hz, 1H), 4.34 (q, J=7.3 Hz, 2H), 4.07 (s, 3H), 1.39 (t, J=7.1 Hz, 3H); MS (ESI): m/z: 210 [M+H]$^+$ 6-Methylthieno[2,3-b]pyrrole-5-carboxylic acid 6-methylthieno[2,3-b]pyrrole-5-carboxylic acid was obtained as a white solid from ethyl 6-methylthieno[2,3-b]pyrrole-5-carboxylate according to the procedure for Intermediate 1, Step 2. $^1$H NMR (DMSO-d$_6$) δ (ppm): 12.49 (bs, 1H), 7.17 (d, J=5.4 Hz, 1H), 7.08-7.00 (m, 2H), 3.95 (s, 3H); MS (ESI): m/z: 182 [M+H]$^+$ Compound 1: 1H-indol-3-yl-(4-methylthieno[3,2-b]pyrrol-5-yl)methanone

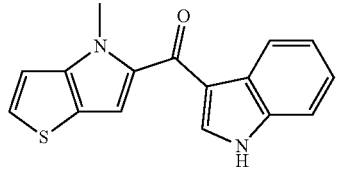 [SMILES: Cn1c(C(=O)c2c[nH]c3ccccc23)cc2sccc21]

0.26 mL (3.5 mmol) of SOCl$_2$ and 3 drops of DMF were added to a solution of 0.49 g (2.70 mmol) of 4-methylthieno[3,2-b]pyrrole-5-carboxylic acid (Intermediate 1) in 9 mL of THF and the mixture was heated to reflux for about 3 h. Then, the solvent was evaporated and the formed acyl chloride was used in the next step without any further purification.

0.972 mL of a 3 M methyl magnesium bromide solution in Et$_2$O was slowly added to an ice-cooled solution of 0.287 g (2.43 mmol) indole (Sigma-Aldrich Cat. Nbr. I3408) in 3.5 mL of Et$_2$O under nitrogen atmosphere. After the addition the reaction mixture was allowed to reach RT, stirred for 2 h and then again cooled down to 0° C. and a solution of 4-methylthieno[3,2-b]pyrrole-5-carbonyl chloride in 5 mL of Et$_2$O was added. The resulting mixture was warmed up to RT and stirred for 2 h followed by slow addition of 6 mL of a saturated NH$_4$Cl solution. The mixture was stirred at room temperature for additional 1 h and then partitioned between CH$_2$Cl$_2$ and water. The combined organic phases were dried over Na$_2$SO$_4$, filtered, concentrated and purified by column chromatography (eluent: hexane/acetone, 0% to 15% of acetone (by volume)) to afford 276 mg (yield: 41%) of 1H-indol-3-yl-(4-methylthieno[3,2-b]pyrrol-5-yl)methanone as a mustard-coloured solid. $^1$H NMR (DMSO-d$_6$) δ (ppm): 11.99 (bs, 1H), 8.25-8.20 (m, 1H), 8.13 (s, 1H), 7.58 (d, J=5.4 Hz, 1H), 7.52-7.48 (m, 1H), 7.27 (d, J=5.4 Hz, 1H), 7.26-7.17 (m, 2H), 7.16 (s, 1H), 4.02 (s, 3H); MS (ESI): m/z: 281 [M+H]$^+$.

The following compounds (see Table 1) were prepared starting from 4-methylthieno[3,2-b]pyrrole-5-carboxylic acid (Intermediate 1: Compounds 2-4), 4-ethylthieno[3,2-b]pyrrole-5-carboxylic acid (Intermediate 2: Compound 5), or 6-methylthieno[2,3-b]pyrrole-5-carboxylic acid (Intermediate 3: Compound 6) and the appropriate indoles according to the procedure described for Compound 1.

TABLE 1

| No. | Name | indole | Structure | Analytical Data |
|---|---|---|---|---|
| 2 | (5-methyl-1H-indol-3-yl)-(4-methylthieno[3,2-b]pyrrol-5-yl)methanone | (Fluorochem, Cat. No. 040072) | 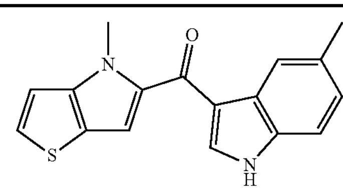 | $^1$H NMR (DMSO-d$_6$) δ (ppm): 11.88 (s, 1 H), 8.07 (s, 1 H), 8.06-8.04 (m, 1 H), 7.57 (d, J = 5.4 Hz, 1 H), 7.40-7.36 (m, 1 H), 7.27 (d, J = 5.4 1 H, 7.14 (s, 1 H), 7.08-7.04 (m, 1 H), 4.01 (s, 3 H), 2.42 (s, 3 H); MS (ESI): m/z: 295 [M + H]$^+$. |

TABLE 1-continued

| No. | Name | indole | Structure | Analytical Data |
|---|---|---|---|---|
| 3 | (5-ethyl-1H-indol-3-yl)-(4-methylthieno[3,2-b]pyrrol-5-yl)methanone | 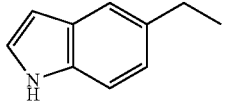 (Fluorochem, Cat. No. 221620) | 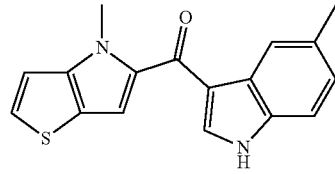 | $^1$H NMR (DMSO-d$_6$) δ (ppm): 11.87 (bs, 1 H), 8.15-8.01 (m, 2 H), 7.57 (d, J = 5.4 Hz, 1 H), 7.43-7.37 (m, 1 H), 7.27 (d, J = 5.4 Hz, 1 H), 7.13 (s, 1 H), 7.12-7.07 (m, 1 H), 4.01 (s, 3 H), 2.72 (q, J = 7.6 Hz, 2 H), 1.24 (t, J = 7.6 Hz, 3 H); MS (ESI): m/z: 309 [M + H]$^+$. |
| 4 | (5-bromo-1H-indol-3-yl)-(4-methylthieno[3,2-b]pyrrol-5-yl)methanone | 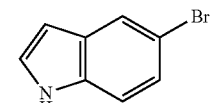 (Sigma-Aldrich Cat. No. B68607) | 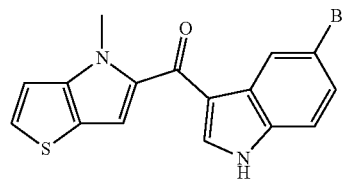 | $^1$H NMR (DMSO-d$_6$) δ (ppm): 12.13 (bs, 1 H), 8.37 (d, J = 2.0 Hz, 1 H), 8.21 (s, 1 H), 7.60 (d, J = 5.4 Hz, 1 H), 7.48 (d, J = 8.3 Hz, 1 H), 7.37 (dd, J = 2.0, 8.3 Hz, 1 H), 7.28 (d, J = 5.4 Hz, 1 H), 7.21 (s, 1 H), 4.02 (s, 3 H); MS (ESI): m/z: 359 [M + H]$^+$. |
| 5 | (4-ethylthieno[3,2-b]pyrrol-5-yl)-(1H-indol-3-yl)methanone | 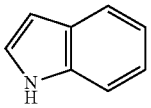 (Sigma-Aldrich Cat. No. I3408) | 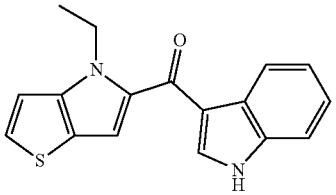 [SMILES: CCn1c(C(=O)c2c[nH]c3ccccc23)cc2sccc21] | $^1$H NMR (DMSO-d$_6$) δ (ppm): 11.96 (bs, 1 H), 8.25-8.20 (m, 1 H), 8.12 (s, 1 H), 7.58 (d, J = 5.4 Hz, 1 H), 7.52-7.47 (m, 1 H), 7.29 (d, J = 5.4 Hz, 1 H), 7.26-7.17 (m, 2 H), 7.14 (s, 1 H), 4.51 (q, J = 7.3 Hz, 2 H), 1.35 (t, J = 7.3 Hz, 3 H); MS (ESI): m/z: 295 [M + H]$^+$. |
| 6 | 1H-indol-3-yl-(6-methylthieno[2,3-b]pyrrol-5-yl)methanone | 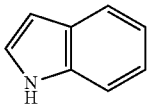 (Sigma-Aldrich Cat. No. I3408) | 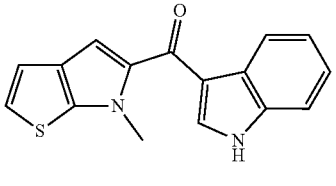 [SMILES: Cn1c(C(=O)c2c[nH]c3ccccc23)cc2ccsc21] | $^1$H NMR (DMSO-d$_6$) δ (ppm): 11.95 (bs, 1 H), 8.24-8.19 (m, 1 H), 8.13 (d, J = 2.4 Hz, 1 H), 7.52-7.48 (m, 1 H), 7.27-7.17 (m, 3 H), 7.10 (d, J = 5.4 Hz, 1 H), 7.08 (s, 1 H), 3.98 (s, 3 H); MS (ESI): m/z: 281 [M + H]$^+$. |

Intermediate 4: tert-Butyl 3-[[2-(2-bromoethoxy)phenoxy]methyl]pyrrolidine-1-carboxylate

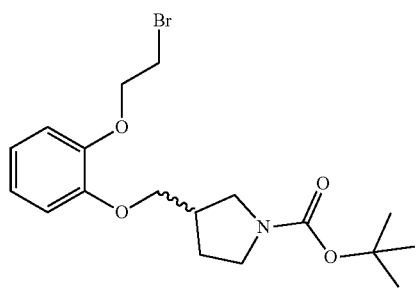 [SMILES: CC(C)(C)OC(=O)N1CCC(COc2ccccc2OCCBr)C1]

tert-butyl 3-[(3-hydroxyphenoxy)methyl]pyrrolidine-1-carboxylate 0.414 g (1.57 mmol) of tert-butyl 3-(bromomethyl)pyrrolidine-1-carboxylate in 1 mL of DMF were added under nitrogen atmosphere to a solution of 0.219 g (1.99 mmol) of catechol (Sigma-Aldrich, Cat. No. 135011) and 0.649 g (1.99 mmol) of Cs$_2$CO$_3$ in 3 mL of dry DMF. The reaction mixture was stirred overnight at 80° C. The reaction solution was then diluted with brine and the product was extracted with EtOAc. The combined organic phases were dried over Na$_2$SO$_4$, the solvent was removed and the crude mixture was purified by flash chromatography on silica gel (hexane/acetone, 0% to 10% of acetone (by volume)) to give 0.112 g of tert-butyl 3-[(2-hydroxyphenoxy)methyl]pyrrolidine-1-carboxylate (yield: 30%). $^1$H NMR (CDCl$_3$) δ (ppm): 6.98-6.83 (m, 4H), 5.55 (s, 1H), 4.07-3.98 (m, 2H), 3.66-3.58 (m, 1H), 3.55-3.47 (m, 1H), 3.45-3.35 (m, 1H), 3.27-3.18 (m, 1H), 2.78-2.67 (m, 1H), 2.17-2.05 (m, 1H), 1.88-1.74 (m, 1H), 1.48 (s, 9H); MS (ESI): m/z: 238 [M−56+H]⁺.

tert-butyl 3-[[2-(2-bromoethoxy)phenoxy]methyl]
pyrrolidine-1-carboxylate 0.16 g (0.74 mmol, 0.15 mL) of DIAD (Sigma-Aldrich, Cat. No. 225541) were added dropwise to a solution comprising 0.145 g (0.494 mmol) of tert-butyl 3-[(2-hydroxyphenoxy)methyl]pyrrolidine-1-carboxylate, 0.098 g (0.74 mmol, 0.055 mL) of 2-bromoethanol (Sigma-Aldrich, Cat. No. B65586) and 0.20 g (0.74 mmol) of PPh₃ (Sigma-Aldrich, Cat. No. T84409) in 5 mL of dry THF at 0° C. The solution was allowed to reach RT and was stirred overnight. Then, further 0.055 mL of 2-bromoethanol, 0.20 mg of PPh₃ and 0.153 mL of DIAD were added to the reaction mixture cooled down to 0° C. and the mixture was stirred at RT for further 24 h. The solvent was removed and the crude product was purified by flash chromatography on silica gel (hexane/acetone, 0% to 5% of acetone (by volume)) to provide 0.113 g of tert-butyl 3-[[2-(2-bromoethoxy)phenoxy]methyl]pyrrolidine-1-carboxylate (yield: 57%) as colourless oil. ¹H NMR (CDCl₃) δ (ppm): 7.05-6.84 (m, 4H), 4.32 (t, J=6.4 Hz, 2H), 4.04-3.93 (m, 2H), 3.69-3.59 (m, 3H), 3.52-3.45 (m, 1H), 3.42-3.33 (m, 1H), 3.28-3.20 (m, 1H), 2.82-2.68 (m, 1H), 2.15-2.05 (m, 1H), 1.87-1.76 (m, 1H), 1.48 (s, 9H); MS (ESI): m/z: 344 [M−56+H]+.

Intermediate 5: tert-Butyl 3-[[3-(2-bromoethoxy)phenoxy]methyl]pyrrolidine-1-carboxylate

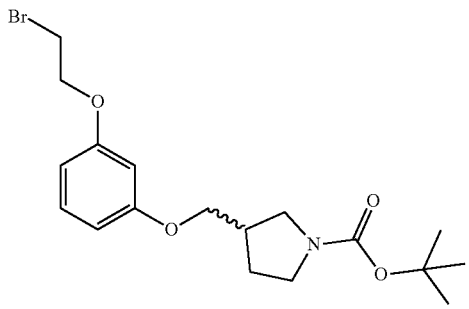 [SMILES: CC(C)(C)OC(=O)N1CCC(COc2cccc(OCCBr)c2)C1]

tert-butyl 3-[(3-hydroxyphenoxy)methyl]pyrrolidine-1-carboxylate 0.64 g (3.0 mmol, 0.62 mL) of DIAD (Sigma-Aldrich, Cat. No. 225541) were added dropwise to a solution of 0.33 g (3.0 mmol) of resorcinol (Sigma-Aldrich, Cat. No. 398047), 0.40 g (2.0 mmol) of tert-butyl 3-(hydroxymethyl)pyrrolidine-1-carboxylate (Fluorochem, Cat. No. 048620) and 0.80 g (3.0 mmol) of PPh₃ (Sigma-Aldrich, Cat. No. T84409) in 20 mL of dry THF at 0° C. The reaction mixture was allowed to reach RT and was stirred overnight. The solvent was then removed and the crude mixture was purified by flash chromatography on silica gel (hexane/acetone, 0% to 15% of acetone (by volume)) to give 0.26 g of tert-butyl 3-[(3-hydroxyphenoxy)methyl]pyrrolidine-1-carboxylate (yield: 29%). ¹H NMR (CDCl₃) δ (ppm): 7.18-7.10 (m, 1H), 6.53-6.39 (m, 3H), 3.96-3.84 (m, 2H), 3.63-3.55 (m, 1H), 3.53-3.44 (m, 1H), 3.42-3.32 (m, 1H), 3.26-3.16 (m, 1H), 2.74-2.61 (m, 1H), 2.14-2.02 (m, 1H), 1.85-1.74 (m, 1H), 1.48 (s, 9H); MS (ESI): m/z: 238 [M−56+H]⁺.

tert-butyl 3-[[3-(2-bromoethoxy)phenoxy]methyl]
pyrrolidine-1-carboxylate 0.17 g (0.79 mmol, 0.16 mL) of DIAD (Sigma-Aldrich, Cat. No. 225541) were added dropwise to a solution comprising 0.154 g (0.525 mmol) of tert-butyl 3-[(3-hydroxyphenoxy)methyl]pyrrolidine-1-carboxylate, 0.085 g (0.79 mmol, 0.059 mL) of 2-bromoethanol (Sigma-Aldrich, Cat. No. 865586) and 0.209 g (0.79 mmol) of PPh₃ (Sigma-Aldrich, Cat. No. T84409) in 5 mL of dry THF at 0° C. The solution was allowed to reach RT and was stirred overnight. Then further 0.032 mL of 2-bromoethanol, 0.114 mg of PPh₃ and 0.089 mL of DIAD were added to the reaction mixture cooled down to 0° C. and the mixture was stirred at RT for further 24 h. The solvent was removed and the crude product was purified by flash chromatography on silica gel (hexane/acetone, 0% to 5% of acetone (by volume)) to provide 0.128 g of tert-butyl 3-[[3-(2-bromoethoxy)phenoxy]methyl]pyrrolidine-1-carboxylate (yield: 61%) as colourless oil. ¹H NMR (CDCl₃) δ (ppm): 7.23-7.15 (m, 1H), 6.56-6.50 (m, 2H), 6.49-6.45 (m, 1H), 4.29 (t, J=6.4 Hz, 2H), 3.96-3.84 (m, 2H), 3.65 (t, J=6.1 Hz, 2H), 3.62-3.56 (m, 1H), 3.53-3.44 (m, 1H), 3.41-3.33 (m, 1H), 3.24-3.17 (m, 1H), 2.74-2.62 (m, 1H), 2.13-2.02 (m, 1H), 1.85-1.73 (m, 1H), 1.48 (s, 9H); MS (ESI): m/z: 344 [M−56+H]⁺.

Intermediate 6: tert-Butyl (3S)-3-[[3-(2-bromoethoxy)phenoxy]methyl]pyrrolidine-1-carboxylate

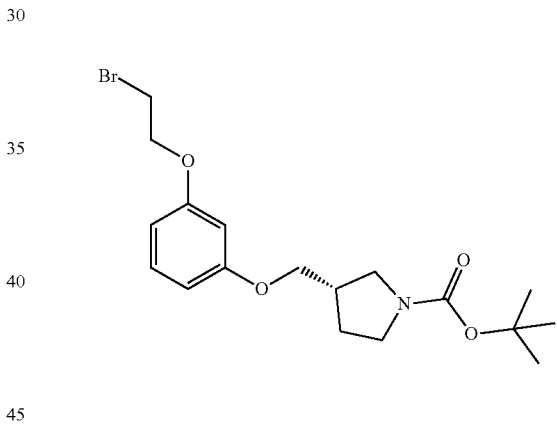

tert-Butyl (3S)-3-[(3-hydroxyphenoxy)methyl]pyrrolidine-1-carboxylate 0.13 g of tert-butyl (3S)-3-[(3-hydroxyphenoxy)methyl]pyrrolidine-1-carboxylate was prepared according to the procedure for Intermediate 5, step 1, starting from 0.3 g (2.7 mmol) of resorcinol (Sigma-Aldrich, Cat. No. 398047) and 0.38 g (1.8 mmol) of tert-butyl (3S)-3-(hydroxymethyl)pyrrolidine-1-carboxylate (Fluorochem, Cat. No. 048621) (yield: 25%). ¹H NMR (CDCl₃) δ (ppm):=7.17-7.08 (m, 1H), 6.52-6.37 (m, 3H), 4.85 (s, 1H), 3.98-3.82 (m, 2H), 3.66-3.55 (m, 1H), 3.54-3.44 (m, 1H), 3.42-3.32 (m, 1H), 3.26-3.14 (m, 1H), 2.75-2.61 (m, 1H), 2.13-2.00 (m, 1H), 1.87-1.71 (m, 1H), 1.48 (s, 9H); MS (ESI): m/z: 238 [M−56+H]⁺.

tert-Butyl (3S)-3-[[3-(2-bromoethoxy)phenoxy]methyl]pyrrolidine-1-carboxylate 0.10 g of tert-butyl (3S)-3-[[3-(2-bromoethoxy)phenoxy]methyl]pyrrolidine-1-carboxylate was prepared according to the procedure for Intermediate 5, step 2, starting from 0.13 g (0.44 mmol) of tert-butyl (3S)-3-[(3-hydroxyphenoxy) methyl]pyrrolidine-1-carboxylate and 0.088 g (0.67 mmol, 0.05 mL) of 2-bromoethanol (yield: 56%). ¹H NMR (CDCl₃) δ (ppm): 7.24-7.15 (m, 1H), 6.57-6.50 (m, 2H), 6.49-6.45 (m, 1H), 4.29 (t, J=6.4 Hz, 2H), 3.97-3.85 (m, 2H), 3.64 (t, J=6.4 Hz, 2H), 3.62-3.57 (m, 1H), 3.53-3.45 (m, 1H), 3.41-3.33 (m, 1H), 3.25-3.17 (m, 1H), 2.72-2.63 (m, 1H), 2.12-2.03 (m, 1H), 1.85-1.74 (m, 1H), 1.48 (s, 9H); MS (ESI): m/z: 344 [M−56+H]⁺.

Intermediate 7: tert-Butyl (3R)-3-[[3-(2-bromoethoxy)phenoxy]methyl]pyrrolidine-1-carboxylate

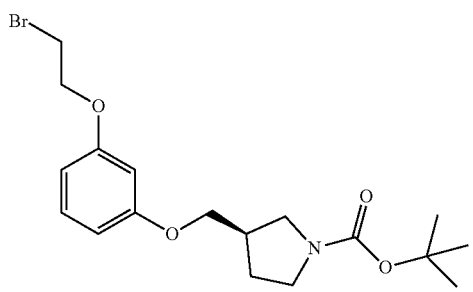 [SMILES: CC(C)(C)OC(=O)N1CC[C@@H](COc2cccc(OCCBr)c2)C1]

tert-Butyl (3R)-3-[(3-hydroxyphenoxy)methyl]pyrrolidine-1-carboxylate 0.35 g of tert-butyl (3R)-3-[(3-hydroxyphenoxy)methyl] pyrrolidine-1-carboxylate was prepared according to the procedure for Intermediate 5, step 1, starting from 0.5 g (4.5 mmol) of resorcinol (Sigma-Aldrich, Cat. No. 398047) and 0.636 g (3 mmol) of tert-butyl (3R)-3-(hydroxymethyl) pyrrolidine-1-carboxylate (Fluorochem, Cat. No. 048622) (yield: 40%). ¹H NMR (CDCl₃) δ (ppm): 7.18-7.09 (m, 1H), 6.51-6.39 (m, 3H), 5.06 (s, 1H), 3.95-3.84 (m, 2H), 3.64-3.55 (m, 1H), 3.54-3.44 (m, 1H), 3.42-3.33 (m, 1H), 3.24-3.16 (m, 1H), 2.73-2.61 (m, 1H), 2.13-2.02 (m, 1H), 1.87-1.73 (m, 1H), 1.48 (s, 9H); MS (ESI): m/z: 238 [M−56+H]⁺.

tert-Butyl (3R)-3-[[3-(2-bromoethoxy)phenoxy]methyl]pyrrolidine-1-carboxylate 0.16 g of tert-butyl (3R)-3-[[3-(2-bromoethoxy)phenoxy] methyl]pyrrolidine-1-carboxylate was prepared according to the procedure for Intermediate 5, step 2, starting from 0.18 g (0.60 mmol) of tert-butyl (3R)-3-[(3-hydroxyphenoxy) methyl]pyrrolidine-1-carboxylate and 0.12 g (0.90 mmol, 0.067 mL) of 2-bromoethanol (yield: 67%). ¹H NMR (CDCl₃) δ (ppm): 7.23-7.15 (m, 1H), 6.55-6.50 (m, 2H), 6.49-6.46 (m, 1H), 4.29 (t, J=6.4 Hz, 2H), 3.97-3.84 (m, 2H), 3.64 (t, J=6.4 Hz, 2H), 3.62-3.57 (m, 1H), 3.53-3.45 (m, 1H), 3.42-3.33 (m, 1H), 3.25-3.16 (m, 1H), 2.72-2.61 (m, 1H), 2.12-2.01 (m, 1H), 1.86-1.73 (m, 1H), 1.48 (s, 9H); MS (ESI): m/z: 344 [M−56+H]⁺.

Intermediate 8: tert-Butyl 3-[[4-(2-bromoethoxy)phenoxy]methyl]pyrrolidine-1-carboxylate

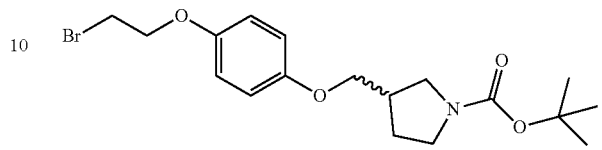

tert-Butyl 3-[(4-hydroxyphenoxy)methyl]pyrrolidine-1-carboxylate 0.073 g of tert-butyl 3-[(4-hydroxyphenoxy)methyl]pyrrolidine-1-carboxylate was prepared according to the procedure for Intermediate 5, step 1, starting from 0.22 g (2.0 mmol) of hydroquinone (Sigma-Aldrich, Cat. No. H9003) and 0.219 g (1 mmol) of tert-butyl 3-(hydroxymethyl) pyrrolidine-1-carboxylate (Fluorochem, Cat. No. 048620) (yield: 25%). ¹H NMR (CDCl₃) δ (ppm): 6.82-6.73 (m, 4H), 4.59 (s, 1H), 3.94-3.80 (m, 2H), 3.63-3.55 (m, 1H), 3.53-3.44 (m, 1H), 3.42-3.32 (m, 1H), 3.24-3.14 (m, 1H), 2.70-2.60 (m, 1H), 2.12-2.00 (m, 1H), 1.87-1.73 (m, 1H), 1.47 (s, 9H); MS (ESI): m/z: 238 [M−56+H]⁺.

tert-Butyl 3-[[4-(2-bromoethoxy)phenoxy]methyl] pyrrolidine-1-carboxylate 0.053 g of tert-butyl 3-[[4-(2-bromoethoxy)phenoxy] methyl]pyrrolidine-1-carboxylate was prepared according to the procedure for Intermediate 5, step 2, starting from 0.073 g (0.25 mmol) of tert-butyl 3-[(4-hydroxyphenoxy)methyl] pyrrolidine-1-carboxylate and 0.049 g (0.37 mmol, 0.028 mL) of 2-bromoethanol (yield: 53%). ¹H NMR (CDCl₃) δ (ppm): 6.92-6.79 (m, 4H), 4.25 (t, J=6.4 Hz, 2H), 3.97-3.81 (m, 2H), 3.62 (t, J=6.1 Hz, 2H), 3.60-3.56 (m, 1H), 3.51-3.44 (m, 1H), 3.41-3.32 (m, 1H), 3.23-3.16 (m, 1H), 2.70-2.61 (m, 1H), 2.11-2.02 (m, 1H), 1.85-1.74 (m, 1H), 1.47 (s, 9H); MS (ESI): m/z: 344 [M−56+H]⁺.

Intermediate 9: tert-Butyl 4-[3-(2-bromoethoxy)phenoxy]piperidine-1-carboxylate

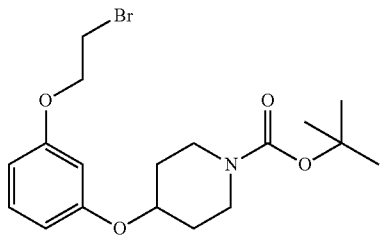 [SMILES: CC(C)(C)OC(=O)N1CCC(Oc2cccc(OCCBr)c2)CC1]

tert-Butyl 4-(3-hydroxyphenoxy)piperidine-1-carboxylate 0.64 g (3.0 mmol, 0.62 mL) of DIAD (Sigma-Aldrich, Cat. No. 225541) were added dropwise to a solution of 0.33 g (3.0 mmol) of resorcinol (Sigma-Aldrich, Cat. No. 398047), 0.42 g (2.0 mmol) of tert-butyl 4-hydroxypiperidine-1-carboxylate (Apollo, Cat. No. OR5404) and 0.80 g (3.0 mmol) of PPh$_3$ (Sigma-Aldrich, Cat. No. T84409) in 20 mL of dry THF at 0° C. The reaction mixture was allowed to reach RT and was stirred overnight. The solvent was then removed and the crude mixture was purified by flash chromatography on silica gel (hexane/acetone, 0% to 15% of acetone, v/v) to give 0.217 g of tert-butyl 4-(3-hydroxyphenoxy)piperidine-1-carboxylate (yield: 37%) as white solid. $^1$H NMR (CDCl$_3$) δ (ppm): 7.16-7.11 (m, 1H), 6.52-6.48 (m, 1H), 6.46-6.41 (m, 2H), 4.96 (bs, 1H), 4.50-4.38 (m, 1H), 3.75-3.65 (m, 2H), 3.39-3.29 (m, 2H), 1.97-1.86 (m, 2H), 1.81-1.69 (m, 2H), 1.48 (s, 9H); MS (ESI): m/z: 238 [M−56+H]$^+$.

tert-Butyl 4-[3-(2-bromoethoxy)phenoxy]piperidine-1-carboxylate 0.16 g (0.76 mmol, 0.158 mL) of DIAD (Sigma-Aldrich, Cat. No. 225541) were added dropwise to a solution comprising 0.150 g (0.51 mmol) of tert-butyl 4-(3-hydroxyphenoxy)piperidine-1-carboxylate, 0.100 g (0.76 mmol, 0.057 mL) of 2-bromoethanol (Sigma-Aldrich, Cat. No. B65586) and 0.203 g (0.76 mmol) of PPh$_3$ (Sigma-Aldrich, Cat. No. T84409) in 5 mL of dry THF at 0° C. The solution was allowed to reach RT and was stirred overnight. Then further 0.028 mL of 2-bromoethanol, 0.101 mg of PPh$_3$ and 0.079 mL of DIAD were added to the reaction mixture cooled down to 0° C. and the mixture was stirred at RT for further 24 h. The solvent was removed and the crude product was purified by flash chromatography on silica gel (hexane/acetone, 0% to 5% of acetone (by volume)) to provide 0.105 g of tert-butyl 4-[3-(2-bromoethoxy)phenoxy]piperidine-1-carboxylate (yield: 51%) as colourless oil. $^1$H NMR (CDCl$_3$) δ (ppm): 7.23-7.15 (m, 1H), 6.58-6.47 (m, 3H), 4.50-4.43 (m, 1H), 4.28 (t, J=6.4 Hz, 2H), 3.75-3.67 (m, 2H), 3.64 (t, J=6.4 Hz, 2H), 3.38-3.28 (m, 2H), 1.96-1.86 (m, 2H), 1.81-1.69 (m, 2H), 1.48 (s, 9H); MS (ESI): m/z: 344 [M−56+H]$^+$.

Intermediate 10: tert-Butyl 4-[4-(2-bromoethoxy)phenoxy]piperidine-1-carboxylate

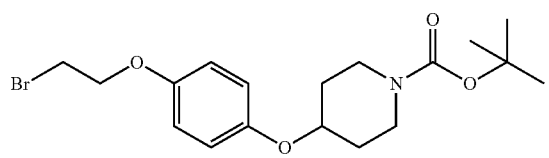 [SMILES: CC(C)(C)OC(=O)N1CCC(Oc2ccc(OCCBr)cc2)CC1]

tert-Butyl 4-(4-benzyloxyphenoxy)piperidine-1-carboxylate 0.8 g of tert-butyl 4-(4-benzyloxyphenoxy)piperidine-1-carboxylate was prepared according to the procedure for Intermediate 9, step 1 starting from 0.60 g (3.0 mmol) of 4-benzyloxyphenol (Sigma-Aldrich, Cat. No. 158348) and 0.93 g (4.5 mmol) of tert-butyl 4-hydroxypiperidine-1-carboxylate (Apollo, Cat. No. OR5404) (yield: 70%). $^1$H NMR (CDCl$_3$) δ (ppm): 7.46-7.42 (m, 2H), 7.42-7.37 (m, 2H), 7.36-7.31 (m, 1H), 6.93-6.84 (m, 4H), 5.03 (s, 2H), 4.38-4.28 (m, 1H), 3.76-3.68 (m, 2H), 3.35-3.24 (m, 2H), 1.95-1.84 (m, 2H), 1.78-1.67 (m, 2H), 1.48 (s, 9H); MS (ESI): m/z: 328 [M−56+H]$^+$.

tert-Butyl 4-(4-hydroxyphenoxy)piperidine-1-carboxylate 0.454 g (1.18 mmol) of tert-butyl 4-(4-benzyloxyphenoxy)piperidine-1-carboxylate dissolved in 47 mL of dry EtOH were hydrogenated in an H-Cube apparatus using a 10% Pd/C (by weight) cartridge at 25° C., at atmospheric pressure and with a flow of 0.5 mL/min for 5 h. The solution was then concentrated to provide 0.34 g of tert-butyl 4-(4-hydroxyphenoxy)piperidine-1-carboxylate (yield: 98%) as a white solid. $^1$H NMR (CDCl$_3$) δ (ppm): 6.87-6.71 (m, 4H), 4.58 (bs, 1H), 4.36-4.27 (m, 1H), 3.76-3.67 (m, 2H), 3.37-3.24 (m, 2H), 1.95-1.82 (m, 2H), 1.78-1.66 (m, 2H), 1.48 (s, 9H); MS (ESI): m/z: 238 [M−56+H]$^+$.

tert-Butyl 4-[4-(2-bromoethoxy)phenoxy]piperidine-1-carboxylate 0.168 g (0.419 mmol), tert-Butyl 4-[4-(2-bromoethoxy)phenoxy]piperidine-1-carboxylate was prepared according to the procedure for Intermediate 9, step 2, starting from 0.320 g (1.09 mmol) of tert-butyl 4-(4-hydroxyphenoxy)piperidine-1-carboxylate and 0.214 g (1.63 mmol, 0.122 mL) of 2-bromoethanol (yield: 38%). $^1$H NMR (CDCl$_3$) δ (ppm): 6.92-6.80 (m, 4H), 4.37-4.31 (m, 1H), 4.25 (t, J=6.1 Hz, 2H), 3.76-3.67 (m, 2H), 3.63 (t, J=6.4 Hz, 2H), 3.35-3.26 (m, 2H), 1.95-1.85 (m, 2H), 1.77-1.67 (m, 2H), 1.48 (s, 9H); MS (ESI): m/z: 344 [M−56+H]$^+$.

Intermediate 11: tert-Butyl 4-[[3-(2-bromoethoxy)phenoxy]methyl]piperidine-1-carboxylate

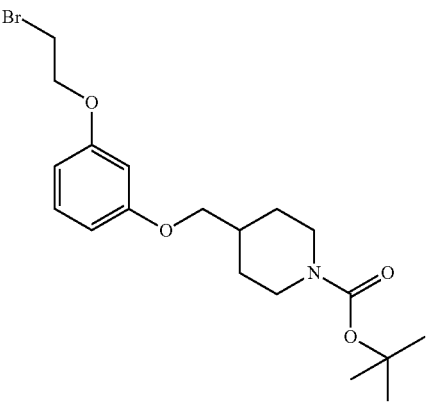 [SMILES: CC(C)(C)OC(=O)N1CCC(COc2cccc(OCCBr)c2)CC1]

tert-butyl 4-[(3-hydroxyphenoxy)methyl]piperidine-1-carboxylate 0.197 g (0.640 mmol) of tert-butyl 4-[(3-hydroxyphenoxy)methyl]piperidine-1-carboxylate was prepared according to the procedure for Intermediate 9, step 1, starting from 0.333 g (3.00 mmol) of resorcinol (Sigma-Aldrich, Cat. No. 398047) and 0.431 g (2.00 mmol) of tert-butyl 4-(hydroxymethyl)piperidine-1-carboxylate (Sigma-Aldrich, Cat. No. 556017) (yield: 32%). $^1$H NMR (CDCl$_3$) δ (ppm): 7.18-7.09 (m, 1H), 6.51-6.37 (m, 3H), 4.86 (bs, 1H), 4.23-4.10 (m, 2H), 3.78 (d, J=6.4 Hz, 2H), 2.80-2.69 (m, 2H), 2.02-1.90 (m, 1H), 1.86-1.76 (m, 2H), 1.48 (s, 9H), 1.32-1.19 (m, 2H); MS (ESI): m/z: 252 [M−56+H]⁺.

tert-Butyl 4-[[3-(2-bromoethoxy)phenoxy]methyl] piperidine-1-carboxylate 0.107 g (0.258 mmol) of tert-butyl 4-[[3-(2-bromoethoxy)phenoxy]methyl]piperidine-1-carboxylate was prepared according to the procedure for Intermediate 9, step 2, starting from 0.152 g (0.490 mmol) of tert-butyl 4-[(3-hydroxyphenoxy)methyl]piperidine-1-carboxylate and 0.097 g (0.74 mmol, 0.055 mL) of 2-bromoethanol (yield: 52%). ¹H NMR (CDCl₃) δ (ppm): 7.23-7.14 (m, 1H), 6.57-6.45 (m, 3H), 4.29 (t, J=6.4 Hz, 2H), 4.21-4.10 (m, 2H), 3.79 (d, J=6.4 Hz, 2H), 3.64 (t, J=6.4 Hz, 2H), 2.81-2.70 (m, 2H), 2.02-1.90 (m, 1H), 1.87-1.78 (m, 2H), 1.48 (s, 9H), 1.34-1.21 (m, 2H); MS (ESI): m/z: 358 [M−56+H]⁺.

Intermediate 12: tert-Butyl 4-[[4-(2-bromoethoxy)phenoxy]methyl]piperidine-1-carboxylate

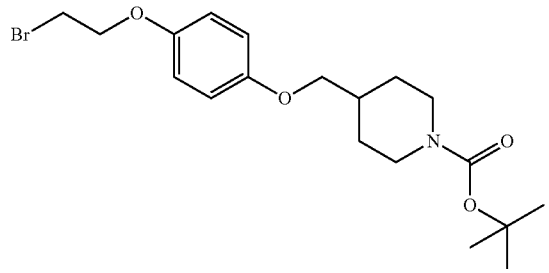 [SMILES: CC(C)(C)OC(=O)N1CCC(COc2ccc(OCCBr)cc2)CC1]

tert-Butyl 4-[(4-hydroxyphenoxy)methyl]piperidine-1-carboxylate 0.28 g of tert-butyl 4-[(4-hydroxyphenoxy)methyl]pyrrolidine-1-carboxylate was prepared according to the procedure for Intermediate 9, step 1, starting from 0.50 g (4.5 mmol) of hydroquinone (Sigma-Aldrich, Cat. No. H9003) and 0.65 g (3.0 mmol) of tert-butyl 4-(hydroxymethyl)piperidine-1-carboxylate (Sigma-Aldrich, Cat. No. 556017) (yield: 31%). ¹H NMR (CDCl₃) δ (ppm): 6.83-6.70 (m, 4H), 4.58 (bs, 1H), 4.22-4.10 (m, 2H), 3.75 (d, J=6.4 Hz, 2H), 2.81-2.69 (m, 2H), 2.00-1.88 (m, 1H), 1.86-1.77 (m, 2H), 1.48 (s, 9H), 1.31-1.23 (m, 2H); MS (ESI): m/z: 252 [M−56+H]⁺.

tert-Butyl 4-[[4-(2-bromoethoxy)phenoxy]methyl] piperidine-1-carboxylate 0.11 g of tert-butyl 4-[[4-(2-bromoethoxy)phenoxy]methyl]piperidine-1-carboxylate was prepared according to the procedure for Intermediate 9, step 2, starting from 0.28 g (0.90 mmol) of tert-butyl 4-[(4-hydroxyphenoxy)methyl]pyrrolidine-1-carboxylate and 0.18 g (1.35 mmol, 0.101 mL) of 2-bromoethanol (yield: 29%). ¹H NMR (CDCl₃) δ (ppm): 6.89-6.79 (m, 4H), 4.25 (t, J=6.4 Hz, 2H), 4.20-4.11 (m, 2H), 3.76 (d, J=6.4 Hz, 2H), 3.62 (t, J=6.4 Hz, 2H), 2.81-2.70 (m, 2H), 2.00-1.88 (m, 1H), 1.87-1.77 (m, 2H), 1.47 (s, 9H), 1.32-1.23 (m, 2H); MS (ESI): m/z: 358 [M−56+H]⁺.

Intermediate 13: tert-Butyl 4-[3-(2-bromoethoxy)phenoxy]azepane-1-carboxylate

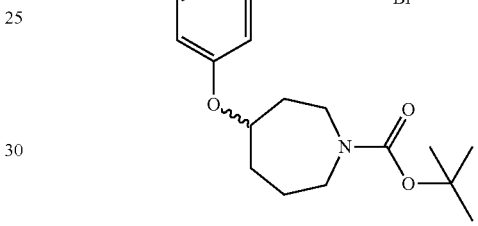

tert-Butyl 4-(3-hydroxyphenoxy)azepane-1-carboxylate 0.43 g of tert-butyl 4-(3-hydroxyphenoxy)azepane-1-carboxylate was prepared according to the procedure for Intermediate 9, step 1, starting from 0.50 g (4.5 mmol) of resorcinol (Sigma-Aldrich, Cat. No. 398047) and 0.65 g (3.0 mmol) of tert-butyl 4-hydroxyazepane-1-carboxylate (Sigma-Aldrich, Cat. No. CDS009029) (yield: 46%). ¹H NMR (CDCl₃ and D₂O) δ (ppm): 7.19-7.05 (m, 1H), 6.52-6.33 (m, 3H), 4.48-4.32 (m, 1H), 3.68-3.15 (m, 4H), 2.16-1.81 (m, 5H), 1.72-1.61 (m, 1H), 1.48 (s, 9H); MS (ESI): m/z: 252 [M−56+H]⁺.

tert-Butyl 4-[3-(2-bromoethoxy)phenoxy]azepane-1-carboxylate 0.13 g of tert-butyl 3-[[4-(2-bromoethoxy)phenoxy]methyl]pyrrolidine-1-carboxylate was prepared according to the procedure for Intermediate 9, step 2, starting from 0.19 g (0.61 mmol) of tert-butyl 4-(3-hydroxyphenoxy)azepane-1-carboxylate and 0.12 g (0.90 mmol, 0.067 mL) of 2-bromoethanol (yield: 51%). ¹H NMR (CDCl₃) δ (ppm): 7.23-7.14 (m, 1H), 6.55-6.48 (m, 2H), 6.48-6.44 (m, 1H), 4.48-4.38 (m, 1H), 4.28 (t, J=6.4 Hz, 2H), 3.64 (t, J=6.1 Hz, 2H), 3.60-3.20 (m, 4H), 2.13-1.86 (m, 5H), 1.71-1.60 (m, 1H), 1.49 (s, 9H); MS (ESI): m/z: 358 [M−56+H]⁺.

Intermediate 14: tert-Butyl 4-[4-(2-bromoethoxy)phenoxy]azepane-1-carboxylate

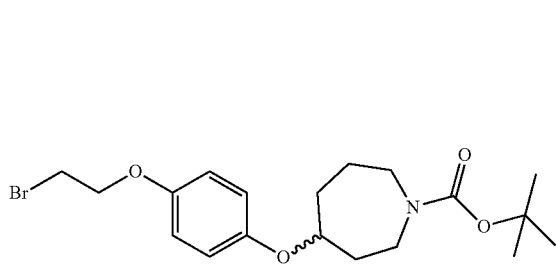 [SMILES: CC(C)(C)OC(=O)N1CCCC(Oc2ccc(OCCBr)cc2)CC1]

tert-Butyl 4-(4-benzyloxyphenoxy)azepane-1-carboxylate 0.74 g of tert-butyl 4-(4-benzyloxyphenoxy)azepane-1-carboxylate was prepared according to the procedure for Intermediate 9, step 1, starting from 0.60 g (3.0 mmol) of 4-benzyloxyphenol and 0.97 g (4.5 mmol) of tert-butyl 4-hydroxyazepane-1-carboxylate (Sigma-Aldrich, Cat. No. CDS009029) (yield: 62%). $^1$H NMR (CDCl$_3$) δ (ppm): 7.46-7.42 (m, 2H), 7.42-7.37 (m, 2H), 7.36-7.31 (m, 1H), 6.92-6.80 (m, 4H), 5.02 (s, 2H), 4.37-4.26 (m, 1H), 3.65-3.23 (m, 4H), 2.09-1.84 (m, 5H), 1.70-1.59 (m, 1H), 1.48 (s, 9H); MS (ESI): m/z: 342 [M−56+H]$^+$.

tert-Butyl 4-(4-hydroxyphenoxy)azepane-1-carboxylate 0.51 g of tert-butyl 4-(4-hydroxyphenoxy)azepane-1-carboxylate was prepared according to the procedure for Intermediate 10, step 2, starting from 0.71 g (1.8 mmol) of tert-butyl 4-(4-benzyloxyphenoxy)azepane-1-carboxylate (yield: 92%). $^1$H NMR (CDCl$_3$) δ (ppm): 6.82-6.72 (m, 4H), 4.58 (bs, 1H), 4.36-4.25 (m, 1H), 3.65-3.22 (m, 4H), 2.12-1.83 (m, 5H), 1.70-1.59 (m, 1H), 1.48 (s, 9H); MS (ESI): m/z: 252 [M−56+H]$^+$.

tert-Butyl 4-[4-(2-bromoethoxy)phenoxy]azepane-1-carboxylate 0.22 g of tert-butyl 4-[4-(2-bromoethoxy)phenoxy]azepane-1-carboxylate was prepared according to the procedure for Intermediate 9, step 2, starting from 0.354 g (1.15 mmol) of tert-butyl 4-(4-hydroxyphenoxy)azepane-1-carboxylate and 0.227 g (1.73 mmol, 0.129 mL) of 2-bromoethanol (yield: 47%). $^1$H NMR (CDCl$_3$) δ (ppm): 6.92-6.76 (m, 4H), 4.38-4.29 (m, 1H), 4.25 (t, J=6.4 Hz, 2H), 3.67-3.22 (m, 6H), 2.11-1.84 (m, 5H), 1.70-1.59 (m, 1H), 1.48 (s, 9H); MS (ESI): m/z: 358 [M−56+H]$^+$.

Intermediate 15: tert-Butyl 3-[[4-(3-bromopropyl)phenoxy]methyl]pyrrolidine-1-carboxylate

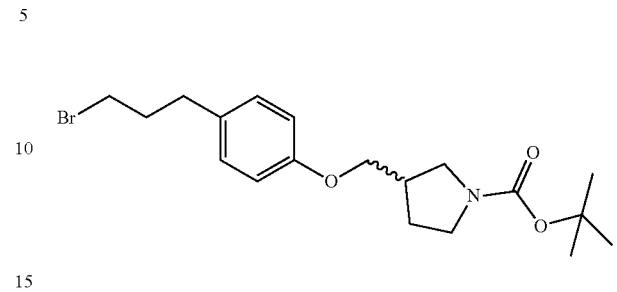

0.37 g of tert-butyl 3-[[4-(3-bromopropyl)phenoxy]methyl]pyrrolidine-1-carboxylate was prepared according to the procedure for Intermediate 5, step 1, starting from 0.39 g (1.8 mmol) of 4-(3-bromopropyl)phenol (U.S. Pat. No. 5,204,018) and 0.57 g (2.7 mmol) of tert-butyl 3-(hydroxymethyl)pyrrolidine-1-carboxylate (Fluorochem, Cat. No. 048620) (yield: 52%). $^1$H NMR (CDCl$_3$) δ (ppm): 7.16-7.07 (m, 2H), 6.87-6.78 (m, 2H), 3.95-3.85 (m, 2H), Part AB of ABX System: VA=3.6, VB=3.21, JAB=10.9 Hz, JAX=7.6 Hz, JBX=6.8 Hz, 3.52-3.44 (m, 1H), 3.42-3.33 (m, 3H), 2.76-2.62 (m, 3H), 2.17-2.03 (m, 3H), 1.85-1.75 (m, 1H), 1.47 (s, 9H); MS (ESI): m/z: 342 [M−56+H]$^+$.

Intermediate 16: tert-Butyl 4-[[4-(3-bromopropyl)phenoxy]methyl]piperidine-1-carboxylate

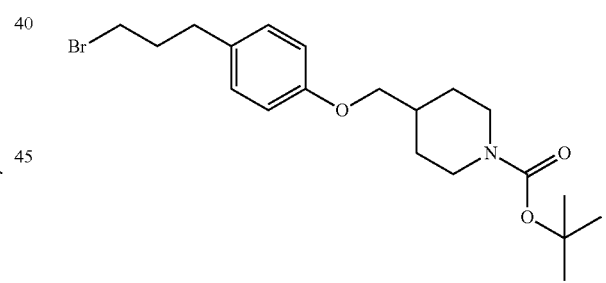

0.28 g of tert-butyl 4-[[4-(3-bromopropyl)phenoxy]methyl]piperidine-1-carboxylate was prepared according to the procedure for Intermediate 5, step 1, starting from 0.20 g (0.91 mmol) of 4-(3-bromopropyl)phenol (U.S. Pat. No. 5,204,018) and 0.29 g (1.36 mmol) of tert-butyl 4-(hydroxymethyl)piperidine-1-carboxylate (Sigma-Aldrich, Cat. No. 556017) (yield: 76%). $^1$H NMR (CDCl$_3$) δ (ppm): 7.17-7.07 (m, 2H), 6.87-6.76 (m, 2H), 4.21-4.11 (m, 2H), 3.79 (d, J=6.4 Hz, 2H), 3.39 (t, J=6.6 Hz, 2H), 2.83-2.69 (m, 4H), 2.19-2.09 (m, 2H), 2.01-1.90 (m, 1H), 1.88-1.76 (m, 2H), 1.47 (s, 9H), 1.34-1.19 (m, 2H); MS (ESI): m/z: 356 [M−56+H]$^+$.

Intermediate 17: tert-Butyl 4-[4-(3-bromopropyl) phenoxy]piperidine-1-carboxylate

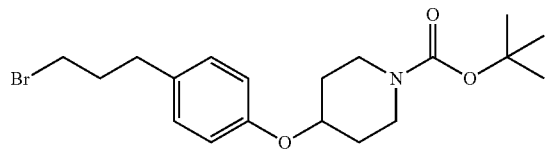 [SMILES: CC(C)(C)OC(=O)N1CCC(Oc2ccc(CCCBr)cc2)CC1]

0.327 g tert-Butyl 4-[4-(3-bromopropyl)phenoxy]piperidine-1-carboxylate was prepared according to the procedure for Intermediate 5, step 1, starting from 0.215 g (1 mmol) of 4-(3-bromopropyl)phenol (U.S. Pat. No. 5,204,018) and 0.300 g (1.50 mmol) of tert-butyl 4-hydroxypiperidine-1-carboxylate (Apollo, Cat. No. OR5404) (yield: 82%). $^1$H NMR (CDCl$_3$) δ (ppm): 7.17-7.08 (m, 2H), 6.89-6.81 (m, 2H), 4.49-4.38 (m, 1H), 3.78-3.65 (m, 2H), 3.40 (t, J=6.6 Hz, 2H), 3.37-3.30 (m, 2H), 2.73 (t, J=7.3 Hz, 2H), 2.18-2.10 (m, 2H), 1.95-1.87 (m, 2H), 1.80-1.69 (m, 2H), 1.47 (s, 9H); MS (ESI): m/z: 342 [M−56+H]$^+$.

Intermediate 18: tert-Butyl 4-[4-(3-bromopropyl) phenoxy]azepane-1-carboxylate

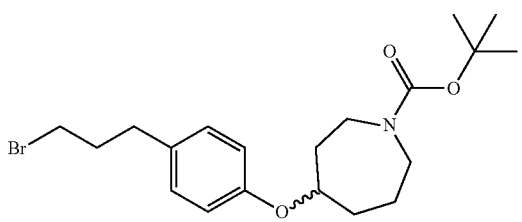 [SMILES: CC(C)(C)OC(=O)N1CCCC(Oc2ccc(CCCBr)cc2)CC1]

0.28 g of tert-butyl 4-[4-(3-bromopropyl)phenoxy]azepane-1-carboxylate was prepared according to the procedure for Intermediate 5, step 1, starting from 0.20 g (0.91 mmol) of 4-(3-bromopropyl)phenol (U.S. Pat. No. 5,204,018) and 0.29 g (1.4 mmol) of tert-butyl 4-hydroxyazepane-1-carboxylate (Intermediate 14, Step 2) (yield: 75%). $^1$H NMR (CDCl$_3$) δ (ppm): 7.14-7.07 (m, 2H), 6.85-6.77 (m, 2H), 4.45-4.38 (m, 1H), 3.65-3.24 (m, 6H), 2.72 (t, J=7.3 Hz, 2H), 2.18-2.10 (m, 2H), 2.10-2.02 (m, 1H), 1.99-1.85 (m, 4H), 1.70-1.59 (m, 1H), 1.48 (s, 9H); MS (ESI): m/z: 356 [M−56+H]$^+$.

Intermediate 19: tert-Butyl 4-[[4-(3-bromopropyl)-2-[(1-tert-butoxycarbonyl-4-piperidyl)methoxy]phenoxy]methyl]piperidine-1-carboxylate

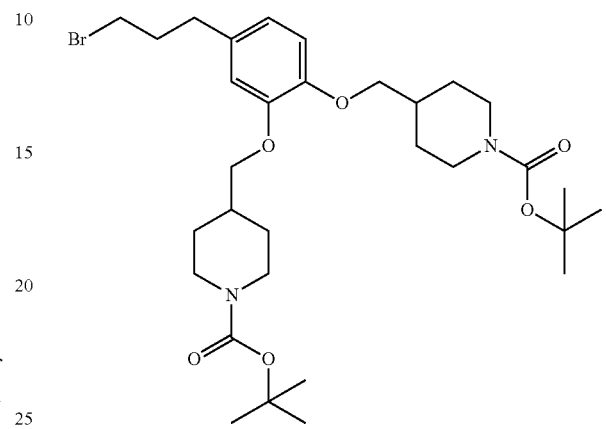

tert-butyl 4-[[2-[(1-tert-butoxycarbonyl-4-piperidyl) methoxy]-4-(3-hydroxypropyl)phenoxy]methyl]piperidine-1-carboxylate 0.079 g (0.47 mmol) of 4-(3-hydroxypropyl)benzene-1,2-diol (Yang, J. et al. Biorg. Med. Chem Lett. 2014, 24, 2680-2684), 0.03 g (0.2 mmol) of NaI and 0.61 g (1.9 mmol) of Cs$_2$CO$_3$ were suspended in 1.5 mL dry DMF under nitrogen atmosphere. 0.46 g (1.6 mmol) of tert-butyl 4-(bromomethyl)piperidine-1-carboxylate (Sigma-Aldrich, Cat. No. 796719) in 0.8 mL dry DMF was added and the suspension was stirred at 80° C. for 7 h.

The mixture was cooled down to RT and a further portion of NaI (0.014 g, 0.09 mmol), Cs$_2$CO$_3$ (0.23 g, 0.72 mmol) and tert-butyl 4-(bromomethyl)piperidine-1-carboxylate (0.2 g, 0.72 mmol) were added. The resulting mixture was heated at 80° C. overnight, then cooled down to RT and a saturated aqueous NH$_4$Cl solution and EtOAc were added. The organic phase was separated, dried over Na$_2$SO$_4$ and purified by column chromatography over silica gel (eluent: hexane/acetone, 0% to 18% of acetone (by volume)) providing 148 mg (yield: 56%) of tert-butyl 4-[[2-[(1-tert-butoxycarbonyl-4-piperidyl)methoxy]-4-(3-hydroxypropyl) phenoxy]methyl]piperidine-1-carboxylate as a pale yellow oil. $^1$H NMR (CDCl$_3$) δ (ppm): 6.85-6.69 (m, 3H), 4.22-4.08 (m, 4H), 3.86-3.78 (m, 4H), 3.69 (t, J=7.3 Hz, 2H), 2.82-2.71 (m, 4H), 2.65 (t, J=7.3 Hz, 2H), 2.06-1.94 (m, 2H), 1.92-1.78 (m, 6H), 1.48 (s, 9H), 1.47 (s, 9H), 1.33-1.19 (m, 4H); MS (ESI): m/z: 585 [M+Na]$^+$.

tert-butyl 4-[[4-(3-bromopropyl)-2-[(1-tert-butoxycarbonyl-4-piperidyl)methoxy]phenoxy]methyl]piperidine-1-carboxylate A solution of 0.11 g (0.31 mmol) CBr$_4$ in 0.75 mL CH$_2$Cl$_2$ was added dropwise at −18° C. to a solution of 0.144 g (0.256 mmol) of tert-butyl 4-[[2-[(1-tert-butoxycarbonyl-4- piperidyl)methoxy]-4-(3-hydroxypropyl)phenoxy]methyl]piperidine-1-carboxylate and 0.081 g (0.31 mmol) of PPh₃ in 1.75 mL CH₂Cl₂. The reaction mixture was stirred at RT for 4 h. Then, the solution was concentrated and the residue was purified by column chromatography eluent: hexane/acetone, 0% to 7% of acetone (by volume)) affording 118 mg (yield: 74%) of tert-butyl 4-[[4-(3-bromopropyl)-2-[(1-tert-butoxycarbonyl-4-piperidyl)methoxy]phenoxy]methyl]piperidine-1-carboxylate as a pale yellow oil. $^1$H NMR (CDCl₃) δ (ppm): 6.85-6.67 (m, 3H), 4.24-4.05 (m, 4H), 3.87-3.75 (m, 4H), 3.39 (t, J=6.6 Hz, 2H), 2.83-2.63 (m, 6H), 2.19-2.10 (m, 2H), 2.05-1.93 (m, 2H), 1.88-1.79 (m, 4H), 1.48 (s, 9H), 1.47 (s, 9H), 1.32-1.18 (m, 4H); MS (ESI): m/z: 647 [M+Na]$^+$.

Intermediate 20: tert-Butyl 4-[4-(2-bromoethyl)phenoxy]piperidine-1-carboxylate

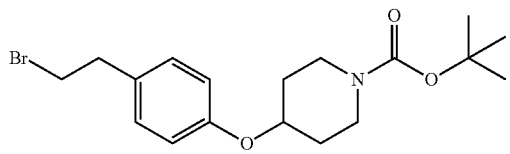 [SMILES: CC(C)(C)OC(=O)N1CCC(Oc2ccc(CCBr)cc2)CC1]

0.56 g of tert-butyl 4-[4-(2-bromoethyl)phenoxy]piperidine-1-carboxylate was prepared according to the procedure for Intermediate 5, step 1, starting from 0.40 g (2.0 mmol) of 4-(2-bromoethyl)phenol (Fluorochem, Cat. No. 233801) and 0.61 g (3.0 mmol) of tert-butyl 4-hydroxypiperidine-1-carboxylate (Apollo, Cat. No. OR5404) (yield: 73%). $^1$H NMR (CDCl₃) δ (ppm): 7.18-7.08 (m, 2H), 6.91-6.81 (m, 2H), 4.50-4.37 (m, 1H), 3.76-3.65 (m, 2H), 3.54 (t, J=7.6 Hz, 2H), 3.39-3.28 (m, 2H), 3.11 (t, J=7.6 Hz, 2H), 1.99-1.85 (m, 2H), 1.80-1.68 (m, 2H), 1.48 (s, 9H); MS (ESI): m/z: 328 [M−56+H]$^+$.

Intermediate 21: tert-Butyl 4-[[4-(2-bromoethyl)phenoxy]methyl]piperidine-1-carboxylate

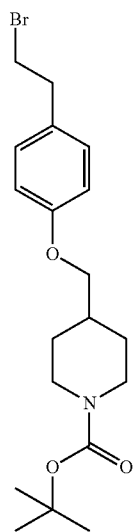

0.39 g of tert-butyl 4-[4-(2-bromoethyl)phenoxy]methyl]piperidine-1-carboxylate was prepared according to the procedure for Intermediate 5, step 1, starting from 0.30 g (1.5 mmol) of 4-(2-bromoethyl)phenol (Fluorochem, Cat. No. 233801) and 0.48 g (2.25 mmol) of tert-butyl 4-(hydroxymethyl)piperidine-1-carboxylate (Sigma-Aldrich, Cat. No. 556017) (yield: 65%). $^1$H NMR (CDCl₃) δ (ppm): 7.17-7.09 (m, 2H), 6.88-6.78 (m, 2H), 4.23-4.07 (m, 2H), 3.79 (d, J=6.4 Hz, 2H), 3.54 (t, J=7.6 Hz, 2H), 3.11 (t, J=7.6 Hz, 2H), 2.80-2.70 (m, 2H), 2.01-1.89 (m, 1H), 1.87-1.79 (m, 2H), 1.47 (s, 9H), 1.32-1.22 (m, 2H); MS (ESI): m/z: 342 [M−56+H]$^+$.

Intermediate 22: tert-Butyl 4-[[4-(2-bromoethyl)phenoxy]ethyl]piperidine-1-carboxylate

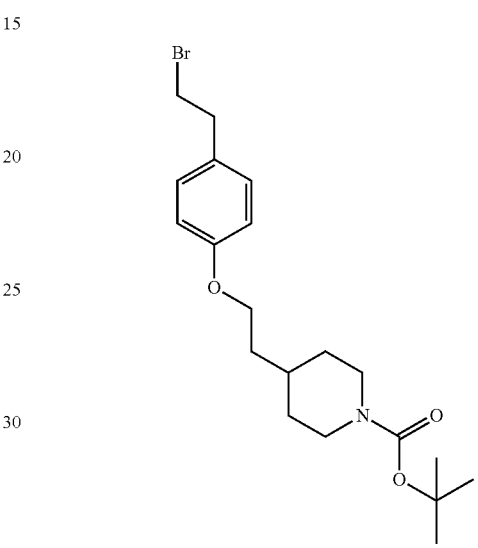

0.52 g of tert-butyl 4-[4-(2-bromoethyl)phenoxy]ethyl]piperidine-1-carboxylate was prepared according to the procedure for Intermediate 5, step 1, starting from 0.27 g (1.32 mmol) of 4-(2-bromoethyl)phenol (Fluorochem, Cat. No. 233801) and 0.47 g (1.98 mmol) of tert-butyl 4-(hydroxyethyl)piperidine-1-carboxylate (Sigma-Aldrich, Cat. No. 547247) (yield: 96%). $^1$H NMR (CDCl₃) δ (ppm): 7.17-7.09 (m, 2H), 6.88-6.81 (m, 2H), 4.16-4.05 (m, 2H), 4.00 (t, J=6.1 Hz, 2H), 3.54 (t, J=7.8 Hz, 2H), 3.11 (t, J=7.8 Hz, 2H), 2.76-2.65 (m, 2H), 1.77-1.65 (m, 5H), 1.47 (s, 9H), 1.23-1.12 (m, 2H); MS (ESI): m/z: 356 [M−56+H]$^+$.

Intermediate 23: tert-Butyl-(1H-indol-7-yloxy)-dimethyl-silane

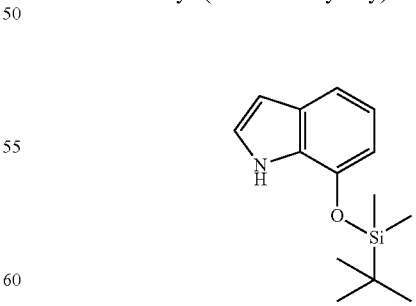

0.307 mL (2.2 mmol) of TEA and 0.01 g (0.8 mmol) of DMAP were added to an ice-cooled solution of 0.28 g (2.0 mmol) of 1H-indol-7-ol in 30 mL of dry CH₂Cl₂. After 10 min 0.34 mg (2.2 mmol) of TBDMSCl were added and the mixture was allowed to warm to RT and stirred overnight.

Then water was added (50 mL) and the reaction mixture was extracted with CH$_2$Cl$_2$ (3×100 mL). The combined organic phases were dried over Na$_2$SO$_4$, filtered, concentrated and purified by column chromatography (eluent: hexane/acetone, 0% to 5% of acetone (by volume)) to afford 403 mg (yield: 81%) of tert-butyl-(1H-indol-7-yloxy]-dimethyl-silane as a pale yellow oil. $^1$H NMR (DMSO-d$_6$) δ (ppm): 10.78-10.62 (b s, 1H), 7.28-7.22 (m, 1H), 7.15-7.09 (m, 1H), 6.86-6.79 (m, 1H), 6.56-6.50 (m, 1H), 6.41-6.36 (m, 1H), 1.00 (s, 9H), 0.25 (s, 6H); MS (ESI): m/z: 248 [M+H]$^+$.

Intermediate 24: [7-[tert-Butyl(dimethyl)silyl]oxy-1H-indol-3-yl]-(4-methylthieno[3,2-b]pyrrol-5-yl)methanone

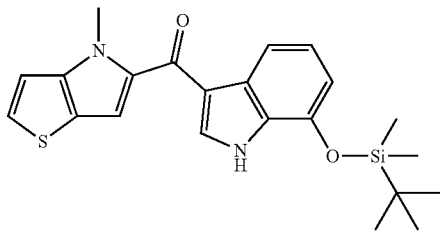 [SMILES: Cn1c(C(=O)c2c[nH]c3c(O[Si](C)(C)C(C)(C)C)cccc23)cc2sccc21]

0.13 mL (1.79 mmol) of SOCl$_2$ and 3 drops of DMF were added to a solution of 0.25 g (1.4 mmol) of 4-methylthieno[3,2-b]pyrrole-5-carboxylic acid (Intermediate 1) in 4 mL of THF and the mixture was heated to reflux for about 3 h. Then, the solvent was evaporated and the formed acyl chloride was used in the next step without any further purification.

0.660 mL of a 300 M methyl magnesium bromide solution in Et$_2$O were slowly added to an ice-cooled solution of 0.376 g (1.52 mmol) of tert-butyl-(1H-indol-7-yloxy]-dimethyl-silane in 3 mL of Et$_2$O under nitrogen atmosphere. The reaction mixture was allowed to reach RT, stirred for 2 h and then again cooled down to 0° C. A solution of (quantity) of 4-methylthieno[3,2-b]pyrrole-5-carbonyl chloride in 5 mL of Et$_2$O was added and the resulting mixture was warmed up to RT and stirred for 2 h followed by slow addition of 6 mL of a saturated NH$_4$Cl solution. The mixture was stirred at RT for a further 1 h and then partitioned between CH$_2$Cl$_2$ and water. The combined organic phases were dried over Na$_2$SO$_4$, filtered, concentrated and purified by column chromatography (eluent: hexane/acetone, 0% to 12% of acetone (by volume)) to afford 160 mg (yield: 28%) of [7-[tert-butyl(dimethyl)silyl]oxy-1H-indol-3-yl]-(4-methylthieno[3,2-b]pyrrol-5-yl)methanone as a beige solid. $^1$H NMR (CDCl$_3$) δ (ppm): 8.54 (b s, 1H), 7.99-7.96 (m, 1H), 7.86-7.83 (m, 1H), 7.37 (d, J=5.4 Hz, 1H), 7.18-7.13 (m, 1H), 7.05 (s, 1H), 7.02 (d, J=5.4 Hz, 1H), 6.78-6.73 (m, 1H), 4.13 (s, 3H), 1.06 (s, 9H), 0.32 (s, 6H); MS (ESI): m/z: 411 [M+H]$^+$.

Intermediate 25: tert-Butyl 3-[[2-[2-[3-(4-methylthieno[3,2-b]pyrrole-5-carbonyl)indol-1-yl]ethoxy]phenoxy]methyl]pyrrolidine-1-carboxylate

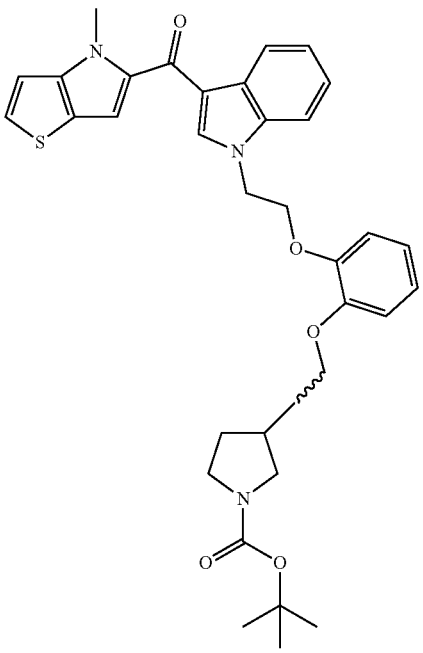 [SMILES: Cn1c(C(=O)c2cn(CCOc3ccccc3OCCC3CCN(C(=O)OC(C)(C)C)C3)c3ccccc23)cc2sccc21]

0.034 g (0.12 mmol) of 1H-indol-3-yl-(4-methylthieno[3,2-b]pyrrol-5-yl)methanone (Compound 1) were added to a suspension of 0.0058 g (0.15 mmol) of NaH (60% dispersion in mineral oil (by weight)) in dry DMF (0.5 mL) cooled down to 0° C. The mixture was stirred at 0° C. for 20 min, then a solution of 0.080 g (0.15 mmol) of tert-butyl 3-[[2-(2-bromoethoxy)phenoxy]methyl]pyrrolidine-1-carboxylate (Intermediate 4) in 1 mL of dry DMF was added at 0° C. and the mixture was stirred for 5 h at RT. The reaction was stopped by adding saturated aqueous NaHCO$_3$ solution and the product was extracted with EtOAc. The combined organic layers were dried over Na$_2$SO$_4$, filtered and evaporated to dryness. The crude product was purified by flash chromatography on silica gel (CH$_2$Cl$_2$/acetone, 0% to 4% of acetone (by volume)) to afford 0.053 g of tert-butyl 3-[[2-[2-[3-(4-methylthieno[3,2-b]pyrrole-5-carbonyl)indol-1-yl]ethoxy]phenoxy]methyl]pyrrolidine-1-carboxylate (Intermediate 25, yield: 73%) as a pale yellow solid. $^1$H NMR (CDCl$_3$) δ (ppm): 8.47-8.37 (m, 1H), 8.02 (s, 1H), 7.51-7.43 (m, 1H), 7.39-7.30 (m, 3H), 7.01 (d, J=5.4 Hz, 1H), 6.99-6.91 (m, 2H), 6.90-6.85 (m, 2H), 6.82-6.77 (m, 1H), 4.62 (t, J=4.9 Hz, 2H), 4.39 (t, J=4.9 Hz, 2H), 4.12 (s, 3H), 3.82-3.75 (m, 2H), 3.47-3.40 (m, 1H), 3.39-3.29 (m, 1H), 3.26-3.15 (m, 1H), 3.12-3.02 (m, 1H), 2.45-2.35 (m, 1H), 1.88-1.77 (m, 1H), 1.55-1.51 (m, 1H), 1.45 (s, 9H); MS (ESI): m/z: 600 [M+H]$^+$.

The following BOC-intermediates were obtained starting from Intermediates 1, 5 or 6 and the corresponding bromo derivatives according to the procedure described Intermediate 22 using as solvent DMF or DMA:

| Name | Structure | Analytical Data |
|---|---|---|
| 26 tert-butyl 3-[[3-[2-[3-(4-methylthieno[3,2-b]pyrrole-5-carbonyl)indol-1-yl]ethoxy]phenoxy]methyl]pyrrolidine-1-carboxylate | | $^1$H NMR (CDCl$_3$) δ (ppm): 8.46-8.39 (m, 1 H), 7.93 (s, 1 H), 7.50-7.44 (m, 1 H), 7.40-7.31 (m, 3 H), 7.20-7.14 (m, 1 H), 7.02 (d, J = 5.4 Hz, 1 H), 6.96 (s, 1 H), 6.54-6.44 (m, 2 H), 6.40-6.35 (m, 1 H), 4.59 (t, J = 4.9 Hz, 2 H), 4.34 (t, J = 4.9 Hz, 2 H), 4.13 (s, 3 H), 3.90-3.75 (m, 2 H), 3.61-3.54 (m, 1 H), 3.51-3.42 (m, 1 H), 3.40-3.31 (m, 1 H), 3.24-3.11 (m, 1 H), 2.70-2.57 (m, 1 H), 2.11-1.98 (m, 1 H), 1.83-1.69 (m, 1 H), 1.47 (s, 9 H); MS (ESI): m/z: 600 [M + H]$^+$. |
| 27 tert-butyl (3S)-3-[[3-[2-[3-(4-methylthieno[3,2-b]pyrrole-5-carbonyl)indol-1-yl]ethoxy]phenoxy]methyl]pyrrolidine-1-carboxylate | | $^1$H NMR (CDCl$_3$) δ (ppm): 8.44-8.39 (m, 1 H), 7.93 (s, 1 H), 7.49-7.44 (m, 1 H), 7.40-7.31 (m, 3 H), 7.20-7.15 (m, 1 H), 7.02 (d, J = 5.4 Hz, 1 H), 6.96 (s, 1 H), 6.54-6.44 (m, 2 H), 6.39-6.34 (m, 1 H), 4.59 (t, J = 5.4 Hz, 2 H), 4.34 (t, J = 5.1 Hz, 2 H), 4.13 (s, 3 H), 3.89-3.77 (m, 2 H), 3.62-3.53 (m, 1 H), 3.51-3.42 (m, 1 H), 3.41-3.30 (m, 1 H), 3.22-3.13 (m, 1 H), 2.69-2.55 (m, 1 H), 2.10-1.98 (m, 1 H), 1.83-1.71 (m, 1 H), 1.47 (s, 9 H); MS (ESI): m/z: 600 [M + H]$^+$. |

| Name | Structure | Analytical Data |
|---|---|---|
| 28 tert-butyl (3R)-3-[[3-[2-[3-(4-methylthieno[3,2-b]pyrrole-5-carbonyl)indol-1-yl]ethoxy]phenoxy]methyl]pyrrolidine-1-carboxylate | | $^1$H NMR (CDCl$_3$) δ (ppm): 8.45-8.39 (m, 1 H), 7.93 (s, 1 H), 7.49-7.44 (m, 1 H), 7.40-7.31 (m, 3 H), 7.20-7.14 (m, 1 H), 7.02 (d, J = 5.4 Hz, 1 H), 6.96 (s, 1 H), 6.53-6.44 (m, 2 H), 6.39-6.35 (m, 1 H), 4.59 (t, J = 5.1 Hz, 2 H), 4.34 (t, J = 5.1 Hz, 2 H), 4.13 (s, 3 H), 3.88-3.79 (m, 2 H), 3.61-3.53 (m, 1 H), 3.51-3.42 (m, 1 H), 3.39-3.31 (m, 1 H), 3.22-3.14 (m, 1 H), 2.69-2.59 (m, 1 H), 2.09-2.00 (m, 1 H), 1.82-1.72 (m, 1 H), 1.47 (s, 9 H); MS (ESI): m/z: 600 [M + H]$^+$. |
| 29 tert-butyl 3-[[4-[2-[3-(4-methylthieno[3,2-b]pyrrole-5-carbonyl)indol-1-yl]ethoxy]phenoxy]methyl]pyrrolidine-1-carboxylate | | $^1$H NMR (CDCl) δ (ppm): 8.47-8.37 (m, 1 H), 7.94 (s, 1 H), 7.49-7.44 (m, 1 H), 7.40-7.31 (m, 3 H), 7.02 (d, J = 5.4 Hz, 1 H), 6.97 (s, 1 H), 6.84-6.75 (m, 4 H), 4.57 (t, J = 5.4 Hz, 2 H), 4.30 (t, J = 5.1 Hz, 2 H), 4.13 (s, 3 H), 3.90-3.81 (m, 2 H), 3.61-3.54 (m, 1 H), 3.51-3.42 (m, 1 H), 3.39-3.31 (m, 1 H), 3.23-3.14 (m, 1 H), 2.69-2.56 (m, 1 H), 2.10-2.00 (m, 1 H), 1.82-1.72 (m, 1 H), 1.47 (s, 9 H); MS (ESI): m/z: 622 [M + Na]$^+$. |
| 30 tert-butyl 4-[3-[2-[3-(4-methylthieno[3,2-b]pyrrole-5-carbonyl)indol-1-yl]ethoxy]phenoxy]piperidine-1-carboxylate | | $^1$H NMR (CDCl$_3$) δ (ppm): ): 8.45-8.38 (m, 1 H), 7.93 (s, 1 H), 7.49-7.43 (m, 1 H), 7.40-7.31 (m, 3 H), 7.21-7.14 (m, 1 H), 7.02 (d, J = 5.4 Hz, 1 H), 6.96 (s, 1 H), 6.56-6.44 (m, 2 H), 6.39 (s, 1 H), 4.59 (t, J = 4.9 Hz, 2 H), 4.42-4.36 (m, 1 H), 4.33 (t, J = 4.9 Hz, 2H), 4.13 (s, 3 H), 3.71-3.58 (m, 2 H), 3.38-3.25 (m, 2 H), 1.92-1.81 (m, 2 H), 1.77-1.63 (m, 2 H), 1.47 (s, 9 H); MS (ESI): m/z: 600 [M + H]$^+$. |

| Name | Structure | Analytical Data |
|---|---|---|
| 31 tert-butyl 4-[4-[2-[3-(4-methylthieno[3,2-b]pyrrole-5-carbonyl)indol-1-yl]ethoxy]phenoxy]piperidine-1-carboxylate | 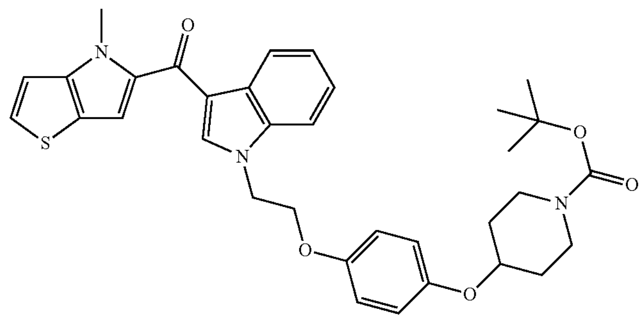 [SMILES: Cn1c(C(=O)c2cn(CCOc3ccc(OC4CCN(C(=O)OC(C)(C)C)CC4)cc3)c3ccccc23)cc2sccc21] | $^1$H NMR (CDCl$_3$) δ (ppm): 8.46-8.37 (m, 1 H), 7.95 (s, 1 H), 7.49-7.44 (m, 1 H), 7.40-7.31 (m, 3 H), 7.02 (d, J = 5.4 Hz, 1 H), 6.97 (s, 1 H), 6.87-6.82 (m, 2 H), 6.80-6.75 (m, 2 H), 4.57 (t, J = 5.1 Hz, 2 H), 4.38-4.28 (m, 3 H), 4.13 (s, 3 H), 3.73-3.63 (m, 2 H), 3.33-3.23 (m, 2 H), 1.93-1.82 (m, 2 H), 1.74-1.64 (m, 2 H), 1.47 (s, 9 H); MS (ESI): m/z: 600 [M + H]$^+$. |
| 32 tert-butyl 4-[[3-[2-[3-(4-methylthieno[3,2-b]pyrrole-5-carbonyl)indol-1-yl]ethoxy]phenoxy]methyl]piperidine-1-carboxylate | 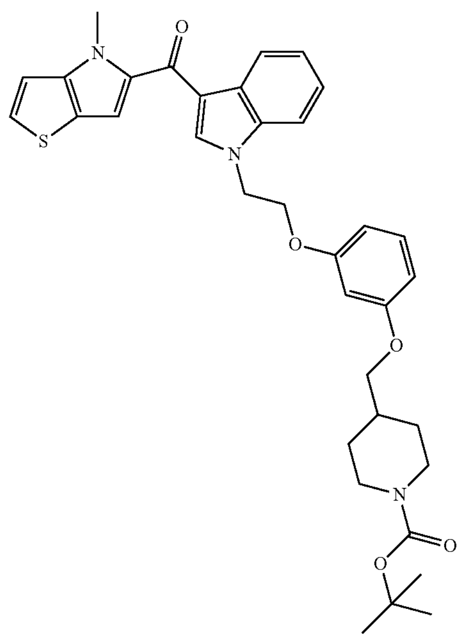 [SMILES: Cn1c(C(=O)c2cn(CCOc3cccc(OCC4CCN(C(=O)OC(C)(C)C)CC4)c3)c3ccccc23)cc2sccc21] | $^1$H NMR (CDCl$_3$) δ (ppm): 8.46-8.37 (m, 1 H), 7.93 (s, 1 H), 7.49-7.44 (m, 1 H), 7.41-7.30 (m, 3 H), 7.21-7.13 (m, 1 H), 7.02 (d, J = 5.4 Hz, 1 H), 6.96 (s, 1 H), 6.53-6.43 (m, 2 H), 6.39-6.34 (m, 1 H), 4.59 (t, J = 5.1 Hz, 2 H), 4.34 (t, J = 5.1 Hz, 2 H), 4.21-4.07 (m, 5 H), 3.72 (d, J = 6.4 Hz, 2 H), 2.80-2.64 (m, 2 H), 1.99-1.86 (m, 1 H), 1.84-1.74 (m, 2 H), 1.47 (s, 9 H), 1.31-1.18 (m, 2 H); MS (ESI): m/z: 614 [M + H]$^+$. |
| 33 tert-butyl 4-[[4-[2-[3-(4-methylthieno[3,2-b]pyrrole-5-carbonyl)indol-1-yl]ethoxy]phenoxy]methyl]piperidine-1-carboxylate | 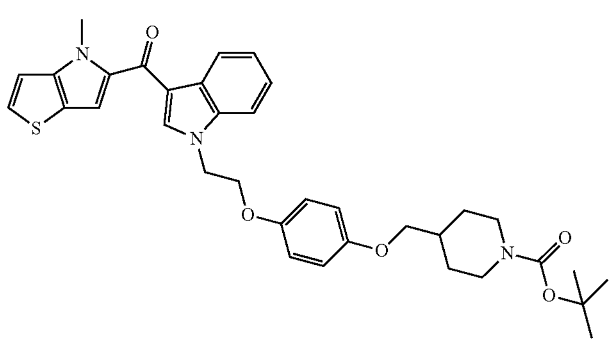 [SMILES: Cn1c(C(=O)c2cn(CCOc3ccc(OCC4CCN(C(=O)OC(C)(C)C)CC4)cc3)c3ccccc23)cc2sccc21] | $^1$H NMR (CDCl$_3$) δ (ppm): 8.46-8.39 (m, 1 H), 7.94 (s, 1 H), 7.49-7.43 (m, 1 H), 7.39-7.30 (m, 3 H), 7.02 (d, J = 5.4 Hz, 1 H), 6.97 (s, 1 H), 6.83-6.74 (m, 4 H), 4.57 (t, J = 5.4 Hz, 2 H), 4.30 (t, J = 5.1 Hz, 2 H), 4.19-4.10 (m, 5H), 3.74 (d J = 6.4 Hz, 2 H), 2.79-2.68 (m, 2 H), 1.98-1.86 (m, 1 H), 1.84-1.76 (m, 2 H), 1.47 (s, 9 H), 1.31-1.18 (m, 2 H); MS (ESI): m/z: 614 [M + H]$^+$. |

| Name | Structure | Analytical Data |
|---|---|---|
| 34 tert-butyl 4-[3-[2-[3-(4-methylthieno[3,2-b]pyrrole-5-carbonyl)indol-1-yl]ethoxy]phenoxy]azepane-1-carboxylate | | $^1$H NMR (CDCl$_3$) δ (ppm): 8.49-8.35 (m, 1 H), 7.93 (s, 1 H), 7.51-7.42 (m, 1 H), 7.41-7.31 (m, 3 H), 7.21-7.13 (m, 1 H), 7.02 (d, J = 5.4 Hz, 1 H), 6.97 (s, 1 H), 6.54-6.43 (m, 2 H), 6.39-6.32 (m, 1 H), 4.59 (t, J = 5.1 Hz, 2H), 4.42-4.30 (m, 3H) 4.12 (s, 3 H), 3.63-3.22 (m, 4 H), 2.10-1.78 (m, 5 H), 1.66-1.55 (m, 1 H), 1.47 (s, 9 H); MS (ESI): m/z: 614 [M + H]$^+$. |
| 35 tert-butyl 4-[4-[2-[3-(4-methylthieno[3,2-b]pyrrole-5-carbonyl)indol-1-yl]ethoxy]phenoxy]azepane-1-carboxylate | | $^1$H NMR (CDCl$_3$) δ (ppm): 8.49-8.31 (m, 1 H), 7.95 (s, 1 H), 7.49-7.44 (m, 1 H), 7.40-7.31 (m, 3 H), 7.03 (d, J = 5.4 Hz, 1 H), 6.98 (s, 1 H), 6.84-6.73 (m, 4 H), 4.57 (t, J = 5.1 Hz, 2 H), 4.30 (t, J = 5.1 Hz, 3 H), 4.13 (s, 3 H), 3.64-3.23 (m, 4 H), 2.07-1.98 (m, 1 H), 1.97-1.81 (m, 4 H), 1.69-1.62 (m, 1 H), 1.47 (s, 9 H); MS (ESI): m/z: 614 [M + H]$^+$. |
| 36 tert-butyl 3-[[4-[3-[3-(4-methylthieno[3,2-b]pyrrole-5-carbonyl)indol-1-yl]propyl]phenoxy]methyl]pyrrolidine-1-carboxylate | | $^1$H NMR (CDCl$_3$) δ (ppm): 8.48-8.38 (m, 1 H), 7.77 (s, 1 H), 7.39-7.31 (m, 4 H), 7.11-7.06 (m, 2 H), 7.03 (d, J = 5.4 Hz, 1 H), 7.00 (s, 1 H), 6.86-6.81 (m, 2 H), 4.20 (t, J = 7.1 Hz, 2 H), 4.13 (s, 3 H), 3.95-3.84 (m, 2 H), Part AB of ABX System: VA = 3.6, VB = 3.21, JAB = 11.3 Hz, JAX = 7.3 Hz, JBX = 6.8 Hz, 3.52-3.45 (m, 1 H), 3.42-3.33 (m, 1 H), 2.73-2.59 (m, 3 H), 2.28-2.19 (m, 2 H), 2.11-2.02 (m, 1 H), 1.86-1.74 (m, 1 H), 1.48 (s, 9 H); MS (ESI): m/z: 598 [M + H]$^+$. |
| 37 tert-butyl 4-[[4-[3-[3-(4-methylthieno[3,2-b]pyrrole-5-carbonyl)indol-1-yl]propyl]phenoxy]methyl]piperidine-1-carboxylate | | $^1$H NMR (CDCl$_3$) δ (ppm): 8.51-8.33 (m, 1 H), 7.76 (s, 1 H), 7.39-7.30 (m, 4 H), 7.11-7.06 (m, 2 H), 7.02 (d, J = 5.4 Hz, 1 H), 7.00 (s, 1 H), 6.86-6.80 (m, 2 H), 4.23-4.10 (m, 7 H), 3.79 (d, J = 6.4 Hz, 2 H), 2.79-2.71 (m, 2 H), 2.64 (t, J = 7.3 Hz, 2 H), 2.27-2.19 (m, 2 H), 2.02-1.90 (m, 1 H), 1.87-1.78 (m, 2 H), 1.47 (s, 9 H), 1.31-1.20 (m, 2 H); MS (ESI): m/z: 612 [M + H]$^+$. |

-continued

| Name | Structure | Analytical Data |
|---|---|---|
| 38 tert-butyl 4-[4-[3-[3-(4-methylthieno[3,2-b]pyrrole-5-carbonyl)indol-1-yl]propyl]phenoxy]piperidine-1-carboxylate | | ¹H NMR (CDCl₃) δ (ppm): 8.48-8.34 (m, 1 H), 7.77 (s, 1 H), 7.38-7.30 (m, 4 H), 7.11-7.05 (m, 2 H), 7.02 (d, J = 5.4 Hz, 1 H), 7.00 (s, 1 H), 6.87-6.83 (m, 2 H), 4.47-4.39 (m, 1 H), 4.20 (t, J = 7.1 Hz, 2 H), 4.13 (s, 3 H), 3.75-3.66 (m, 2 H), 3.38-3.27 (m, 2 H), 2.64 (t, J = 7.3 Hz, 2 H), 2.28-2.19 (m, 2 H), 1.96-1.85 (m, 2 H), 1.79-1.67 (m, 2 H), 1.48 (s, 9 H); MS (ESI): m/z: 598 [M + H]⁺. |
| 39 tert-butyl 4-[4-[3-[3-(4-methylthieno[3,2-b]pyrrole-5-carbonyl)indol-1-yl]propyl]phenoxy]azepane-1-carboxylate | | ¹H NMR (CDCl₃) δ (ppm): 8.48-8.37 (m, 1 H), 7.78 (s, 1 H), 7.37 (d, J = 5.4 Hz, 1 H), 7.35-7.31 (m, 3 H), 7.10-7.05 (m, 2 H), 7.03 (d, J = 5.4 Hz, 1 H), 7.00 (s, 1 H), 6.85-6.79 (m, 2 H), 4.45-4.37 (m, 1 H), 4.20 (t, J = 7.3 Hz, 2 H), 4.13 (s, 3 H), 3.63-3.26 (m, 4 H), 2.64 (t, J = 7.3 Hz, 2 H), 2.28-2.19 (m, 2 H), 2.11-2.02 (m, 1 H), 2.01-1.86 (m, 4 H), 1.70-1.61 (m, 1 H), 1.48 (s, 9 H); MS (ESI): m/z: 612 [M + H]⁺. |
| 40 tert-butyl 4-[[2-[(1-tert-butoxycarbonyl-4-piperidyl)methoxy]-4-[3-[3-(4-methylthieno[3,2-b]pyrrole-5-carbonyl)indol-1-yl]propyl]phenoxy]methyl]piperidine-1-carboxylate | | ¹H NMR (CDCl₃) δ (ppm): 8.48-8.33 (m, 1 H), 7.77 (s, 1 H), 7.39-7.30 (m, 4 H), 7.03 (d, J = 5.4 Hz, 1 H), 6.99 (s, 1 H), 6.80 (d, J = 8.3 Hz, 1 H), 6.70 (dd, J = 2.0, 8.3 Hz, 1 H), 6.63 (d, J = 2.0 Hz, 1 H), 4.20 (t, J = 6.8 Hz, 2 H), 4.17-4.09 (m, 7 H), 3.80 (d, J = 6.4 Hz, 2 H), 3.74 (d, J = 6.4 Hz, 2 H), 2.81-2.69 (m, 4 H), 2.60 (t, J = 7.3 Hz, 2 H), 2.27-2.18 (m, 2 H), 2.03-1.91 (m, 2 H), 1.87-1.76 (m, 4 H), 1.47 (s, 18 H), 1.29-1.17 (m, 4 H); MS (ESI): m/z: 825 [M + H]⁺. |
| 41 tert-butyl 4-[4-[3-[3-(4-ethylthieno[3,2-b]pyrrole-5-carbonyl)indol-1-yl]propyl]phenoxy]piperidine-1-carboxylate | | ¹H NMR (CDCl₃) δ (ppm): 8.47-8.39 (m, 1 H), 7.76 (s, 1 H), 7.38-7.30 (m, 4 H), 7.11-7.06 (m, 2 H), 7.04 (d, J = 5.4 Hz, 1 H), 698(s, 1 H), 6.88-6.82 (m, 2 H), 4.59 (q, J = 7.3 Hz, 2 H), 4.48-4.39 (m, 1 H), 4.20 (t, J = 7.3 Hz, 2 H), 3.76-3.65 (m, 2 H), 3.39-3.27 (m, 2 H), 2.64 (t, J = 7.3 Hz, 2 H), 2.28-2.20 (m, 2 H), 1.96-1.86 (m, 2 H), 1.79-1.69 (m, 2H) 1.51 (t, J = 7.1 Hz, 3 H), 1.48 (s, 9 H); MS (ESI): m/z: 612 [M + H]⁺. |

| Name | Structure | Analytical Data |
|---|---|---|
| 42 tert-butyl 3-[[4-[3-[3-(4-ethylthieno[3,2-b]pyrrole-5-carbonyl)indol-1-yl]propyl]phenoxy]methyl]pyrrolidine-1-carboxylate | | ¹H NMR (CDCl₃) δ (ppm): 8.52-8.32 (m, 1 H), 7.75 (s, 1 H), 7.38-7.30 (m, 4 H), 7.11-7.06 (m, 2 H), 7.04 (d, J = 4.9 Hz, 1 H), 6.98 (s, 1 H), 6.86-6.81 (m, 2 H), 4.59 (q, J = 7.3 Hz, 2 H), 4.19 (t, J = 7.1 Hz, 2 H), 3.97-3.84 (m, 2 H), Part AB of ABX System: VA = 3.6, VB = 3.21, JAB = 10.9 Hz, JAX = 7.6 Hz, JBX = 6.8 Hz, 3.50-3.44 (m, 1 H), 3.41-3.33 (m, 1 H), 2.72-2.60 (m, 3 H), 2.29-2.19 (m, 2 H), 2.12-2.03 (m, 1 H), 1.86-1.73 (m, 1 H), 1.51 (t J = 7.3 Hz, 3 H), 1.48 (s, 9 H); MS (ESI): m/z: 612 [M + H]⁺. |
| 43 tert-butyl 3-[[4-[3-[3-(6-methylthieno[2,3-b]pyrrole-5-carbonyl)indol-1-yl]propyl]phenoxy]methyl]pyrrolidine-1-carboxylate | | ¹H NMR (CDCl₃) δ (ppm): 8.46-8.37 (m, 1 H), 7.77 (s, 1 H), 7.37-7.30 (m, 3 H), 7.11-7.06 (m, 2 H), 7.05 (d, J = 5.4 Hz, 1 H), 6.99-6.95 (m, 2 H), 6.86-6.80 (m, 2 H), 4.20 (t, J = 7.3 Hz, 2 H), 4.10 (s, 3 H), 3.95-3.84 (m, 2 H), Part AB of ABX System: VA = 3.6, VB = 3.21, JAB = 10.8 Hz, JAX = 7.4 Hz, JBX = 6.8 Hz, 3.53-3.44 (m, 1 H), 3.41-3.33 (m, 1 H), 2.72-2.58 (m, 3 H), 2.28-2.19 (m, 2 H), 2.13-2.02 (m, 1 H), 1.85-1.74 (m, 1 H), 1.48 (s, 9 H); MS (ESI): m/z: 598 [M + H]⁺. |
| 44 tert-butyl 4-[4-[3-[3-(6-methylthieno[2,3-b]pyrrole-5-carbonyl)indol-1-yl]propyl]phenoxy]piperidine-1-carboxylate | | ¹H NMR (CDCl₃) δ (ppm): 8.49-8.33 (m, 1 H), 7.77 (s, 1 H), 7.38-7.30 (m, 3 H), 7.11-7.06 (m, 2 H), 7.05 (d, J = 5.4 Hz, 1 H), 6.99-6.95 (m, 2 H), 6.88-6.83 (m, 2 H), 4.47-4.39 (m, 1 H), 4.21 (t, J = 7.1 Hz, 2H) 4.10 (s, 3 H), 3.76-3.65 (m, 2 H), 3.37-3.28 (m, 2 H), 2.64 (t, J = 7.6 Hz, 2 H), 2.27-2.19 (m, 2 H), 1.96-1.86 (m, 2 H), 1.79-1.69 (m, 2H) 1.48 (s, 9H); MS (ESI): m/z: 598 [M + H]⁺. |
| 45 tert-butyl 4-[4-[3-[5-ethyl-3-(4-methylthieno[3,2-b]pyrrole-5-carbonyl)indol-1-yl]propyl]phenoxy]piperidine-1-carboxylate | | ¹H NMR (CDCl₃) δ (ppm): 8.32-8.22 (m, 1 H), 7.73 (s, 1 H), 7.36 (d, J = 5.4 Hz, 1 H), 7.27-7.25 (m, 1 H), 7.21-7.17 (m, 1 H), 7.10-7.05 (m, 2 H), 7.02 (d, J = 5.4 Hz, 1 H), 6.98 (s, 1 H), 6.88-6.82 (m, 2 H), 4.47-4.37 (m, 1 H), 4.18 (t, J = 7.1 Hz, 2 H), 4.13 (s, 3 H), 3.75-3.67 (m, 2 H), 3.37-3.29 (m, 2 H), 2.81 (q, J = 7.8 Hz, 2 H), 2.63 (t, J = 7.3 Hz, 2 H), 2.26-2.16 (m, 2 H), 1.96-1.86 (m, 2 H), 1.78-1.68 (m, 2 H), 1.48 (s, 9 H), 1.32 (t, J = 7.8 Hz, 3 H); MS (ESI): m/z: 626 [M + H]⁺. |

| Name | Structure | Analytical Data |
|---|---|---|
| 46 tert-butyl 4-[4-[3-[5-methyl-3-(4-methylthieno[3,2-b]pyrrole-5-carbonyl)indol-1-yl]propyl]phenoxy]piperidine-1-carboxylate | | $^1$H NMR (CDCl$_3$) δ (ppm): 8.29-8.23 (m, 1 H), 7.72 (s, 1 H), 7.36 (d, J = 5.4 Hz, 1 H), 7.25-7.21 (m, 1 H), 7.17-7.14 (m, 1 H), 7.10-7.05 (m, 2 H), 7.02 (d, J = 5.4 Hz, 1 H), 6.99 (s, 1 H), 6.88-6.82 (m, 2 H), 4.49-4.38 (m, 1 H), 4.17 (t, J = 7.1 Hz, 2 H), 4.12 (s, 3 H), 3.75-3.66 (m, 2 H), 3.37-3.28 (m, 2 H), 2.62 (t, J = 7.3 Hz, 2 H), 2.52 (s, 3 H), 2.25-2.16 (m, 2 H), 1.95-1.86 (m, 2 H), 1.79-1.68 (m, 2 H), 1.48 (s, 9 H); MS (ESI): m/z: 612 [M + H]$^+$. |
| 47 tert-butyl 4-[[4-[2-[3-(4-methylthieno[3,2-b]pyrrole-5-carbonyl)indol-1-yl]ethyl]phenoxy]methyl]piperidine-1-carboxylate | | $^1$H NMR (CDCl$_3$) δ (ppm): 8.48-8.37 (m, 1 H), 7.47-7.43 (m, 1 H), 7.40-7.32 (m, 4 H), 6.99 (d, J = 5.4 Hz, 1 H), 6.94-6.90 (m, 2 H), 6.86-6.81 (m, 2 H), 6.55 (s, 1 H), 4.40 (t, J = 6.6 Hz, 2 H), 4.20-4.12 (m, 2 H), 4.08 (s, 3 H), 3.80 (d, J = 6.4 Hz, 2 H), 3.11 (t, J = 6.6 Hz, 2 H), 2.80-2.70 (m, 2 H), 2.05-1.92 (m, 1 H), 1.87-1.78 (m, 2 H), 1.47 (s, 9 H), 1.32-1.22 (m, 2 H); MS (ESI): m/z: 598 [M + H]$^+$. |
| 48 tert-butyl 4-[4-[2-[3-(4-methylthieno[3,2-b]pyrrole-5-carbonyl)indol-1-yl]ethyl]phenoxy]piperidine-1-carboxylate | | $^1$H NMR (CDCl$_3$) δ (ppm): 8.47-8.34 (m, 1 H), 7.46-7.39 (m, 2 H), 7.38-7.31 (m, 3 H), 7.00 (d, J = 5.4 Hz, 1 H), 6.95-6.90 (m, 2 H), 6.87-6.81 (m, 2 H), 6.59 (s, 1 H), 4.48-4.31 (m, 3 H), 4.09 (s, 3 H), 3.76-3.66 (m, 2H) 3.36-3.24 (m, 2 H), 3.12 (t, J = 6.6 Hz, 2 H), 1.97-1.85 (m, 2 H), 1.81-1.68 (m, 2 H), 1.48 (s, 9 H); MS (ESI): m/z: 584 [M + H]$^+$. |

| Name Structure | | Analytical Data |
|---|---|---|
| 49 tert-butyl 4-[2-[4-[2-[3-(4-methylthieno[3,2-b]pyrrole-5-carbonyl)indol-1-yl]ethyl]phenoxy]ethyl]piperidine-1-carboxylate | 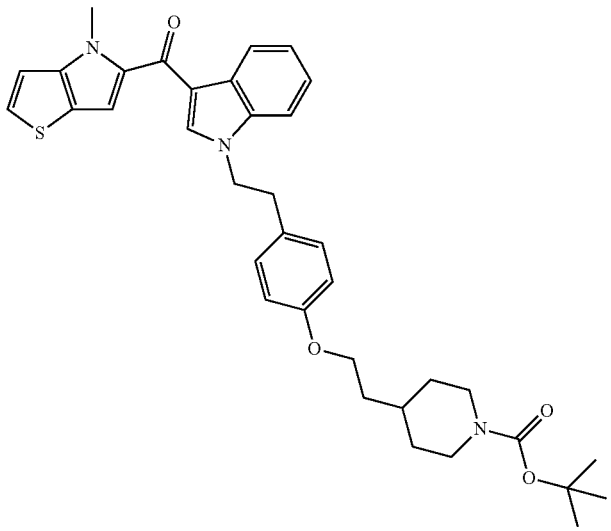 [SMILES: Cn1c(C(=O)c2cn(CCc3ccc(OCCC4CCN(C(=O)OC(C)(C)C)CC4)cc3)c3ccccc23)cc2sccc21] | $^1$H NMR (CDCl$_3$) δ (ppm): 8.49-8.34 (m, 1 H), 7.47-7.43 (m, 1 H), 7.40-7.31 (m, 4 H), 6.99 (d, J = 5.4 Hz, 1 H), 6.95-6.90 (m, 2 H), 6.86-6.81 (m, 2 H), 6.53 (s, 1 H), 4.41 (t, J = 6.6 Hz, 2 H), 4.12-4.04 (m, 5 H), 4.00 (t, J = 6.4 Hz, 2 H), 3.11 (t, J = 6.6 Hz, 2 H), 2.74-2.62 (m, 2 H), 1.80-1.65 (m, 5 H), 1.46 (s, 9 H), 1.23-1.10 (m, 2 H); MS (ESI): m/z: 612 [M + H]$^+$. |

Compound 7: (1-Methylindol-3-yl)-(4-methylthieno[3,2-b]pyrrol-5-yl)methanone

Compound 8: [1-(2-Methoxyethyl)indol-3-yl]-(4-methylthieno[3,2-b]pyrrol-5-yl)methanone

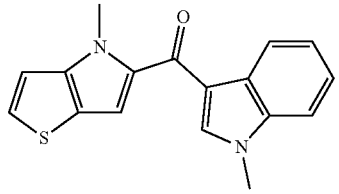 [SMILES: Cn1cc(C(=O)c2cc3sccc3n2C)c2ccccc21]

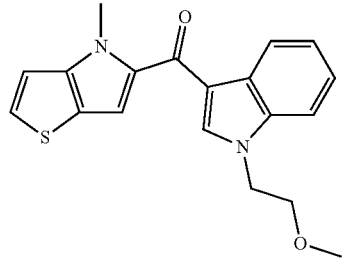 [SMILES: COCCn1cc(C(=O)c2cc3sccc3n2C)c2ccccc21]

0.016 g (0.057 mmol) of 1H-indol-3-yl-(4-methylthieno[3,2-b]pyrrol-5-yl)methanone (Compound 1) was added to a solution of 0.0027 g (0.068 mmol) of NaH in 1 mL of DMF and the mixture was stirred for 20 min. 0.0043 mL (0.068 mmol) of methyl iodide was added and the resulting mixture was stirred at RT for 30 min and then partitioned between EtOAc and water. The combined organic phases were dried over Na$_2$SO$_4$, filtered, concentrated and purified by column chromatography (eluent: hexane/acetone hexane/acetone, 85:15, v/v) to afford 9 mg (yield: 54%) of (1-methylindol-3-yl)-(4-methylthieno[3,2-b]pyrrol-5-yl)methanone as a pale yellow solid. $^1$H NMR (CDCl$_3$) δ (ppm): 8.48-8.36 (m, 1H), 7.77 (s, 1H), 7.44-7.31 (m, 4H), 7.05-6.98 (m, 2H), 4.12 (s, 3H), 3.90 (s, 3H); MS (ESI): m/z: 295 [M+H]$^+$.

0.029 g of [1-(2-methoxyethyl)indol-3-yl]-(4-methylthieno[3,2-b]pyrrol-5-yl)methanone was prepared starting from 0.034 g (0.12 mmol) of 1H-indol-3-yl-(4-methylthieno[3,2-b]pyrrol-5-yl)methanone (Compound 1) and 0.058 g (0.17 mmol, 0.016 mL) of 1-bromo-2-methoxy-ethane (Sigma-Aldrich, Cat. No. 238155) according to the procedure described for Compound 7 (yield: 71%). $^1$H NMR (CDCl$_3$) δ (ppm): 8.49-8.37 (m, 1H), 7.87 (s, 1H), 7.44-7.39 (m, 1H), 7.38-7.30 (m, 3H), 7.05-6.98 (m, 2H), 4.37 (t, J=5.4 Hz, 2H), 4.13 (s, 3H), 3.76 (t, J=5.1 Hz, 2H), 3.34 (s, 3H); MS (ESI): m/z: 339 [M+H]$^+$.

Compound 9: (4-Methylthieno[3,2-b]pyrrol-5-yl)-[1-(2-phenoxyethyl)indol-3-yl]methanone

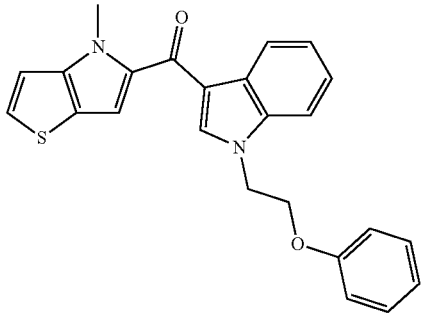 [SMILES: Cn1c(C(=O)c2cn(CCOc3ccccc3)c3ccccc23)cc2sccc21]

0.031 g of (4-methylthieno[3,2-b]pyrrol-5-yl)-[1-(2-phenoxyethyl)indol-3-yl]methanone was prepared starting from 0.034 g (0.12 mmol) of 1H-indol-3-yl-(4-methylthieno[3,2-b]pyrrol-5-yl)methanone (Compound 1) and 0.030 g (0.14 mmol) of 2-bromoethoxybenzene (Sigma-Aldrich, Cat. No. B75506-25G) according to the procedure described for Compound 7 (yield: 64%). $^1$H NMR (DMSO-d$_6$) δ (ppm): 8.31-8.17 (m, 2H), 7.76-7.67 (m, 1H), 7.60 (d, J=5.4 Hz, 1H), 7.36-7.20 (m, 5H), 7.12 (s, 1H), 6.96-6.85 (m, 3H), 4.71 (t, J=5.1 Hz, 2H), 4.38 (t, J=5.1 Hz, 2H), 4.02 (s, 3H); MS (ESI): m/z: 401 [M+H]$^+$.

Compound 10: (7-hydroxy-1H-indol-3-yl)-(4-methylthieno[3,2-b]pyrrol-5-yl)methanone

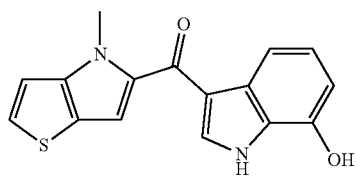 [SMILES: Cn1c(C(=O)c2c[nH]c3c(O)cccc23)cc2sccc21]

0.396 mL of a 1 M TBAF solution in THF were added at RT to a solution of 0.158 g (0.380 mmol) of [7-[tert-butyl(dimethyl)silyl]oxy-1H-indol-3-yl]-(4-methylthieno[3,2-b]pyrrol-5-yl)methanone in 3 mL of dry THF and stirred for 15 min. Then, the solvent was evaporated and the crude mixture was partitioned between EtOAc and water. The organic phase was dried over Na$_2$SO$_4$, filtered, concentrated and purified by column chromatography (eluent: hexane/acetone, 0% to 30% of acetone (by volume)) to afford 98 mg (yield: 86%) of (7-hydroxy-1H-indol-3-yl)-(4-methylthieno[3,2-b]pyrrol-5-yl)methanone as a yellow solid. $^1$H NMR (DMSO-d$_6$) δ (ppm): 11.91 (bs, 1H), 9.86 (bs, 1H), 7.92 (s, 1H), 7.70-7.63 (m, 1H), 7.56 (d, J=4.9 Hz, 1H), 7.26 (d, J=4.9 Hz, 1H), 7.12 (s, 1H), 7.02-6.93 (m, 1H), 6.68-6.58 (m, 1H), 4.00 (s, 3H); MS (ESI): m/z: 297 [M+H]$^+$.

Compound 11: (4-Methylthieno[3,2-b]pyrrol-5-yl)-[1-[2-[2-(pyrrolidin-3-ylmethoxy)phenoxy]ethyl]indol-3-yl]methanone hydrochloride

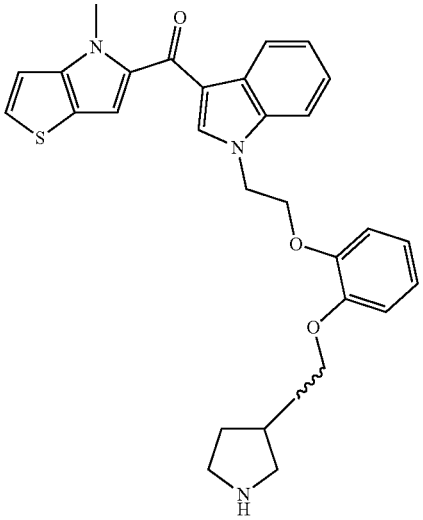 [SMILES: Cn1c(C(=O)c2cn(CCOc3ccccc3OCCC3CCNC3)c3ccccc23)cc2sccc21]

0.21 mL of 4 M HCl in dioxane was added to a solution of 0.050 g (0.083 mmol) of tert-butyl 3-[[2-[2-[3-(4-methylthieno[3,2-b]pyrrole-5-carbonyl)indol-1-yl]ethoxy]phenoxy]methyl]pyrrolidine-1-carboxylate (Intermediate 23) dissolved in 1.0 mL of dioxane and 0.2 mL of MeOH. The mixture was stirred at RT for 6 h, then the solvent was removed, the residue was taken up first in MeOH and concentrated, and then in Et$_2$O. After further concentration the solid was triturated with Et$_2$O/MeOH and dried to afford 0.042 g of (4-methylthieno[3,2-b]pyrrol-5-yl)-[1-[2-[2-(pyrrolidin-3-ylmethoxy)phenoxy]ethyl]indol-3-yl]methanone hydrochloride (yield: 87%) as a brownish powder. $^1$H NMR (DMSO-d$_6$) δ (ppm): 8.75 (bs, 2H), 8.30-8.16 (m, 2H), 7.74-7.66 (m, 1H), 7.60 (d, J=4.9 Hz, 1H), 7.38-7.21 (m, 3H), 7.13 (s, 1H), 7.02-6.83 (m, 4H), 4.71 (t, J=4.9 Hz, 2H), 4.39 (t, J=4.9 Hz, 2H), 4.02 (s, 3H), 3.81-3.70 (m, 2H), 3.21-3.03 (m, 2H), 3.02-2.90 (m, 1H), 2.88-2.76 (m, 1H), 2.46-2.33 (m, 1H), 1.87-1.75 (m, 1H), 1.59-1.43 (m, 1H); MS (ESI): m/z: 500 [M+H]$^+$.

The following compounds were obtained starting from the corresponding Boc-intermediates according to the procedure described Compound 11.

In case of the Compound 26, the compound was purified by preparative HPLC providing the product as trifluoroacetate salt. The solution was treated with a saturated aqueous NaHCO$_3$ solution, and the product was then obtained by extraction with CH$_2$Cl$_2$, drying over Na$_2$SO$_4$ and removing of the solvent in vacuo. Compounds 29 and 30 were obtained as free bases after filtration on a bicarbonate SPE cartridge (200 mg) and purification by column chromatography on silica gel (CH$_2$Cl$_2$/MeOH/NH$_3$).

| No. | Name | Structure | Analytical Data |
|-----|------|-----------|-----------------|
| 12 | (4-methylthieno[3,2-b]pyrrol-5-yl)-[1-[2-[3-(pyrrolidin-3-ylmethoxy)phenoxy]ethyl]indol-3-yl]methanone | 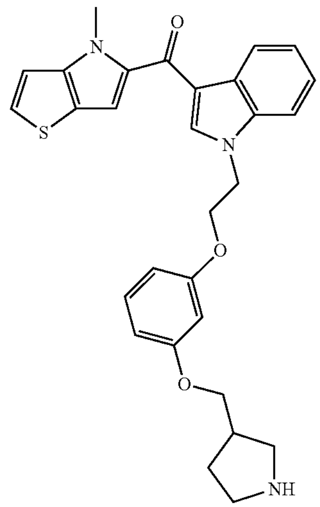 [SMILES: Cn1c(C(=O)c2cn(CCOc3cccc(OCC4CCNC4)c3)c3ccccc23)cc2sccc21] | $^1$H NMR (DMSO-d$_6$) δ (ppm): 8.84 (br. s, 2 H), 8.28-8.19 (m, 2 H), 7.75-7.68 (m, 1 H), 7.60 (d, J = 5.4 Hz, 1 H), 7.35-7.22 (m, 3 H), 7.19-7.13 (m, 1 H), 7.10 (s, 1 H), 6.54-6.48 (m, 2 H), 6.44-6.39 (m, 1 H), 4.70 (t, J = 4.9 Hz, 2 H), 4.38 (t, J = 4.9 Hz, 2 H), 4.02 (s, 3 H), 3.94-3.82 (m, 2 H), 3.30-3.27 (m, 1 H), 3.26-3.18 (m, 1 H), 3.17-3.10 (m, 1 H), 2.99-2.91 (m, 1 H), 2.71-2.60 (m, 1 H), 2.09-1.99 (m, 1 H), 1.74-1.64 (m, 1 H); MS (ESI): m/z: 500 [M + H]$^+$. |
| 13 | (4-methylthieno[3,2-b]pyrrol-5-yl)-[1-[2-[3-[[(3S)-pyrrolidin-3-yl]methoxy]phenoxy]ethyl]indol-3-yl]methanone hydrochloride | 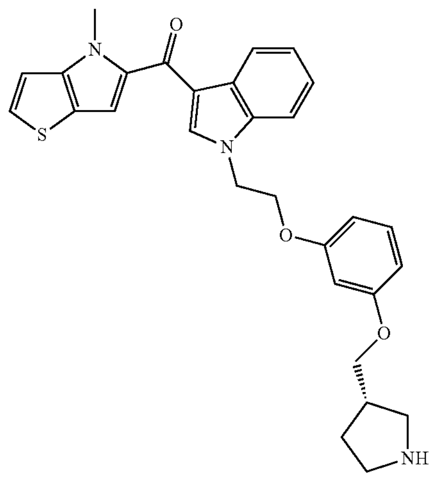 [SMILES: Cn1c(C(=O)c2cn(CCOc3cccc(OC[C@H]4CCNC4)c3)c3ccccc23)cc2sccc21] | $^1$H NMR (DMSO-d$_6$) δ (ppm): 8.78 (br. s, 2 H), 8.28-8.15 (m, 2H) 7.75-7.67 (m, 1 H), 7.60 (d, J = 5.4 Hz, 1 H), 7.35-7.22 (m, 3 H), 7.19-7.13 (m, 1 H), 7.10 (s, 1 H), 6.54-6.47 (m, 2 H), 6.44-6.38 (m, 1 H), 4.69 (t, J = 4.9 Hz, 2H), 4.37 (t, J = 4.9 Hz, 2 H), 4.02 (s, 3 H), 3.95-3.81 (m, 2 H), 3.30-3.26 (m, 1 H), 3.25-3.18 (m, 1 H), 3.17-3.10 (m, 1 H), 2.99-2.89 (m, 1 H), 2.71-2.60 (m, 1 H), 2.09-1.99 (m, 1 H), 1.75-1.63 (m, 1 H), MS (ESI): m/z: 500 [M + H]$^+$. |
| 14 | (4-methylthieno[3,2-b]pyrrol-5-yl)-[1-[2-[3-[[(3R)-pyrrolidin-3-yl]methoxy]phenoxy]ethyl]indol-3-yl]methanone hydrochloride | 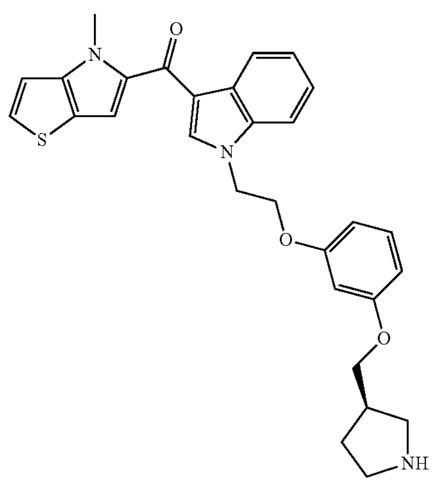 [SMILES: Cn1c(C(=O)c2cn(CCOc3cccc(OC[C@@H]4CCNC4)c3)c3ccccc23)cc2sccc21] | $^1$H NMR (DMSO-d$_6$) δ (ppm): 8.81 (br. s, 2 H), 8.28-8.19 (m, 2 H), 7.74-7.68 (m, 1 H), 7.60 (d, J = 5.4 Hz, 1 H), 7.35-7.21 (m, 3 H), 7.19-7.12 (m, 1 H), 7.10 (s, 1 H), 6.55-6.46 (m, 2 H), 6.44-6.37 (m, 1 H), 4.70 (t, J = 4.9 Hz, 2H) 4.37 (t, J = 4.9 Hz, 2 H), 4.02 (s, 3 H), 3.95-3.81 (m, 2 H), 3.30-3.27 (m, 1 H), 3.25-3.19 (m, 1 H), 3.17-3.09 (m, 1 H), 2.98-2.89 (m, 1 H), 2.71-2.61 (m, 1 H), 2.10-1.97 (m, 1 H), 1.76-1.63 (m, 1 H); MS (ESI): m/z: 500 [M + H]$^+$. |

| No. | Name | Structure | Analytical Data |
|---|---|---|---|
| 15 | (4-methylthieno[3,2-b]pyrrol-5-yl)-[1-[2-[4-(pyrrolidin-3-ylmethoxy)phenoxy]ethyl]indol-3-yl]methanone hydrochloride | 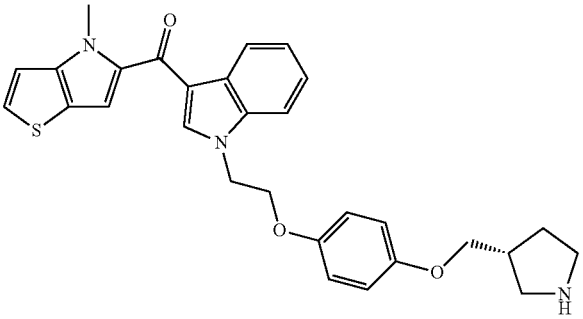 [SMILES: Cn1c(C(=O)c2cn(CCOc3ccc(OC[C@@H]4CCNC4)cc3)c3ccccc23)cc2sccc21] | $^1$H NMR (DMSO-$d_6$ + $D_2O$) δ (ppm): 8.29-8.11 (m, 2 H), 7.74-7.66 (m, 1 H), 7.59 (d, J = 5.4 Hz, 1 H), 7.34-7.21 (m, 3 H), 7.10 (s, 1 H), 6.88-6.77 (m, 4 H), 4.67 (t, J = 4.9 Hz, 2 H), 4.29 (t, J = 4.9 Hz, 2 H), 4.00 (s, 3 H), 3.93-3.78 (m, 2 H), 3.33-3.27 (m, 1 H), 3.26-3.18 (m, 1 H), 3.17-3.09 (m, 1 H), 3.02-2.90 (m, 1 H), 2.72-2.59 (m, 1 H), 2.13-1.99 (m, 1 H), 1.77-1.62 (m, 1 H); MS (ESI): m/z: 500 [M + H]$^+$. |
| 16 | (4-methylthieno[3,2-b]pyrrol-5-yl)-[1-[2-[3-(4-piperidyloxy)phenoxy]ethyl]indol-3-yl]methanone hydrochloride | 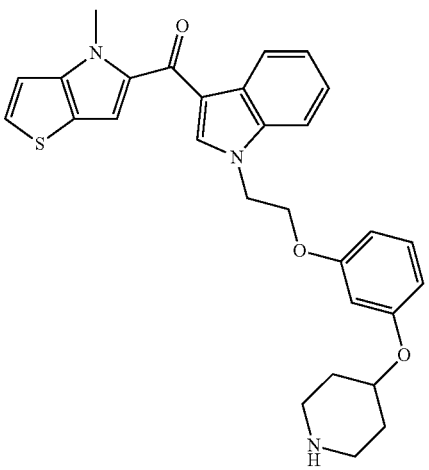 [SMILES: Cn1c(C(=O)c2cn(CCOc3cccc(OC4CCNCC4)c3)c3ccccc23)cc2sccc21] | $^1$H NMR (DMSO-$d_6$) δ (ppm): 8.48 (br. s, 2 H), 8.27-8.21 (m, 2 H), 7.73-7.69 (m, 1 H), 7.60 (d, J = 5.4 Hz, 1 H), 7.35-7.23 (m, 3 H), 7.19-7.13 (m, 1 H), 7.09 (s, 1 H), 6.59-6.48 (m, 2 H), 6.47-6.42 (m, 1 H), 4.70 (t, J = 4.9 Hz, 2 H), 4.59-4.49 (m, 1 H), 4.38 (t, J = 5.4 Hz, 2 H), 4.02 (s, 3 H), 3.22-3.11 (m, 2 H), 3.07-2.93 (m, 2 H), 2.05-1.95 (m, 2 H), 1.78-1.67 (m, 2 H); MS (ESI): m/z: 500 [M + H]$^+$. |
| 17 | (4-methylthieno[3,2-b]pyrrol-5-yl)-[1-[2-[4-(4-piperidyloxy)phenoxy]ethyl]indol-3-yl]methanone hydrochloride | 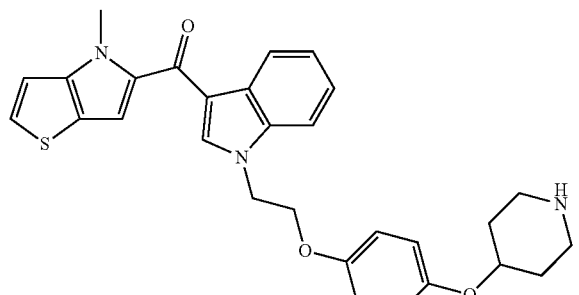 | $^1$H NMR (DMSO-$d_6$) δ (ppm): 8.42 (br. s., 2 H), 8.26-8.21 (m, 2 H), 7.74-7.67 (m, 1 H), 7.60 (d, J = 5.4 Hz, 1 H), 7.35-7.21 (m, 3 H), 7.12 (s, 1 H), 6.92-6.85 (m, 2 H), 6.84-6.78 (m, 2 H), 4.67 (t, J = 4.9 Hz, 2 H), 4.48-4.40 (m, 1 H), 4.32 (t, J = 5.4 Hz, 2 H), 4.02 (s, 3 H), 3.23-3.14 (m, 2 H), 3.06-2.94 (m, 2 H), 2.03-1.94 (m, 2 H), 1.77-1.67 (m, 2 H); MS (ESI): m/z: 500 [M + H]$^+$. |

| No. | Name | Structure | Analytical Data |
|---|---|---|---|
| 18 | (4-methylthieno[3,2-b]pyrrol-5-yl)-[1-[2-[3-(4-piperidylmethoxy)phenoxy]ethyl]indol-3-yl]methanone hydrochloride | 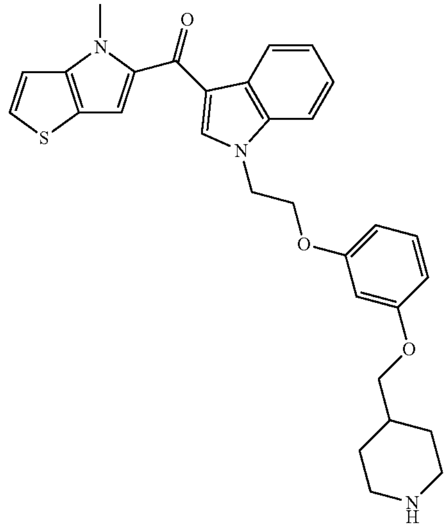 [SMILES: Cn1c(C(=O)c2cn(CCOc3cccc(OCC4CCNCC4)c3)c3ccccc23)cc2sccc21] | $^1$H NMR (DMSO-d$_6$) δ (ppm): 8.58 (br. s, 1 H), 8.34-8.15 (m, 3 H), 7.75-7.68 (m, 1 H), 7.60 (d, J = 5.4 Hz, 1 H), 7.35-7.21 (m, J = 5.4 Hz, 3 H), 7.18-7.11 (m, 1 H), 7.09 (s, 1 H), 6.51-6.45 (m, 2 H), 6.40-6.33 (m, 1 H), 4.69 (t, J = 4.9 Hz, 2 H), 4.38 (t, J = 4.9 Hz, 2 H), 4.02 (s, 3 H), 3.74 (d, J = 6.4 Hz, 2 H), 3.30-3.22 (m, 2 H), 2.93-2.79 (m, 2 H), 2.04-1.93 (m, 1 H), 1.89-1.80 (m, 2 H), 1.46-1.33 (m, 2 H); MS (ESI): m/z: 514 [M + H]$^+$. |
| 19 | (4-methylthieno[3,2-b]pyrrol-5-yl)-[1-[2-[4-(4-piperidylmethoxy)phenoxy]ethyl]indol-3-yl]methanone hydrochloride | 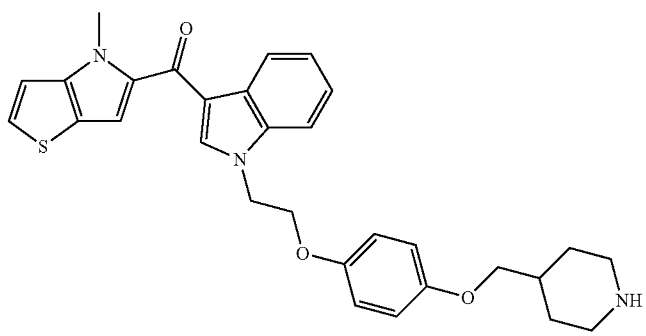 [SMILES: Cn1c(C(=O)c2cn(CCOc3ccc(OCC4CCNCC4)cc3)c3ccccc23)cc2sccc21] | $^1$H NMR (DMSO-d$_6$) δ (ppm): 8.39 (br. s, 2 H), 8.26-8.22 (m, 2 H), 7.73-7.67 (m, 1 H), 7.60 (d, J = 5.4 Hz, 1 H), 7.36-7.21 (m, 3 H), 7.11 (s, 1 H), 6.86-6.76 (m, 4 H), 4.68 (t, J = 5.4 Hz, 2 H), 4.32 (t, J = 5.4 Hz, 2 H), 4.02 (s, 3 H), 3.75 (d, J = 6.4 Hz, 2 H), 3.30-3.22 (m, 2 H), 2.93-2.77 (m, 2 H), 2.05-1.92 (m, 1 H), 1.89-1.80 (m, 2 H), 1.48-1.35 (m, 2 H); MS (ESI): m/z: 514 [M + H]$^+$. |
| 20 | [1-[2-[3-(azepan-4-yloxy)phenoxy]ethyl]indol-3-yl]-(4-methylthieno[3,2-b]pyrrol-5-yl)methanone hydrochloride | 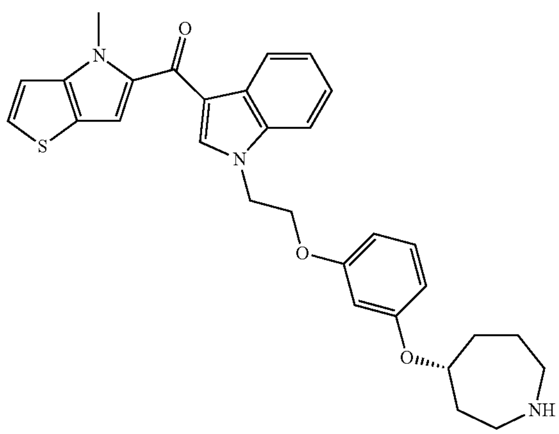 [SMILES: Cn1c(C(=O)c2cn(CCOc3cccc(O[C@@H]4CCCNCC4)c3)c3ccccc23)cc2sccc21] | $^1$H NMR (DMSO-d$_6$) δ (ppm): 8.55 (br. s, 2 H), 8.31-8.13 (m, 2 H), 7.74-7.68 (m, 1 H), 7.59 (d, J = 5.4 Hz, 1 H), 7.35-7.22 (m, 3 H), 7.18-7.11 (m, 1 H), 7.08 (s, 1 H), 6.54-6.46 (m, 2 H), 6.42-6.36 (m, 1 H), 4.69 (t, J = 4.9 Hz, 2 H), 4.63-4.54 (m, 1 H), 4.37 (t, J = 4.9 Hz, 2 H), 4.02 (s, 3 H), 3.21-2.98 (m, 4 H), 2.12-1.58 (m, 6 H); MS (ESI): m/z: 514 [M + H]$^+$. |
| 21 | [1-[2-[4-(azepan-4-yloxy)phenoxy]ethyl]indol-3-yl]-(4-methylthieno[3,2-b]pyrrol-5-yl)methanone hydrochloride | 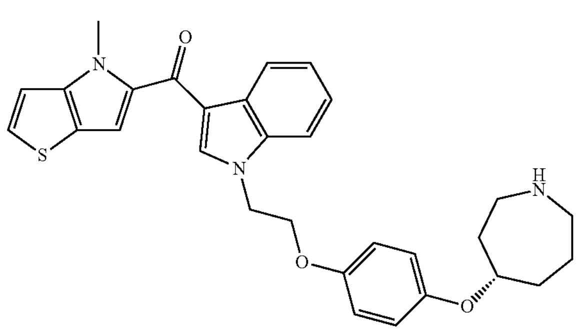 [SMILES: Cn1c(C(=O)c2cn(CCOc3ccc(O[C@H]4CCCNCC4)cc3)c3ccccc23)cc2sccc21] | $^1$H NMR (DMSO-d$_6$) δ (ppm): 8.59 (br. s, 2H), 8.29-8.19 (m, 2 H), 7.75-7.68 (m, 1 H), 7.60 (d, J = 5.4 Hz, 1 H), 7.35-7.21 (m, 3 H), 7.12 (s, 1 H), 6.88-6.71 (m, 4 H), 4.68 (t, J = 5.1 Hz, 2 H), 4.54-4.47 (m, 1 H), 4.32 (t, J = 5.1 Hz, 2 H), 4.02 (s, 3 H), 3.22-2.99 (m, 4 H), 2.12-1.57 (m, 6 H); MS (ESI): m/z: 514 [M + H]$^+$. |

| No. | Name | Structure | Analytical Data |
|---|---|---|---|
| 22 | (4-methylthieno[3,2-b]pyrrol-5-yl)-[1-[3-[4-(pyrrolidin-3-ylmethoxy)phenyl]propyl]indol-3-yl]methanone hydrochloride | 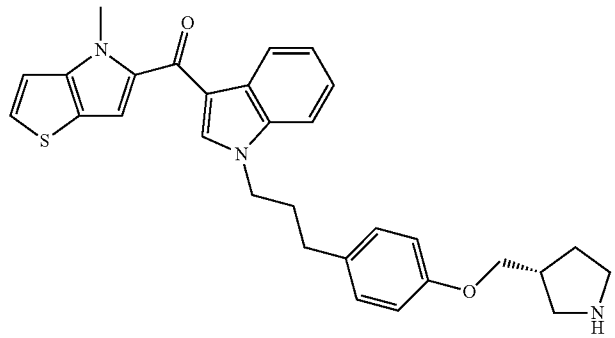 [SMILES: Cn1c(C(=O)c2cn(CCCc3ccc(OC[C@@H]4CCNC4)cc3)c3ccccc23)cc2sccc21] | $^1$H NMR (DMSO-d$_6$) δ (ppm): 8.80 (br. s, 2 H), 8.28-8.24 (m, 1 H), 8.21 (s, 1 H), 7.61-7.55 (m, 2 H), 7.32-7.22 (m, 3 H), 7.18 (s, 1 H), 7.14-7.09 (m, 2 H), 6.87-6.81 (m, 2 H), 4.31 (t, J = 7.3 Hz, 2 H), 4.02 (s, 3 H), Part AB of ABX System: VA = 3.96, VB = 3.9, JAB = 9.4 Hz, JAX = 6.1 Hz, JBX = 7.4 Hz, 3.36-3.34 (m, 1 H), 3.28-3.21 (m, 1 H), 3.19-3.11 (m, 1 H), 3.02-2.95 (m, 1 H), 2.73-2.65 (m, 1 H), 2.55 (t, J = 7.3 Hz, 2 H), 2.14-2.03 (m, 3 H), 1.77-1.67 (m, 1 H); MS (ESI): m/z: 498 [M + H]$^+$. |
| 23 | (4-methylthieno[3,2-b]pyrrol-5-yl)-[1-[3-[4-(4-piperidylmethoxy)phenyl]propyl]indol-3-yl]methanone hydrochloride | 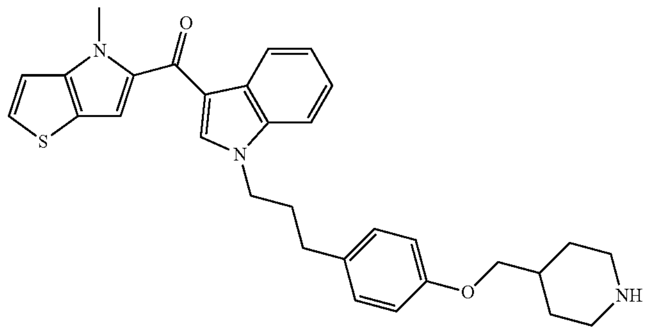 | $^1$H NMR (DMSO-d$_6$) δ (ppm): 8.64 (br. s, 1 H), 8.37-8.24 (m, 2 H), 8.21 (s, 1 H), 7.61-7.55 (m, 2 H), 7.32-7.21 (m, 3 H), 7.18 (s, 1 H), 7.13-7.07 (m, 2 H), 6.86-6.77 (m, 2 H), 4.31 (t, J = 7.3 Hz, 2 H), 4.02 (s, 3 H), 3.80 (d, J = 6.4 Hz, 2 H), 3.29-3.24 (m, 2 H), 2.95-2.80 (m, 2 H), 2.55 (t, J = 7.3 Hz, 2 H), 2.14-2.06 (m, 2 H), 2.06-1.96 (m, 1 H), 1.92-1.84 (m, 2 H), 1.50-1.38 (m, 2 H); MS (ESI): m/z: 512 [M + H]$^+$. |
| 24 | (4-methylthieno[3,2-b]pyrrol-5-yl)-[1-[3-[4-(4-piperidyloxy)phenyl]propyl]indol-3-yl]methanone hydrochloride | 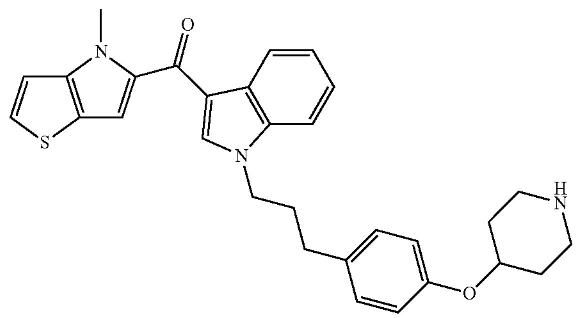 | $^1$H NMR (DMSO-d$_6$) δ (ppm): 8.57 (br. s, 2 H), 8.28-8.24 (m, 1 H), 8.22 (s, 1 H), 7.61-7.55 (m, 2 H), 7.32-7.21 (m, 3 H), 7.18 (s, 1 H), 7.14-7.08 (m, 2 H), 6.91-6.84 (m, 2 H), 4.61-4.51 (m, 1 H), 4.32 (t, J = 7.1 Hz, 2 H), 4.02 (s, 3 H), 3.25-3.15 (m, 2 H), 3.09-2.98 (m, 2 H), 2.56 (t, J = 7.3 Hz, 2 H), 2.16-1.98 (m, 4 H), 1.83-1.69 (m, 2 H); MS (ESI): m/z: 498 [M + H]$^+$. |
| 25 | [1-[3-[4-(azepan-4-yloxy)phenyl]propyl]indol-3-yl]-(4-methylthieno[3,2-b]pyrrol-5-yl)methanone hydrochloride | 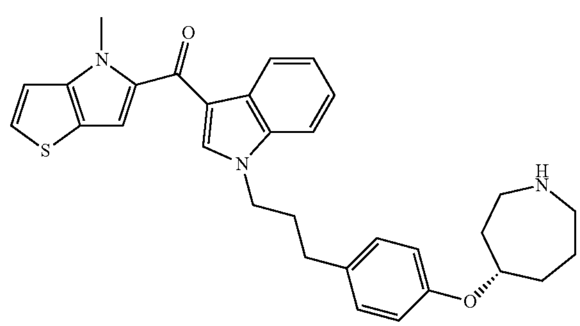 [SMILES: Cn1c(C(=O)c2cn(CCCc3ccc(O[C@H]4CCCNCC4)cc3)c3ccccc23)cc2sccc21] | $^1$H NMR (DMSO-d$_6$) δ (ppm): 8.68 (br. s, 2 H), 8.28-8.23 (m, 1 H), 8.21 (s, 1 H), 7.61-7.54 (m, 2 H), 7.31-7.21 (m, 3 H), 7.18 (s, 1 H), 7.13-7.07 (m, 2 H), 6.86-6.80 (m, 2 H), 4.67-4.55 (m, 1 H), 4.32 (t, J = 7.3 Hz, 2 H), 4.02 (s, 3 H), 3.25-3.00 (m, 4 H), 2.55 (t, J = 7.3 Hz, 2 H), 2.16-2.05 (m, 3 H), 2.03-1.93 (m, 2 H), 1.91-1.76 (m, 2 H), 1.75-1.63 (m, 1 H); MS (ESI): m/z: 512 [M + H]$^+$. |

-continued

| No. | Name | Structure | Analytical Data |
|---|---|---|---|
| 26 | [1-[3-[3,4-bis(4-piperidylmethoxy)phenyl]propyl]indol-3-yl]-(4-methylthieno[3,2-b]pyrrol-5-yl)methanone | 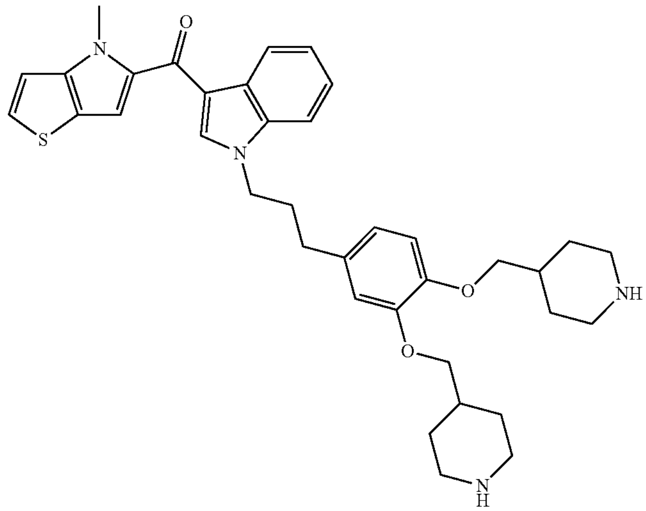 [SMILES: Cn1c(C(=O)c2cn(CCCc3ccc(OCC4CCNCC4)c(OCC4CCNCC4)c3)c3ccccc23)cc2sccc21] | $^1$H NMR (DMSO-d$_6$ +DCl 1N) δ (ppm): 8.24-8.16 (m, 1 H), 8.08 (s, 1 H), 7.59-7.48 (m, 2 H), 7.33-7.17 (m, 3 H), 7.08 (s, 1 H), 6.85-6.76 (m, 1 H), 6.71-6.61 (m, 2 H), 4.27 (t, J = 6.8 Hz, 2 H), 3.96 (s, 3H), 3.73 (d, J = 6.3 Hz, 2 H), 3.66 (d, J = 6.3 Hz, 2 H), 3.29-3.19 (m, 4 H), 2.90-2.77 (m, 4 H), 2.48-2.42 (m, 2 H), 2.14-2.03 (m, 2 H), 2.01-1.78 (m, 6 H), 1.51-1.36 (m, 4 H); MS (ESI): m/z: 625 [M + H]$^+$. |
| 27 | (4-ethylthieno[3,2-b]pyrrol-5-yl)-[1-[3-[4-(4-piperidyloxy)phenyl]propyl]indol-3-yl]methanone hydrochloride | 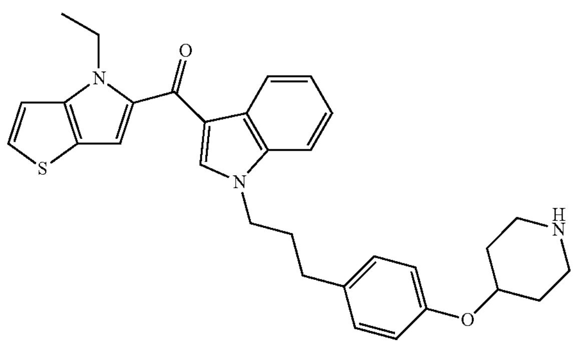 [SMILES: CCn1c(C(=O)c2cn(CCCc3ccc(OC4CCNCC4)cc3)c3ccccc23)cc2sccc21] | $^1$H NMR (DMSO-d$_6$) δ (ppm): 8.61 (br. s, 2 H), 8.28-8.23 (m, 1 H), 8.21 (s, 1 H), 7.62-7.53 (m, 2 H), 7.32-7.20 (m, 3 H), 7.16 (s, 1 H), 7.14-7.08 (m, 2 H), 6.91-6.84 (m, 2 H), 4.61-4.45 (m, 3 H), 4.31 (t, J = 7.1 Hz, 2 H), 3.26-3.13 (m, 2 H), 3.09-2.96 (m, 2 H), 2.56 (t, J = 7.3 Hz, 2 H), 2.17-1.97 (m, 4H), 1.83-1.70 (m, 2 H), 1.35 (t, J = 7.1 Hz, 3 H); MS (ESI): m/z: 512 [M + H]$^+$. |
| 28 | (4-ethylthieno[3,2-b]pyrrol-5-yl)-[1-[3-[4-(pyrrolidin-3-ylmethoxy)phenyl]propyl]indol-3-yl]methanone hydrochloride | 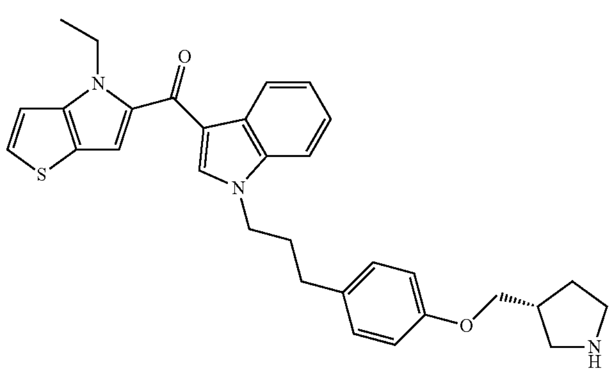 [SMILES: CCn1c(C(=O)c2cn(CCCc3ccc(OC[C@@H]4CCNC4)cc3)c3ccccc23)cc2sccc21] | $^1$H NMR (DMSO-d$_6$ + D$_2$O) δ (ppm): 8.31-8.22 (m, 1 H), 8.17 (s, 1 H), 7.60-7.51 (m, 2 H), 7.33-7.19 (m, 3 H), 7.15 (s, 1 H), 7.13-7.08 (m, 2 H), 6.86-6.81 (m, 2 H), 4.50 (q, J = 7.3 Hz, 2 H), 4.30 (t, J = 7.3 Hz, 2 H), 3.99-3.85 (m, 2 H), Part AB of ABX System: VA = 3.33, VB = 2.98, JAB = 11.8 Hz, JAX = 8.3 Hz, JBX = 7.3 Hz, 3.27-3.21 (m, 1 H), 3.19-3.11 (m, 1 H), 2.73-2.65 (m, 1 H), 2.55 (t, J = 7.8 Hz, 2 H), 2.15-2.01 (m, 3 H), 1.79-1.67 (m, 1 H), 1.34 (t, J = 7.3 Hz, 3 H); MS (ESI): m/z: 512 [M + H]$^+$. |

-continued

| No. | Name | Structure | Analytical Data |
|---|---|---|---|
| 29 | (6-methylthieno[2,3-b]pyrrol-5-yl)-[1-[3-[4-(pyrrolidin-3-ylmethoxy)phenyl]propyl]indol-3-yl]methanone | 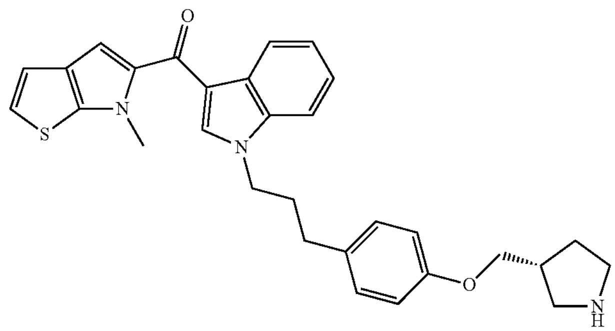 [SMILES: Cn1c(C(=O)c2cn(CCCc3ccc(OC[C@@H]4CCNC4)cc3)c3ccccc23)cc2ccsc21] | $^1$H NMR (CDCl$_3$) δ (ppm): 8.50-8.31 (m, 1 H), 7.76 (s, 1 H), 7.39-7.30 (m, 3 H), 7.11-7.02 (m, 3 H), 6.99-6.92 (m, 2 H), 6.86-6.81 (m, 2 H), 4.20 (t, J = 7.1 Hz, 2 H), 4.10 (s, 3 H), 3.97-3.80 (m, 2 H), Part AB of ABX System: VA = 3.92, VB = 3.86, JAB = 9.1 Hz, JAX = 5.8 Hz, JBX=7.4 Hz, Part AB of ABX System: VA = 3.25, VB = 2.94, JAB = 11.4 Hz, JAX = 7.9 Hz, JBX = 6.1 Hz, 3.19-3.12 (m, 1 H), 3.09-3.01 (m, 1 H), 2.67-2.61 (m, 3 H), 2.27-2.17 (m, 2 H), 2.11-2.01 (m, 1 H), 1.75-1.60 (m, 1 H); MS (ESI): m/z: 498 [M + H]$^+$. |
| 30 | (6-methylthieno[2,3-b]pyrrol-5-yl)-[1-[3-[4-(4-piperidyloxy)phenyl]propyl]indol-3-yl]methanone | 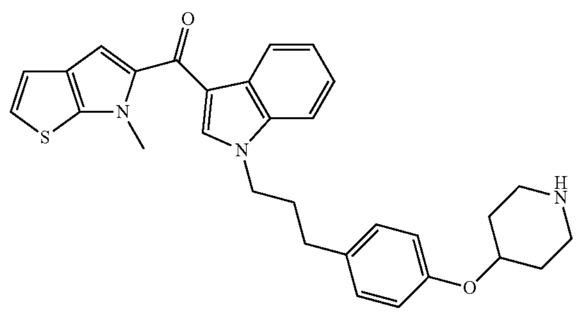 [SMILES: Cn1c(C(=O)c2cn(CCCc3ccc(OC4CCNCC4)cc3)c3ccccc23)cc2ccsc21] | $^1$H NMR (CDCl$_3$) δ (ppm): 8.48-8.36 (m, 1 H), 7.77 (s, 1 H), 7.38-7.30 (m, 3 H), 7.11-7.06 (m, 2 H), 7.05 (d, J = 4.9 Hz, 1 H), 6.99-6.95 (m, 2 H), 6.87-6.82 (m, 2 H), 4.45-4.35 (m, 1 H), 4.20 (t, J = 7.1 Hz, 2 H), 4.10 (s, 3 H), 3.25-3.15 (m, 2 H), 2.91-2.80 (m, 2 H), 2.64 (t, J = 7.3 Hz, 2 H), 2.29-2.18 (m, 2 H), 2.12-2.02 (m, 2 H), 1.84-1.71 (m, 2 H); MS (ESI): m/z: 498 [M + H]$^+$. |
| 31 | [5-ethyl-1-[3-[4-(4-piperidyloxy)phenyl]propyl]indol-3-yl]-(4-methylthieno[3,2-b]pyrrol-5-yl)methanone hydrochloride | 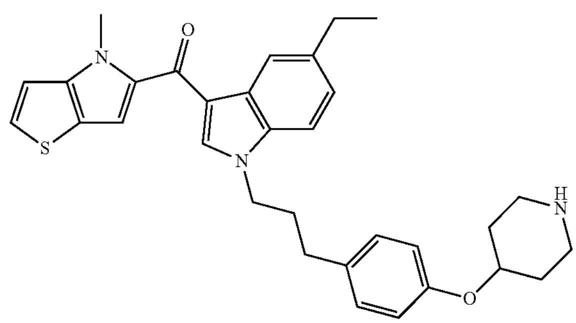 [SMILES: CCc1ccc2c(c1)c(C(=O)c1cc3sccc3n1C)cn2CCCc1ccc(OC2CCNCC2)cc1] | $^1$H NMR (DMSO-d$_6$) δ (ppm): 8.58 (bs, 2 H), 8.17 (s, 1 H), 8.12-8.08 (m, 1 H), 7.58 (d, J = 5.4 Hz, 1 H), 7.50-7.44 (m, 1 H), 7.28 (d, J = 5.4 Hz, 1 H), 7.18-7.08 (m, 4 H), 6.91-6.83 (m, 2 H), 4.61-4.52 (m, 1 H), 4.29 (t, J = 7.1 Hz, 2 H), 4.01 (s, 3 H), 3.26-3.15 (m, 2 H), 3.10-2.99 (m, 2 H), 2.73 (q, J = 7.8 Hz, 2 H), 2.55 (t, J = 7.3 Hz, 2 H), 2.14-1.98 (m, 4 H), 1.83-1.72 (m, 2 H), 1.24 (t, J = 7.8 Hz, 3 H); MS (ESI): m/z: 526 [M + H]$^+$. |
| 32 | [5-methyl-1-[3-[4-(4-piperidyloxy)phenyl]propyl]indol-3-yl]-(4-methylthieno[3,2-b]pyrrol-5-yl)methanone hydrochloride | 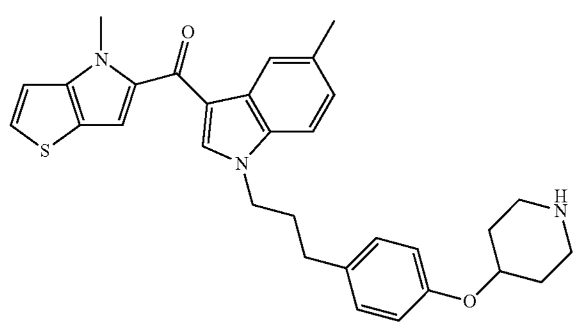 [SMILES: Cc1ccc2c(c1)c(C(=O)c1cc3sccc3n1C)cn2CCCc1ccc(OC2CCNCC2)cc1] | $^1$H NMR (DMSO-d$_6$) δ (ppm): 8.51 (bs, 2 H), 8.16 (s, 1 H), 8.09-8.05 (m, 1 H), 7.58 (d, J = 5.4 Hz, 1 H), 7.47-7.42 (m, 1 H), 7.28 (d, J = 5.4 Hz, 1 H), 7.16 (s, 1 H), 7.13-7.07 (m, 3 H), 6.91-6.84 (m, 2 H), 4.59-4.52 (m, 1 H), 4.28 (t, J = 7.1 Hz, 2 H), 4.01 (s, 3 H), 3.26-3.16 (m, 2 H), 3.10-2.99 (m, 2 H), 2.55 (t, J = 7.3 Hz, 2 H), 2.43 (s, 3 H), 2.14-1.97 (m, 4 H), 1.82-1.71 (m, 2 H); MS (ESI): m/z: 512 [M + H]$^+$. |

| No. | Name | Structure | Analytical Data |
|---|---|---|---|
| 33 | (4-methylthieno[3,2-b]pyrrol-5-yl)-[1-[2-[4-(4-piperidylmethoxy)phenyl]ethyl]indol-3-yl]methanone hydrochloride | 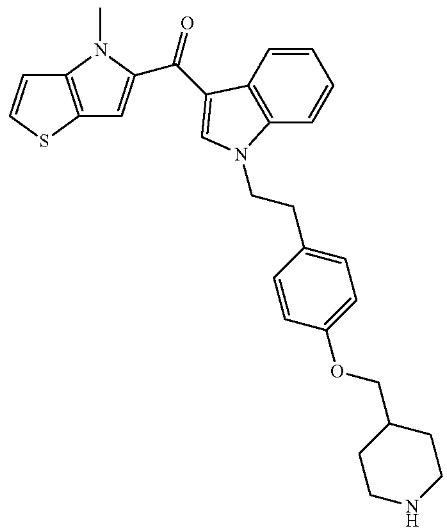 [SMILES: Cn1c(C(=O)c2cn(CCc3ccc(OCC4CCNCC4)cc3)c3ccccc23)cc2sccc21] | $^1$H NMR (DMSO-d$_6$) δ (ppm): 8.38 (br. s, 2 H), 8.25-8.19 (m, 1 H), 7.88 (s, 1 H), 7.70-7.64 (m, 1 H), 7.58 (d, J = 5.4 Hz, 1 H), 7.33-7.19 (m, 3 H), 7.09-7.04 (m, 2 H), 6.88-6.80 (m, 2 H), 6.69 (s, 1 H), 4.51 (t, J = 6.8 Hz, 2 H), 3.98 (s, 3 H), 3.81 (d, J = 5.9 Hz, 2 H), 3.29-3.21 (m, 2 H), 3.06 (t, J = 6.8 Hz, 2 H), 2.94-2.80 (m, 2 H), 2.09-1.95 (m, 1 H), 1.92-1.83 (m, 2 H), 1.51-1.36 (m, 2 H); MS (ESI): m/z: 498 [M + H]$^+$. |
| 34 | (4-methylthieno[3,2-b]pyrrol-5-yl)-[1-[2-[4-(4-piperidyloxy)phenyl]ethyl]indol-3-yl]methanone hydrochloride | 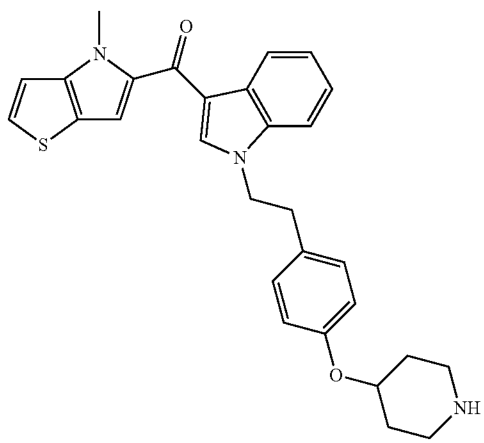 [SMILES: Cn1c(C(=O)c2cn(CCc3ccc(OC4CCNCC4)cc3)c3ccccc23)cc2sccc21] | $^1$H NMR (DMSO-d$_6$) δ (ppm): 8.51 (br. s, 2 H), 8.27-8.14 (m, 1 H), 7.91 (s, 1 H), 7.68-7.62 (m, 1 H), 7.58 (d, J = 5.4 Hz, 1 H), 7.31-7.20 (m, 3 H), 7.11-7.03 (m, 2 H), 6.93-6.86 (m, 2 H), 6.71 (s, 1 H), 4.61-4.45 (m, 3 H), 3.99 (s, 3 H), 3.24-3.13 (m, 2 H), 3.09-2.92 (m, 4 H), 2.11-1.97 (m, 2 H), 1.81-1.70 (m, 2 H); MS (ESI): m/z: 484 [M + H]$^+$. |
| 35 | (4-methylthieno[3,2-b]pyrrol-5-yl)-[1-[2-[4-[2-(4-piperidyl)ethoxy]phenyl]ethyl]indol-3-yl]methanone hydrochloride | 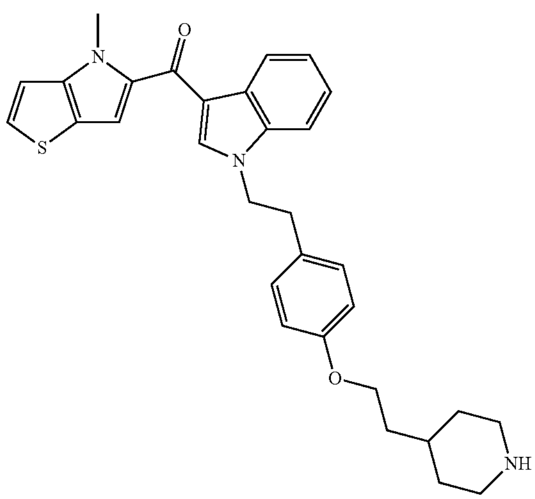 [SMILES: Cn1c(C(=O)c2cn(CCc3ccc(OCCC4CCNCC4)cc3)c3ccccc23)cc2sccc21] | $^1$H NMR (CDCl$_3$) δ (ppm): 8.49-8.15 (m, 3 H), 7.85 (s, 1 H), 7.69-7.64 (m, 1 H), 7.58 (d, J = 5.4 Hz, 1 H), 7.34-7.18 (m, 3 H), 7.08-7.01 (m, 2 H), 6.87-6.79 (m, 2 H), 6.65 (s, 1 H), 4.50 (t, J = 6.8 Hz, 2 H), 4.03-3.88 (m, 5 H), 3.24-3.14 (m, 2 H), 3.06 (t, J = 6.8 Hz, 2 H), 2.86-2.74 (m, 2 H), 1.87-1.59 (m, 5 H), 1.37-1.22 (m, 2 H); MS (ESI): m/z: 512 [M + H]$^+$. |

EXAMPLE 2

Biological Testing 2.1 Assay of Enzyme Inhibition of KDM1A (LSD1)

The KDM1A inhibiting activity was determined using a TR-FRET assay (time resolved fluorescence resonance energy transfer, Lance® Ultra Demethylase technology (Perkin Elmer, Waltham, Mass., USA)), which comprises a Europium chelate donor dye (TRF0404, Perkin Elmer, Waltham, Mass., USA) together with ULight™ (TR0102, Perkin Elmer, Waltham, Mass., USA), a small molecular weight acceptor dye with a red-shifted fluorescent emission, and a biotinylated 21 amino acids histone H3-derived monomethylated peptide (H3K4me) [Lys(Me1)4]-Histone H3 (1-21)-GGK(biotin), (64355, Anaspec, Fremont, Calif., USA) as substrate. The intensity of the light emission is proportional to the level of biotinylated reaction product. The complex of human recombinant KDM1A/CoREST protein was produced in *E. coli* as separate proteins and co-purified as previously described.(Forneris, F. et al. Trends Biochem, Sci, 2008, 33, 181-189) (Forneris, F. et al. J. Biol. Chem. 2007, 282, 20070-20074).

Demethylase Assay conditions: 0.25 nM KDM1A/CoREST protein and compound in 100% DMSO were added in a final volume of 48 µL assay buffer (Tris HCl 50 mM pH 8.8, NaCl 50 mM, DTT 1 mM, Tween-20 0.01% (by volume)) to each well of a 96 well half area flat bottom white plate (3693 Costar, Sigma-Aldrich, St. Louis, M, USA).

Demethylase reaction was started by the addition of 50 nM histone H3K4 monomethylated. After 20 min at RT, 300 µM tranylcypromine (P8511-1G, Sigma-Aldrich, St. Louis, Mo. 63103) was added to stop the reaction.

Detection step conditions: 10 µL of the assay mixture was transferred from the original plate into a 384 well white plate (6007290 OptiPlate™, Perkin Elmer, Waltham, Mass., USA) and 10 µL of the detection Mix containing 2 nM Eu-antibody and 10 nM U-Light-Streptavidin in 1× Lance Detection Buffer (TRF0404, TR0102, CR97100, Perkin Elmer, Waltham, Mass., USA). The resulting mixture was incubated in the dark for 1 h at RT. Then, TR-FRET signal was read by a fluorimeter (Infinite® F200, Tecan, Männedorf, Switzerland) (Excitation 320 nm, Emission 665 nm and 620 nm, delay time 50 µs, window time 100 µs).

$IC_{50}$ determination: The inhibitor concentrations ranged from 0.025 to 500 µM (serial 1:3 dilutions). The $IC_{50}$ was calculated using GraphPad Software.

Compounds 1-2, 5-6, and 8 exhibit $IC_{50}$ values of less than 50 µM, Compound 11 exhibits an $IC_{50}$ value of less than 5 µM, and Compounds 12-30 exhibit $IC_{50}$ values of less than 0.5 µM.

2.2 Cell Growth

CellTiter-Flor® (Promega) is as a nonlytic, single-reagent-addition fluorescence assay that measures the relative number of living cells in a culture population after experimental manipulation. The CellTiter-Fluor™ Cell Viability Assay measures the conserved and constitutive protease activity within live cells and therefore acts as a marker for cell viability.

Human leukemia MV4-11 cells, (obtained from the Deutsche Sammlung von Mikroorganismen und Zellkulturen, ACC 102) or NB4 cells, (obtained from the Deutsche Sammlung von Mikroorganismen und Zellkulturen) in exponential growth, were incubated for 48 h with different concentrations of the inhibitors. After 48 h a volume of CellTiter-Fluor® Reagent equal to one fifth of volume of cell culture medium was added. The content was mixed and incubates for at least 90 min at 37° C. degree to obtain a stable signal. The fluorescence was recorded using an excitation wavelength of 360 nm and an emission at 535 nm. The $IC_{50}$ was calculated using GraphPad Software. Compounds 11 and 13-19 exhibit $IC_{50}$ values of less than 10 µM against human leukemia MV4-11 cells, compounds 11 and 13-24 $IC_{50}$ values of less than 10 µM against human leukemia NB4 cells.

2.3 Bioluminescent-Coupled Assay for Monoamine Oxidases (MAO-Glo Assay)

The MAO Glo Assay from Promega (cat. V1402, Promega, Madison, Wis.) was used to measure the effect of inhibitors on MAO A and MAO B activity. Human recombinant MAO A and MAO B were expressed in *Pichia pastoris* and purified as published (Binda C. et al. Proc. Natl. Acad. Sci. USA, 2003, 9750-9755). The assay was performed at RT in 50 µL (25 µL reaction solution+25 µL detection reagent) in 96 well half area white plates (cat. 3693, Corning, Corning, N.Y.). Luminescence was measured after 20 min incubation in the dark using a microplate reader (Infinite F200, Tecan Group, Switzerland) with an integration time of 0.25 s per well. 50 nM MAO A or 125 nM MAO B were incubated with five different inhibitor concentrations (from 0.004 µM to 100 µM) for 15 min at RT in Promega MAO Buffer or Promega MAO B Buffer (MAO Glo Assay kit, catalogue number V1402, Promega, Madison, Wis.). After 30 min of incubation the reaction was stopped with the Promega detection reagent. All compounds were tested twice and $IC_{50}$ values were calculated using GraphPad Prism version 4.0 (GraphPad Software, San Diego, Calif.).

Compounds 13-14, and 17-18 were at least 10 times more active against KDM1A (LSD1) compared to both MAO A and MAO B.

The invention claimed is:
1. A compound of formula (I)

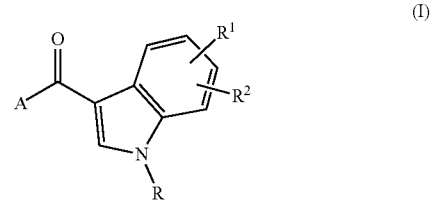

wherein
A is

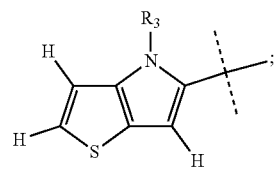

R is hydrogen or $L^1$-$R^5$;
$R^1$ and $R^2$ are independently, hydrogen, OH, $C_1$-$C_4$-alkyl, $C_3$-$C_7$ cycloalkyl, aryl, or heteroaryl;
$R_3$ is hydrogen or $C_1$-$C_4$-alkyl;
$L^1$ is a bond, —$(CH_2)_j$—Y—, or —$(CH_2)_k$—,
j is an integer from 2 to 6;
k is an integer from 1 to 6;
Y is oxygen;

R⁵ is C₁-C₄-alkyl or aryl, wherein the aryl is optionally substituted by one or two halogen, C₁-C₆-alkyl, or L²-R⁶;
L² is —(CH₂)ₘ— or —(CH₂)ₙ—W—(CH₂)ₚ—;
R⁶ is heterocyclyl optionally substituted by C₁-C₆-alkyl;
m, n, and p are, independently, zero or an integer from 1 to 6; and
W is oxygen, NH, or CH₂;
or a stereoisomer or a pharmaceutically acceptable salt thereof.

2. The compound according to claim 1, wherein R₃ is methyl or ethyl.

3. The compound according to claim 1, wherein
R is hydrogen or L¹-R⁵;
R¹ and R² are, independently, hydrogen, OH, or C₁-C₄-alkyl;
R₃ is methyl or ethyl;
L¹ is a bond, —(CH₂)₂—Y—, or —(CH₂)ₖ—;
k is an integer from 1 to 4;
Y is oxygen;
R⁵ is C₁-C₄-alkyl or phenyl substituted by one or two L²-R⁶;
L² is —W—(CH₂)ₚ—;
R⁶ is heterocyclyl optionally substituted by C₁-C₆-alkyl;
p is zero or 1; and
W is oxygen;
or a stereoisomer or a pharmaceutically acceptable salt thereof.

4. The compound according to claim 1, wherein
R is hydrogen or L¹-R⁵;
R¹ and R² are, independently, H or methyl;
R₃ is methyl or ethyl;
L¹ is —(CH₂)ⱼ—Y— or —(CH₂)ₖ—;
j is 2;
k is 3;
R⁵ is methyl or phenyl substituted by one or two L²-R⁶;
L² is —(CH₂)ₙ—W—(CH₂)ₚ—;
n is 0;
p is 0 or 1; and
W is oxygen;
or a stereoisomer or a pharmaceutically acceptable salt thereof.

5. The compound according to claim 1, wherein
R is L¹-R⁵;
R¹ and R² are hydrogen;
R₃ is methyl or ethyl;
L¹ is —(CH₂)ⱼ—Y— or —(CH₂)ₖ—;
j is 2;
k is 3;
R⁵ is phenyl substituted by one or two L²-R⁶;
L² is —(CH₂)ₙ—W—(CH₂)ₚ—;
n is 0;
p is 0 or 1; and
W is oxygen;
or a stereoisomer or a pharmaceutically acceptable salt thereof.

6. The compound according to claim 1, wherein
R is L¹-R⁵;
R¹ and R² are hydrogen;
R₃ is methyl;
L¹ is —(CH₂)ⱼ—Y—;
j is 2;
R⁵ is phenyl substituted by L²-R⁶;
L² is —(CH₂)ₙ—W—(CH₂)ₚ—;
n is 0;
p is 0 or 1; and
W is oxygen;
or a stereoisomer or a pharmaceutically acceptable salt thereof.

7. The compound according to claim 1, wherein wherein R⁶ is piperidinyl or pyrrolidinyl.

8. A compound selected from the group consisting of:
1H-indol-3-yl-(4-methylthieno[3,2-b]pyrrol-5-yl)methanone;
(5-methyl-1H-indol-3-yl)-(4-methylthieno[3,2-b]pyrrol-5-yl)methanone;
(5-ethyl-1H-indol-3-yl)-(4-methylthieno[3,2-b]pyrrol-5-yl)methanone;
(5-bromo-1H-indol-3-yl)-(4-methylthieno[3,2-b]pyrrol-5-yl)methanone;
(4-ethylthieno[3,2-b]pyrrol-5-yl)-(1H-indol-3-yl)methanone;
1H-indol-3-yl-(6-methylthieno[2,3-b]pyrrol-5-yl)methanone;
(1-methylindol-3-yl)-(4-methylthieno[3,2-b]pyrrol-5-yl)methanone;
[1-(2-methoxyethyl)indol-3-yl]-(4-methylthieno[3,2-b]pyrrol-5-yl)methanone;
(4-methylthieno[3,2-b]pyrrol-5-yl)-[1-(2-phenoxyethyl)indol-3-yl]methanone;
(4-methylthieno[3,2-b]pyrrol-5-yl)-[1-[2-[2-(pyrrolidin-3-ylmethoxy)phenoxy]ethyl]indol-3-yl]methanone;
(4-methylthieno[3,2-b]pyrrol-5-yl)-[1-[2-[3-(pyrrolidin-3-ylmethoxy)phenoxy]ethyl]indol-3-yl]methanone;
(4-methylthieno[3,2-b]pyrrol-5-yl)-[1-[2-[3-[[(3S)-pyrrolidin-3-yl]methoxy]phenoxy]ethyl]indol-3-yl]methanone;
(4-methylthieno[3,2-b]pyrrol-5-yl)-[1-[2-[3-[[(3R)-pyrrolidin-3-yl]methoxy]phenoxy]ethyl]indol-3-yl]methanone;
(4-methylthieno[3,2-b]pyrrol-5-yl)-[1-[2-[4-(pyrrolidin-3-ylmethoxy)phenoxy]ethyl]indol-3-yl]methanone;
(4-methylthieno[3,2-b]pyrrol-5-yl)-[1-[2-[3-(4-piperidyloxy)phenoxy]ethyl]indol-3-yl]methanone;
(4-methylthieno[3,2-b]pyrrol-5-yl)-[1-[2-[4-(4-piperidyloxy)phenoxy]ethyl]indol-3-yl]methanone;
(4-methylthieno[3,2-b]pyrrol-5-yl)-[1-[2-[3-(4-piperidylmethoxy)phenoxy]ethyl]indol-3-yl]methanone;
(4-methylthieno[3,2-b]pyrrol-5-yl)-[1-[2-[4-(4-piperidylmethoxy)phenoxy]ethyl]indol-3-yl]methanone;
[1-[2-[3-(azepan-4-yloxy)phenoxy]ethyl]indol-3-yl]-(4-methylthieno[3,2-b]pyrrol-5-yl)methanone;
[1-[2-[4-(azepan-4-yloxy)phenoxy]ethyl]indol-3-yl]-(4-methylthieno[3,2-b]pyrrol-5-yl)methanone;
(4-methylthieno[3,2-b]pyrrol-5-yl)-[1-[3-[4-(pyrrolidin-3-ylmethoxy)phenyl]propyl]indol-3-yl]methanone;
(4-methylthieno[3,2-b]pyrrol-5-yl)-[1-[3-[4-(4-piperidylmethoxy)phenyl]propyl]indol-3-yl]methanone;
(4-methylthieno[3,2-b]pyrrol-5-yl)-[1-[3-[4-(4-piperidyloxy)phenyl]propyl]indol-3-yl]methanone;
[1-[3-[4-(azepan-4-yloxy)phenyl]propyl]indol-3-yl]-(4-methylthieno[3,2-b]pyrrol-5-yl)methanone;
[1-[3-[3,4-bis(4-piperidylmethoxy)phenyl]propyl]indol-3-yl]-(4-methylthieno[3,2-b]pyrrol-5-yl)methanone;
(4-ethylthieno[3,2-b]pyrrol-5-yl)-[1-[3-[4-(4-piperidyloxy)phenyl]propyl]indol-3-yl]methanone;
(4-ethylthieno[3,2-b]pyrrol-5-yl)-[1-[3-[4-(pyrrolidin-3-ylmethoxy)phenyl]propyl]indol-3-yl]methanone;
(6-methylthieno[2,3-b]pyrrol-5-yl)-[1-[3-[4-(pyrrolidin-3-ylmethoxy)phenyl]propyl]indol-3-yl]methanone;
(6-methylthieno[2,3-b]pyrrol-5-yl)-[1-[3-[4-(4-piperidyloxy)phenyl]propyl]indol-3-yl]methanone;
[5-ethyl-1-[3-[4-(4-piperidyloxy)phenyl]propyl]indol-3-yl]-(4-methylthieno[3,2-b]pyrrol-5-yl)methanone; and

[5-methyl-1-[3-[4-(4-piperidyloxy)phenyl]propyl]indol-3-yl]-(4-methylthieno[3,2-b]pyrrol-5-yl)methanone;

or a stereoisomer or a pharmaceutically acceptable salt of any of the foregoing.

9. A pharmaceutical composition comprising a compound of claim 1 and a pharmaceutically acceptable excipient and/or diluent.

10. The pharmaceutical composition according to claim 9 further comprising at least one therapeutic agent, wherein the therapeutic agent is a histone deacetylase inhibitor, retinoid receptor modulator, antiproliferative/antineoplastic agent, cytostatic agent, agent that inhibits cancer cell invasion, inhibitor of growth factor function, antiangiogenic agent, cell cycle inhibitor, proteasome inhibitor, HSP90 inhibitor, selective COX-2 inhibitor, or a chemotherapeutic agent.

11. The pharmaceutical composition according to claim 9, wherein the pharmaceutical composition is in the form of a tablet, capsule, oral preparation, powder, granule, pill, injectable or infusible liquid, solution, suspension, emulsion, suppository, ointment, cream, lotion, gel, paste, or transdermal delivery device.

12. A method of treating leukemia, non-small cell lung cancer, hepatocellular carcinoma, or glioblastoma comprising administering a therapeutically effective amount of a compound of claim 1 to a subject in need thereof.

13. A method of treating acute myeloid leukemia comprising administering a therapeutically effective amount of a compound of claim 1 to a subject in need thereof.

14. The method of claim 12, further comprising administering a therapeutically effective amount of at least one therapeutic agent, wherein the therapeutic agent is a histone deacetylase inhibitor, retinoid receptor modulator, antiproliferative/antineoplastic agent, cytostatic agent, agent that inhibits cancer cell invasion, inhibitor of growth factor function, antiangiogenic agent, cell cycle inhibitor, proteasome inhibitor, HSP90 inhibitor, selective COX-2 inhibitor, or a chemotherapeutic agent.

15. The method of claim 13, further comprising administering a therapeutically effective amount of at least one therapeutic agent, wherein the therapeutic agent is a histone deacetylase inhibitor, retinoid receptor modulator, antiproliferative/antineoplastic agent, cytostatic agent, agent that inhibits cancer cell invasion, inhibitor of growth factor function, antiangiogenic agent, cell cycle inhibitor, proteasome inhibitor, HSP90 inhibitor, selective COX-2 inhibitor, or a chemotherapeutic agent.

16. A process for obtaining a compound of formula (I) according to claim 1, wherein R is hydrogen, the process comprising the preparation of the acyl chloride of formula A2 by reaction of the carboxylic acid of formula A1 with thionyl chloride, and the preparation of the indole anion A4 by reaction of indole A3 with methyl magnesium bromide, and the condensation of the acyl chloride of formula A2 with indole anion A4 to obtain a compound of formula (I), as represented below:

wherein $R^1$, $R^2$, $R_3$, and $R_4$ are as defined in claim 1.

17. A process for obtaining a compound of formula (I) according to claim 1, wherein R is $L^1$-$R^5$, the process comprising the reaction of a compound of formula B1 with a compound of formula B2 in presence of a base, as represented below:

wherein $R^1$, $R^2$, $R_3$, $R_4$, $L^1$, and $R^5$ are as defined in claim 1, and LG is a leaving group.

18. The process according to claim 17, wherein LG is bromine.

19. A compound of formula (I)

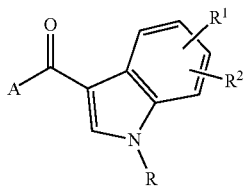

wherein
A is

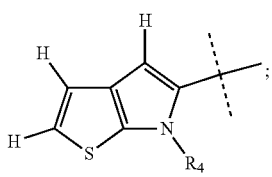

R is $L^1$-$R^5$;
$R^1$ and $R^2$ are, independently, hydrogen, OH, $C_1$-$C_4$-alkyl, $C_3$-$C_7$ cycloalkyl, aryl, or heteroaryl;
$R^4$ is hydrogen or $C_1$-$C_4$-alkyl;
$L^1$ is a bond, —$(CH_2)_j$—Y—, or —$(CH_2)_k$—;
j is an integer from 2 to 6;
k is an integer from 1 to 6;
Y is oxygen;
$R^5$ is aryl optionally substituted by one or two halogen, $C_1$-$C_6$-alkyl, or $L^2$-$R^6$;
$L^2$ is —$(CH_2)_m$— or —$(CH_2)_n$—W—$(CH_2)_p$—;
$R^6$ is heterocyclyl optionally substituted by $C_1$-$C_6$-alkyl;
m, n, and p are, independently, zero or an integer from 1 to 6; and
W is oxygen, NH, or $CH_2$;
or a stereoisomer or a pharmaceutically acceptable salt thereof.

20. A pharmaceutical composition comprising a compound of claim 19 and a pharmaceutically acceptable excipient and/or diluent.

21. The pharmaceutical composition according to claim 20 further comprising at least one therapeutic agent, wherein the therapeutic agent is a histone deacetylase inhibitor, retinoid receptor modulator, antiproliferative/antineoplastic agent, cytostatic agent, agent that inhibits cancer cell invasion, inhibitor of growth factor function, antiangiogenic agent, cell cycle inhibitor, proteasome inhibitor, HSP90 inhibitor, selective COX-2 inhibitor, or a chemotherapeutic agent.

22. The pharmaceutical composition according to claim 20, wherein the pharmaceutical composition is in the form of a tablet, capsule, oral preparation, powder, granule, pill, injectable or infusible liquid, solution, suspension, emulsion, suppository, ointment, cream, lotion, gel, paste, or transdermal delivery device.

23. A method of treating leukemia, non-small cell lung cancer, hepatocellular carcinoma, or glioblastoma comprising administering a therapeutically effective amount of a compound of claim 19 to a subject in need thereof.

24. A method of treating acute myeloid leukemia comprising administering a therapeutically effective amount of a compound of claim 19 to a subject in need thereof.

25. The method of claim 23, further comprising administering a therapeutically effective amount of at least one therapeutic agent, wherein the therapeutic agent is a histone deacetylase inhibitor, retinoid receptor modulator, antiproliferative/antineoplastic agent, cytostatic agent, agent that inhibits cancer cell invasion, inhibitor of growth factor function, antiangiogenic agent, cell cycle inhibitor, proteasome inhibitor, HSP90 inhibitor, selective COX-2 inhibitor, or a chemotherapeutic agent.

26. The method of claim 24, further comprising administering a therapeutically effective amount of at least one therapeutic agent, wherein the therapeutic agent is a histone deacetylase inhibitor, retinoid receptor modulator, antiproliferative/antineoplastic agent, cytostatic agent, agent that inhibits cancer cell invasion, inhibitor of growth factor function, antiangiogenic agent, cell cycle inhibitor, proteasome inhibitor, HSP90 inhibitor, selective COX-2 inhibitor, or a chemotherapeutic agent.

* * * * *

UNITED STATES PATENT AND TRADEMARK OFFICE
CERTIFICATE OF CORRECTION

| | | |
|---|---|---|
| PATENT NO. | : 10,980,777 B2 | Page 1 of 1 |
| APPLICATION NO. | : 16/640030 | |
| DATED | : April 20, 2021 | |
| INVENTOR(S) | : Mario Varasi et al. | |

It is certified that error appears in the above-identified patent and that said Letters Patent is hereby corrected as shown below:

On the Title Page

(56) References Cited, Other Publications, page 2, first column, Lines 7-12:
"Gooden et al. "Facile synthesis of substituted trans-2-arylcyclopropylamine inhibitors of the human histone demethylase LSD1 and monoamine oxidases a", Science Direct, Bioorganic & Medicinal Chemistry Letters, 2008, vol. 18, p. 3047-3051."

Should read:
-- Gooden et al. "Facile synthesis of substituted trans-2-arylcyclopropylamine inhibitors of the human histone demethylase LSD1 and monoamine oxidases A", Science Direct, Bioorganic & Medicinal Chemistry Letters, 2008, vol. 18, p. 3047-3051. --

In the Claims

At Column 80, Claim number 1, Line number 61:
"$R^1$ and $R^2$ are independently, hydrogen, OH, $C_1$-$C_4$-alkyl,"

Should read:
-- $R^1$ and $R^2$ are, independently, hydrogen, OH, $C_1$-$C_4$-alky, --

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*